(12) United States Patent
Emery et al.

(10) Patent No.: US 12,377,293 B2
(45) Date of Patent: Aug. 5, 2025

(54) SYSTEMS AND METHODS FOR MEASURING ELASTICITY WITH IMAGING OF ULTRASOUND MULTI-FOCUS SHEARWAVES IN MULTIPLE DIMENSIONS

(71) Applicant: Ulthera, Inc., Mesa, AZ (US)

(72) Inventors: Charles D. Emery, Gilbert, AZ (US); Stephen John Hsu, Mesa, AZ (US)

(73) Assignee: Ulthera, Inc., Raleigh, NC (US)

( * ) Notice: Subject to any disclaimer, the term of this patent is extended or adjusted under 35 U.S.C. 154(b) by 436 days.

(21) Appl. No.: 17/624,805

(22) PCT Filed: Jul. 13, 2020

(86) PCT No.: PCT/US2020/041783
§ 371 (c)(1),
(2) Date: Jan. 4, 2022

(87) PCT Pub. No.: WO2021/011458
PCT Pub. Date: Jan. 21, 2021

(65) Prior Publication Data
US 2022/0266063 A1     Aug. 25, 2022

Related U.S. Application Data

(60) Provisional application No. 62/874,374, filed on Jul. 15, 2019.

(51) Int. Cl.
*A61N 7/02* (2006.01)
*A61B 8/00* (2006.01)
(Continued)

(52) U.S. Cl.
CPC .............. *A61N 7/02* (2013.01); *A61B 8/0858* (2013.01); *A61B 8/4477* (2013.01); *A61B 8/485* (2013.01);
(Continued)

(58) Field of Classification Search
CPC ..... A61B 8/0858; A61B 8/4477; A61B 8/485; A61N 2007/0008; A61N 2007/0034;
(Continued)

(56) References Cited

U.S. PATENT DOCUMENTS 2,427,348 A    9/1947  Bond et al.
2,792,829 A    2/1952  Calosi
(Continued)

FOREIGN PATENT DOCUMENTS

CN    2460061    11/2001
CN    1734284    12/2009
(Continued)

OTHER PUBLICATIONS

US 10,398,895 B2, 09/2019, Schwarz (withdrawn)
(Continued)

*Primary Examiner* — Mark D Remaly
(74) *Attorney, Agent, or Firm* — Knobbe, Martens, Olson & Bear, LLP

(57) ABSTRACT

Embodiments of a dermatological cosmetic treatment and/or imaging system and method adapted to alter placement and position of multiple (e.g., two or more) cosmetic treatment zones in tissue from ultrasound beams from a transducer, simultaneous multi-focus therapy at multiple depths, and/or dithering ultrasound beams from a transducer to alter placement and position of multiple cosmetic treatment zones in tissue. The system can include a hand wand, a removable transducer module, and a control module. In some embodiments, the cosmetic treatment system may be used in various cosmetic procedures.

20 Claims, 32 Drawing Sheets

(51) Int. Cl.
*A61B 8/08* (2006.01)
*A61N 7/00* (2006.01)

(52) U.S. Cl.
CPC ............... *A61N 2007/0052* (2013.01); *A61N 2007/0056* (2013.01); *A61N 2007/0073* (2013.01); *A61N 2007/027* (2013.01)

(58) Field of Classification Search
CPC .... A61N 2007/0039; A61N 2007/0052; A61N 2007/0056; A61N 2007/0065; A61N 2007/0073; A61N 2007/0091; A61N 2007/027; A61N 7/02
See application file for complete search history.

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,151,834 A | 5/1979 | Sato et al. |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,417,170 A | 11/1983 | Benisncasa |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,587,971 A | 5/1986 | Stolfi |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,054,491 A | 10/1991 | Saito et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,142,511 A | 8/1992 | Kanai et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,329,202 A | 7/1994 | Garlick et al. |
| 5,348,016 A | 9/1994 | Unger et al. |
| 5,358,466 A | 10/1994 | Aida et al. |
| 5,360,268 A | 11/1994 | Hayashi |
| 5,370,121 A | 12/1994 | Reichenberger |
| 5,370,122 A | 12/1994 | Kunig |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |

(56) References Cited

U.S. PATENT DOCUMENTS

| | | |
|---|---|---|
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams |
| 5,413,550 A | 5/1995 | Castel |
| 5,417,216 A | 5/1995 | Tanaka |
| 5,423,220 A | 6/1995 | Finsterwald et al. |
| 5,435,311 A | 7/1995 | Umemura |
| 5,438,998 A | 8/1995 | Hanafy |
| 5,443,068 A | 8/1995 | Cline et al. |
| 5,445,611 A | 8/1995 | Eppstein et al. |
| 5,458,596 A | 10/1995 | Lax |
| 5,460,179 A | 10/1995 | Okunuki et al. |
| 5,460,595 A | 10/1995 | Hall et al. |
| 5,419,327 A | 11/1995 | Rohwedder |
| 5,469,854 A | 11/1995 | Unger et al. |
| 5,471,488 A | 12/1995 | Fujio |
| 5,472,405 A | 12/1995 | Buchholtz et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,511,296 A | 4/1996 | Dias et al. |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenchein |
| 5,524,624 A | 6/1996 | Tepper |
| 5,524,625 A | 6/1996 | Okazaki |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,573,497 A | 11/1996 | Chapelon |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,643,179 A | 1/1997 | Fujimoto |
| 5,601,526 A | 2/1997 | Chapelon |
| 5,603,323 A | 2/1997 | Pflugrath et al. |
| 5,605,154 A | 2/1997 | Ries et al. |
| 5,609,562 A | 3/1997 | Kaali |
| 5,615,091 A | 3/1997 | Palatnik |
| 5,618,275 A | 4/1997 | Bock |
| 5,620,479 A | 4/1997 | Diederich |
| 5,622,175 A | 4/1997 | Sudol et al. |
| 5,617,858 A | 5/1997 | Taverna et al. |
| 5,638,819 A | 6/1997 | Manwaring et al. |
| 5,644,085 A | 7/1997 | Lorraine et al. |
| 5,647,373 A | 7/1997 | Paltieli |
| 5,655,535 A | 8/1997 | Frlemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,740,804 A | 4/1998 | Cerofolini |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,866,024 A | 2/1999 | de Villeneuve |
| 5,869,751 A | 2/1999 | Bonin |
| 5,871,524 A | 2/1999 | Knowlton |
| 5,873,902 A | 2/1999 | Sanghvi |
| 5,876,341 A | 3/1999 | Wang et al. |
| 5,879,303 A | 3/1999 | Averkiou et al. |
| 5,882,557 A | 3/1999 | Hayakawa |
| 5,884,627 A | 3/1999 | Wakabayashi et al. |
| 5,891,034 A | 4/1999 | Bucholz |
| 5,895,356 A | 4/1999 | Andrus et al. |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,964,707 A | 10/1999 | Fenster et al. |
| 5,967,980 A | 10/1999 | Ferre et al. |
| 5,968,034 A | 10/1999 | Fullmer |
| 5,971,949 A | 10/1999 | Levin |
| 5,977,538 A | 11/1999 | Unger et al. |
| 5,984,881 A | 11/1999 | Ishibashi et al. |
| 5,984,882 A | 11/1999 | Rosenchein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,014,473 A | 1/2000 | Hossack et al. |
| 6,016,255 A | 1/2000 | Bolan et al. |
| 6,019,724 A | 2/2000 | Gronningsaeter et al. |
| 6,022,308 A | 2/2000 | Williams |

(56) References Cited

U.S. PATENT DOCUMENTS

| | | |
|---|---|---|
| 6,022,317 A | 2/2000 | Cruanas et al. |
| 6,022,327 A | 2/2000 | Chang |
| 6,030,374 A | 2/2000 | McDaniel |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,148 A | 7/2000 | Fujimoto |
| 6,093,883 A | 7/2000 | Sanghvi |
| 6,100,626 A | 8/2000 | Frey et al. |
| 6,101,407 A | 8/2000 | Groezinger |
| 6,106,469 A | 8/2000 | Suzuki et al. |
| 6,113,558 A | 9/2000 | Rosenchein |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias |
| 6,190,336 B1 | 2/2001 | Duarte |
| 6,193,658 B1 | 2/2001 | Wendelken |
| 6,198,956 B1 | 3/2001 | Dunne |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,287,304 B1 | 9/2001 | Eggers et al. |
| 6,296,619 B1 | 10/2001 | Brisken |
| 6,301,989 B1 | 10/2001 | Brown et al. |
| 6,307,302 B1 | 10/2001 | Toda |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,447,443 B1 | 9/2002 | Keogh et al. |
| 6,450,979 B1 | 9/2002 | Miwa et al. |
| 6,451,013 B1 | 9/2002 | Bays et al. |
| 6,453,202 B1 | 9/2002 | Knowlton |
| 6,461,304 B1 | 10/2002 | Tanaka et al. |
| 6,461,378 B1 | 10/2002 | Knowlton |
| 6,470,216 B1 | 10/2002 | Knowlton |
| 6,485,420 B1 | 11/2002 | Bullis |
| 6,488,626 B1 | 12/2002 | Lizzi |
| 6,491,657 B2 | 12/2002 | Rowe |
| 6,500,121 B1 | 12/2002 | Slayton |
| 6,500,141 B1 | 12/2002 | Irion |
| 6,506,171 B1 | 1/2003 | Vitek et al. |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk |
| 6,524,250 B1 | 2/2003 | Weber |
| 6,666,835 B2 | 3/2003 | Martin |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,547,788 B1 | 4/2003 | Maguire et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,605,043 B1 | 8/2003 | Dreschel |
| 6,605,080 B1 | 8/2003 | Altshuler et al. |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,145 B1 | 11/2003 | Dreschel et al. |
| 6,645,150 B2 | 11/2003 | Angelsen et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,669,638 B1 | 12/2003 | Miller |
| 6,673,017 B1 | 1/2004 | Jackson |
| 6,685,639 B1 | 2/2004 | Wang et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |
| 6,733,449 B1 | 5/2004 | Krishnamurthy et al. |
| 6,749,624 B2 | 6/2004 | Knowlton |

(56) References Cited

U.S. PATENT DOCUMENTS

| | | |
|---|---|---|
| 6,772,490 B2 | 8/2004 | Toda |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,825,176 B2 | 11/2004 | White et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,887,260 B1 | 5/2005 | McDaniel |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,713,203 B2 | 3/2010 | Lacoste et al. |
| 7,694,406 B2 | 4/2010 | Wildes et al. |
| 7,695,437 B2 | 4/2010 | Quistgaard et al. |
| 7,727,156 B2 | 6/2010 | Angelsen et al. |
| 7,734,321 B2 | 6/2010 | White |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,828,734 B2 | 10/2010 | Azhari et al. |
| 7,824,348 B2 | 11/2010 | Barthe |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,955,281 B2 | 6/2011 | Pedersen et al. |
| 7,967,764 B2 | 6/2011 | Lidgren et al. |
| 7,967,839 B2 | 6/2011 | Flock et al. |
| 7,955,262 B2 | 7/2011 | Rosenberg |
| 7,993,289 B2 | 8/2011 | Quistgaard et al. |
| 8,057,465 B2 | 9/2011 | Sliwa, Jr. et al. |
| 8,057,389 B2 | 11/2011 | Barthe et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |
| 8,333,700 B1 | 12/2012 | Barthe et al. |
| 8,334,637 B2 | 12/2012 | Crunkilton et al. |
| 8,337,407 B2 | 12/2012 | Quistgaard et al. |
| 8,343,051 B2 | 1/2013 | Desilets et al. |
| 8,454,540 B2 | 1/2013 | Eshel et al. |
| 8,366,622 B2 | 2/2013 | Slayton et al. |
| 8,398,549 B2 | 3/2013 | Palmeri et al. |
| 8,409,097 B2 | 4/2013 | Slayton et al. |
| 8,425,435 B2 | 4/2013 | Wing et al. |
| 8,388,535 B2 | 5/2013 | Weng et al. |
| 8,444,562 B2 | 5/2013 | Barthe et al. |
| 8,460,193 B2 | 6/2013 | Barthe et al. |
| 8,480,585 B2 | 7/2013 | Slayton et al. |
| 8,486,001 B2 | 7/2013 | Weyant |
| 8,506,486 B2 | 8/2013 | Slayton et al. |
| 8,512,250 B2 | 8/2013 | Quistgaard et al. |
| 8,523,775 B2 | 9/2013 | Barthe et al. |
| 8,523,849 B2 | 9/2013 | Liu et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |

(56) References Cited

U.S. PATENT DOCUMENTS

| | | |
|---|---|---|
| 8,622,937 B2 | 1/2014 | Weng et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 | 12/2014 | Barthe et al. |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |
| 8,926,533 B2 | 1/2015 | Bockenstedt et al. |
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,050,116 B2 | 6/2015 | Homer |
| 9,095,697 B2 | 8/2015 | Barthe et al. |
| 9,107,798 B2 | 8/2015 | Azhari et al. |
| 9,114,247 B2 | 8/2015 | Barthe et al. |
| 9,180,314 B2 | 11/2015 | Desilets et al. |
| 9,216,276 B2 | 12/2015 | Slayton et al. |
| 9,220,915 B2 | 12/2015 | Liu et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,295,607 B2 | 3/2016 | Rosenberg |
| 9,308,390 B2 | 4/2016 | Youngquist |
| 9,308,391 B2 | 4/2016 | Liu et al. |
| 9,314,650 B2 | 4/2016 | Rosenberg et al. |
| 9,320,537 B2 | 4/2016 | Slayton et al. |
| 9,345,910 B2 | 5/2016 | Slayton et al. |
| 9,421,029 B2 | 8/2016 | Barthe et al. |
| 9,427,600 B2 | 8/2016 | Barthe et al. |
| 9,427,601 B2 | 8/2016 | Barthe et al. |
| 9,433,803 B2 | 9/2016 | Lin et al. |
| 9,440,093 B2 | 9/2016 | Homer |
| 9,440,096 B2 | 9/2016 | Barthe et al. |
| 9,492,645 B2 | 11/2016 | Zhou et al. |
| 9,492,686 B2 | 11/2016 | Da Silva |
| 9,498,651 B2 | 11/2016 | Sapozhnikov et al. |
| 9,510,802 B2 | 12/2016 | Barthe et al. |
| 9,522,290 B2 | 12/2016 | Slayton et al. |
| 9,532,832 B2 | 1/2017 | Ron Edoute et al. |
| 9,533,174 B2 | 1/2017 | Barthe et al. |
| 9,533,175 B2 | 1/2017 | Slayton et al. |
| 9,545,529 B2 | 1/2017 | Britva et al. |
| 9,566,454 B2 | 2/2017 | Barthe et al. |
| 9,623,267 B2 | 4/2017 | Ulric et al. |
| 9,694,211 B2 | 7/2017 | Barthe et al. |
| 9,694,212 B2 | 7/2017 | Barthe et al. |
| 9,700,340 B2 | 7/2017 | Barthe et al. |
| 9,707,412 B2 | 7/2017 | Slayton et al. |
| 9,710,607 B2 | 7/2017 | Ramdas et al. |
| 9,713,731 B2 | 7/2017 | Slayton et al. |
| 9,802,063 B2 | 10/2017 | Barthe et al. |
| 9,827,449 B2 | 11/2017 | Barthe et al. |
| 9,827,450 B2 | 11/2017 | Slayton et al. |
| 9,833,639 B2 | 12/2017 | Slayton et al. |
| 9,833,640 B2 | 12/2017 | Barthe et al. |
| 9,895,560 B2 | 2/2018 | Barthe et al. |
| 9,907,535 B2 | 3/2018 | Barthe et al. |
| 9,919,167 B2 | 3/2018 | Domankevitz |
| 9,974,982 B2 | 5/2018 | Slayton et al. |
| 9,993,664 B2 | 6/2018 | Aviad et al. |
| 10,010,721 B2 | 7/2018 | Slayton et al. |
| 10,010,724 B2 | 7/2018 | Barthe et al. |
| 10,010,725 B2 | 7/2018 | Slayton et al. |
| 10,010,726 B2 | 7/2018 | Barthe et al. |
| 10,016,626 B2 | 7/2018 | Zovrin et al. |
| 10,046,181 B2 | 8/2018 | Barthe et al. |
| 10,046,182 B2 | 8/2018 | Barthe et al. |
| 10,070,883 B2 | 9/2018 | Barthe et al. |
| 10,183,183 B2 | 1/2019 | Burdette |
| 10,226,645 B2 | 3/2019 | Barthe |
| 10,238,894 B2 | 3/2019 | Slayton et al. |
| 10,245,450 B2 | 4/2019 | Slayton et al. |
| 10,252,086 B2 | 4/2019 | Barthe et al. |
| 10,265,550 B2 | 4/2019 | Barthe et al. |
| 10,272,272 B2 | 4/2019 | Lee et al. |
| 10,300,308 B2 | 5/2019 | Seip et al. |
| 10,328,289 B2 | 6/2019 | Barthe et al. |
| 10,363,440 B2 | 6/2019 | Cho et al. |
| 10,406,383 B2 | 9/2019 | Luebcke |
| 10,420,960 B2 | 9/2019 | Emery |
| 10,420,961 B2 | 9/2019 | Lacoste |
| 10,485,573 B2 | 11/2019 | Clark, III et al. |
| 10,492,862 B2 | 12/2019 | Domankevitz |
| 10,525,288 B2 | 1/2020 | Slayton et al. |
| 10,532,230 B2 | 1/2020 | Barthe et al. |
| 10,537,304 B2 | 1/2020 | Barthe et al. |
| 10,556,123 B2 | 2/2020 | Altshuler et al. |
| 10,583,287 B2 | 3/2020 | Schwarz |
| 10,603,519 B2 | 3/2020 | Slayton et al. |
| 10,603,521 B2 | 3/2020 | Emery et al. |
| 10,603,523 B2 | 3/2020 | Slayton et al. |
| 10,610,705 B2 | 4/2020 | Barthe et al. |
| 10,610,706 B2 | 4/2020 | Barthe et al. |
| 10,639,006 B2 | 5/2020 | Choi et al. |
| 10,639,504 B2 | 5/2020 | Kim |
| 10,751,246 B2 | 8/2020 | Kaila |
| 10,772,646 B2 | 9/2020 | Lu et al. |
| 10,780,298 B2 | 9/2020 | Cain et al. |
| 10,888,716 B2 | 1/2021 | Slayton et al. |
| 10,888,717 B2 | 1/2021 | Slayton et al. |
| 10,888,718 B2 | 1/2021 | Barthe et al. |
| 10,960,235 B2 | 3/2021 | Barthe et al. |
| 10,960,236 B2 | 3/2021 | Slayton et al. |
| 11,123,039 B2 | 9/2021 | Barthe et al. |
| 11,167,155 B2 | 11/2021 | Barthe et al. |
| 11,179,580 B2 | 11/2021 | Slayton et al. |
| 11,207,547 B2 | 12/2021 | Slayton et al. |
| 11,207,548 B2 | 12/2021 | Barthe et al. |
| 11,224,895 B2 | 1/2022 | Brown et al. |
| 11,235,179 B2 | 2/2022 | Barthe et al. |
| 11,235,180 B2 | 2/2022 | Slayton et al. |
| 11,241,218 B2 | 2/2022 | Emery et al. |
| 11,400,319 B2 | 8/2022 | Barthe et al. |
| 11,697,033 B2 | 7/2023 | Barthe et al. |
| 11,969,609 B2 | 4/2024 | Emery |
| 12,076,591 B2 | 9/2024 | Emery |
| 12,102,473 B2 | 10/2024 | Barthe et al. |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1 | 10/2001 | Weng |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |

(56) References Cited

U.S. PATENT DOCUMENTS

| | | |
|---|---|---|
| 2002/0095143 A1 | 7/2002 | Key |
| 2002/0099094 A1 | 7/2002 | Anderson |
| 2002/0111569 A1 | 8/2002 | Rosenschien et al. |
| 2002/0115917 A1 | 8/2002 | Honda et al. |
| 2002/0128639 A1 | 8/2002 | Pless et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1 | 1/2003 | McDaniel |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055308 A1 | 3/2003 | Friemel et al. |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0066708 A1 | 4/2003 | Allison et al. |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0149366 A1 | 8/2003 | Stringer et al. |
| 2003/0153961 A1 | 8/2003 | Babaev |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0199794 A1 | 10/2003 | Sakurai et al. |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002658 A1 | 1/2004 | Marian, Jr. |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0030268 A1 | 2/2004 | Weng et al. |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Tosaya et al. |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0007879 A1 | 1/2005 | Nishida |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0085731 A1 | 4/2005 | Miller et al. |
| 2005/0091770 A1 | 5/2005 | Mourad et al. |
| 2005/0096542 A1 | 5/2005 | Weng |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0193820 A1 | 9/2005 | Sheljaskow et al. |
| 2005/0197681 A1 | 9/2005 | Barolet et al. |
| 2005/0228281 A1 | 10/2005 | Nefos |
| 2005/0240127 A1 | 10/2005 | Seip et al. |
| 2005/0240170 A1 | 10/2005 | Zhang et al. |
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |

(56) References Cited

U.S. PATENT DOCUMENTS

| | | |
|---|---|---|
| 2006/0089632 A1 | 4/2006 | Barthe |
| 2006/0089688 A1 | 4/2006 | Panescu |
| 2006/0094988 A1 | 5/2006 | Tosaya |
| 2006/0106325 A1 | 5/2006 | Perrier |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0224090 A1 | 10/2006 | Ostrovsky et al. |
| 2006/0229514 A1 | 10/2006 | Wiener |
| 2006/0238068 A1 | 10/2006 | May et al. |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0016039 A1 | 1/2007 | Vortman et al. |
| 2007/0032784 A1 | 2/2007 | Gilklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0078290 A1 | 4/2007 | Esenaliev |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0018553 A1 | 8/2007 | Kennedy |
| 2007/0208253 A1 | 9/2007 | Slayton |
| 2007/0219448 A1 | 9/2007 | Seip et al. |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0015435 A1 | 1/2008 | Cribbs et al. |
| 2008/0027328 A1 | 1/2008 | Klopotek |
| 2008/0033458 A1 | 2/2008 | McLean et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0086056 A1 | 4/2008 | Chang et al. |
| 2008/0097214 A1 | 4/2008 | Meyers et al. |
| 2008/0097253 A1 | 4/2008 | Pedersen et al. |
| 2008/0114251 A1 | 5/2008 | Weymer et al. |
| 2008/0139943 A1 | 6/2008 | Deng et al. |
| 2008/0139974 A1 | 6/2008 | Da Silva |
| 2008/0146970 A1 | 6/2008 | Litman et al. |
| 2008/0167556 A1 | 7/2008 | Thompson |
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1 | 8/2008 | Randall et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0214988 A1 | 9/2008 | Altshuler et al. |
| 2008/0221491 A1 | 9/2008 | Slayton |
| 2008/0223379 A1 | 9/2008 | Stuker |
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294072 A1 | 11/2008 | Crutchfield, III |
| 2008/0294073 A1 | 11/2008 | Barthe |
| 2008/0319356 A1 | 12/2008 | Cain |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0163807 A1 | 6/2009 | Sliwa |
| 2009/0171252 A1 | 7/2009 | Bockenstedt et al. |
| 2009/0171266 A1 | 7/2009 | Harris |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0230823 A1 | 9/2009 | Kushculey et al. |
| 2009/0240146 A1 | 9/2009 | Bockenstedt et al. |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1 | 2/2010 | Vortman et al. |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0056962 A1 | 3/2010 | Vortman et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Douglas et al. |
| 2010/0331715 A1 | 12/2010 | Addison et al. |
| 2011/0040171 A1 | 2/2011 | Foley et al. |
| 2011/0040190 A1 | 2/2011 | Jahnke et al. |
| 2011/0040213 A1 | 2/2011 | Dietz et al. |
| 2011/0040214 A1 | 2/2011 | Foley et al. |
| 2011/0066084 A1 | 3/2011 | Desilets et al. |
| 2011/0072970 A1 | 3/2011 | Slobodzian et al. |
| 2011/0077514 A1 | 3/2011 | Ulric et al. |
| 2011/0079083 A1 | 4/2011 | Yoo et al. |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0201976 A1 | 8/2011 | Sanghvi et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |

(56) References Cited

U.S. PATENT DOCUMENTS

| | | |
|---|---|---|
| 2011/0319793 A1 | 12/2011 | Henrik et al. |
| 2011/0319794 A1 | 12/2011 | Gertner |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035473 A1 | 2/2012 | Sanghvi et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0059288 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191019 A1 | 7/2012 | Desilets et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0203108 A1 | 8/2012 | Tsujita |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1 | 10/2012 | Barthe et al. |
| 2012/0277587 A1 | 11/2012 | Adanny et al. |
| 2012/0277639 A1 | 11/2012 | Pollock et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0073001 A1 | 3/2013 | Campbell |
| 2013/0096471 A1 | 4/2013 | Slayton et al. |
| 2013/0096596 A1 | 4/2013 | Schafer |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0278111 A1 | 10/2013 | Sammoura |
| 2013/0281853 A1 | 10/2013 | Slayton et al. |
| 2013/0281891 A1 | 10/2013 | Slayton et al. |
| 2013/0294203 A1 | 11/2013 | Goodman et al. |
| 2013/0296697 A1 | 11/2013 | Slayton et al. |
| 2013/0296700 A1 | 11/2013 | Slayton et al. |
| 2013/0296743 A1 | 11/2013 | Lee et al. |
| 2013/0303904 A1 | 11/2013 | Barthe et al. |
| 2013/0303905 A1 | 11/2013 | Barthe et al. |
| 2013/0310714 A1 | 11/2013 | Eshel et al. |
| 2013/0310863 A1 | 11/2013 | Makin et al. |
| 2013/0345562 A1 | 12/2013 | Barthe et al. |
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |
| 2014/0155747 A1 | 6/2014 | Bennett |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |
| 2014/0236061 A1 | 8/2014 | Lee et al. |
| 2014/0243713 A1 | 8/2014 | Slayton et al. |
| 2014/0257145 A1 | 9/2014 | Emery |
| 2014/0276055 A1 | 9/2014 | Barthe et al. |
| 2014/0316269 A1 | 10/2014 | Zhang et al. |
| 2015/0000674 A1 | 1/2015 | Barthe et al. |
| 2015/0025420 A1 | 1/2015 | Slayton et al. |
| 2015/0031995 A1 | 1/2015 | Guracar |
| 2015/0064165 A1 | 3/2015 | Perry et al. |
| 2015/0080723 A1 | 3/2015 | Barthe et al. |
| 2015/0080771 A1 | 3/2015 | Barthe et al. |
| 2015/0080874 A1 | 3/2015 | Slayton et al. |
| 2015/0088182 A1 | 3/2015 | Slayton et al. |
| 2015/0141734 A1 | 5/2015 | Chapelon et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0238258 A1 | 8/2015 | Palero et al. |
| 2015/0297188 A1 | 10/2015 | Konofagou |
| 2015/0321026 A1 | 11/2015 | Branson et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0001097 A1 | 1/2016 | Cho et al. |
| 2016/0016015 A1 | 1/2016 | Slayton et al. |
| 2016/0027994 A1 | 1/2016 | Toda et al. |
| 2016/0151618 A1 | 6/2016 | Powers et al. |
| 2016/0158580 A1 | 6/2016 | Slayton et al. |
| 2016/0175619 A1 | 6/2016 | Lee et al. |
| 2016/0206335 A1 | 7/2016 | Slayton |
| 2016/0206341 A1 | 7/2016 | Slayton |
| 2016/0256675 A1 | 9/2016 | Slayton |
| 2016/0296769 A1 | 10/2016 | Barthe et al. |
| 2016/0310444 A1 | 10/2016 | Dobak, III |
| 2016/0361571 A1 | 12/2016 | Bernabei |
| 2016/0361572 A1 | 12/2016 | Slayton |
| 2017/0028227 A1 | 2/2017 | Emery et al. |
| 2017/0043190 A1 | 2/2017 | Barthe et al. |
| 2017/0050019 A1 | 2/2017 | Ron Edoute et al. |
| 2017/0080257 A1 | 3/2017 | Paunescu et al. |
| 2017/0090507 A1 | 3/2017 | Weiner et al. |
| 2017/0100585 A1 | 4/2017 | Hall et al. |
| 2017/0119345 A1 | 5/2017 | Levien et al. |
| 2017/0136263 A1 | 5/2017 | Reil |
| 2017/0209201 A1 | 7/2017 | Slayton et al. |
| 2017/0209202 A1 | 7/2017 | Friedrichs et al. |
| 2017/0304654 A1 | 10/2017 | Blanche et al. |
| 2017/0368574 A1 | 12/2017 | Sammoura |
| 2018/0001113 A1 | 1/2018 | Streeter |
| 2018/0015308 A1 | 1/2018 | Reed et al. |
| 2018/0043147 A1 | 2/2018 | Slayton |
| 2018/0099162 A1 | 4/2018 | Bernabei |
| 2018/0099163 A1 | 4/2018 | Bernabei |
| 2018/0126190 A1 | 5/2018 | Aviad et al. |
| 2018/0154184 A1 | 6/2018 | Kong et al. |
| 2018/0177912 A1 | 6/2018 | Kaioptas et al. |
| 2018/0207450 A1 | 7/2018 | Sanchez et al. |
| 2018/0272156 A1 | 9/2018 | Slayton et al. |
| 2018/0272157 A1 | 9/2018 | Barthe et al. |
| 2018/0272158 A1 | 9/2018 | Barthe et al. |
| 2018/0272159 A1 | 9/2018 | Slayton et al. |
| 2018/0317884 A1 | 11/2018 | Chapelon et al. |
| 2018/0333595 A1 | 11/2018 | Barthe et al. |
| 2018/0360420 A1 | 12/2018 | Vortman et al. |
| 2019/0000498 A1 | 1/2019 | Barthe et al. |

(56) References Cited

U.S. PATENT DOCUMENTS

| | | |
|---|---|---|
| 2019/0009110 A1 | 1/2019 | Gross et al. |
| 2019/0009111 A1 | 1/2019 | Myhr et al. |
| 2019/0022405 A1 | 1/2019 | Greenbaum et al. |
| 2019/0038921 A1 | 2/2019 | Domankevitz |
| 2019/0060675 A1 | 2/2019 | Krone et al. |
| 2019/0091490 A1 | 3/2019 | Alexander et al. |
| 2019/0142380 A1 | 5/2019 | Emery et al. |
| 2019/0143148 A1 | 5/2019 | Slayton |
| 2019/0184202 A1 | 6/2019 | Zereshkian et al. |
| 2019/0184203 A1 | 6/2019 | Slayton et al. |
| 2019/0184205 A1 | 6/2019 | Slayton et al. |
| 2019/0184207 A1 | 6/2019 | Barthe et al. |
| 2019/0184208 A1 | 6/2019 | Barthe et al. |
| 2019/0224501 A1 | 7/2019 | Burdette |
| 2019/0262634 A1 | 8/2019 | Barthe et al. |
| 2019/0282834 A1 | 9/2019 | Zawada et al. |
| 2019/0290939 A1 | 9/2019 | Watson et al. |
| 2019/0350562 A1 | 11/2019 | Slayton et al. |
| 2019/0366126 A1 | 12/2019 | Pahk et al. |
| 2019/0366127 A1 | 12/2019 | Emery |
| 2019/0366128 A1 | 12/2019 | Slayton et al. |
| 2020/0008779 A1 | 1/2020 | Göksel et al. |
| 2020/0094083 A1 | 3/2020 | Slayton et al. |
| 2020/0100762 A1 | 4/2020 | Barthe et al. |
| 2020/0129759 A1 | 4/2020 | Schwarz |
| 2020/0171330 A1 | 6/2020 | Barthe et al. |
| 2020/0179727 A1 | 6/2020 | Slayton et al. |
| 2020/0179729 A1 | 6/2020 | Slayton et al. |
| 2020/0188703 A1 | 6/2020 | Barthe et al. |
| 2020/0188704 A1 | 6/2020 | Barthe et al. |
| 2020/0188705 A1 | 6/2020 | Emery et al. |
| 2020/0206072 A1 | 7/2020 | Capelli et al. |
| 2020/0222728 A1 | 7/2020 | Khokhlova et al. |
| 2021/0038925 A1 | 2/2021 | Emery |
| 2021/0378630 A1 | 12/2021 | Slayton et al. |
| 2022/0006428 A1 | 1/2022 | Shepphard |
| 2024/0115885 A1 | 4/2024 | Slayton et al. |
| 2024/0198140 A1 | 6/2024 | Pooth et al. |
| 2024/0226961 A1 | 7/2024 | Brown et al. |

FOREIGN PATENT DOCUMENTS

| | | |
|---|---|---|
| CN | 102112059 | 6/2011 |
| CN | 102573648 | 7/2012 |
| CN | 104027893 | 9/2014 |
| CN | 106994041 | 8/2017 |
| CN | 108023552 | 5/2018 |
| DE | 4029175 | 3/1992 |
| DE | 10140064 | 3/2003 |
| DE | 10219297 | 11/2003 |
| DE | 10219217 | 12/2004 |
| DE | 20314479 | 12/2004 |
| EP | 0142215 | 5/1984 |
| EP | 0344773 | 12/1989 |
| EP | 1479412 | 11/1991 |
| EP | 0473553 | 4/1992 |
| EP | 670147 | 2/1995 |
| EP | 0661029 | 7/1995 |
| EP | 724894 | 2/1996 |
| EP | 763371 | 11/1996 |
| EP | 1044038 | 10/2000 |
| EP | 1050322 | 11/2000 |
| EP | 1234566 | 8/2002 |
| EP | 1262160 | 12/2002 |
| EP | 0659387 | 4/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1283690 | 11/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| EP | 2527828 | 11/2012 |
| EP | 2709726 | 11/2015 |
| EP | 1538980 | 1/2017 |
| EP | 3124047 | 1/2017 |
| EP | 2897547 | 11/2017 |
| EP | 2173261 B1 | 8/2018 |
| EP | 3417911 | 12/2018 |
| FR | 2532851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 3053069 | 10/1998 |
| JP | 11123226 | 5/1999 |
| JP | 11505440 | 5/1999 |
| JP | 11506636 | 6/1999 |
| JP | 10248850 | 9/1999 |
| JP | 2000126310 | 5/2000 |
| JP | 2000166940 | 6/2000 |
| JP | 2000233009 | 8/2000 |
| JP | 2001-46387 | 2/2001 |
| JP | 2001136599 A | 5/2001 |
| JP | 2001170068 | 6/2001 |
| JP | 2002505596 | 2/2002 |
| JP | 2002078764 | 3/2002 |
| JP | 2002515786 | 5/2002 |
| JP | 2002537013 | 5/2002 |
| JP | 2002521118 | 7/2002 |
| JP | 2002537939 | 11/2002 |
| JP | 2003-000592 | 1/2003 |
| JP | 2003050298 | 7/2003 |
| JP | 2003204982 | 7/2003 |
| JP | 2004-504898 | 2/2004 |
| JP | 2004-507280 | 3/2004 |
| JP | 2004154256 | 3/2004 |
| JP | 2004-509671 | 4/2004 |
| JP | 2004-512856 | 4/2004 |
| JP | 2004130145 | 4/2004 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2008515559 | 5/2008 |
| JP | 2009518126 | 5/2009 |
| JP | 2010517695 | 5/2010 |
| KR | 2001-0019317 | 3/2001 |
| KR | 1020010024871 | 3/2001 |
| KR | 2002-0038547 | 5/2002 |
| KR | 100400870 | 10/2003 |
| KR | 20060121267 | 11/2006 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 101027600 | 4/2011 |
| KR | 101075536 | 10/2011 |
| KR | 101075878 | 10/2011 |
| KR | 101118480 | 3/2012 |

(56) References Cited

FOREIGN PATENT DOCUMENTS

| | | |
|---|---|---|
| KR | 1020000059516 | 4/2012 |
| KR | 101154520 | 6/2012 |
| KR | 10-2013-0124598 | 11/2013 |
| KR | 10-1365946 | 2/2014 |
| TW | 386883 | 9/2000 |
| TW | 201208734 A | 3/2012 |
| WO | WO9312742 | 7/1993 |
| WO | WO9524159 | 9/1995 |
| WO | WO9625888 | 8/1996 |
| WO | WO9634568 | 11/1996 |
| WO | WO9639079 | 12/1996 |
| WO | WO9735518 | 10/1997 |
| WO | WO9832379 | 7/1998 |
| WO | WO9852465 | 11/1998 |
| WO | WO9933520 | 7/1999 |
| WO | WO9939677 | 8/1999 |
| WO | WO9949788 | 10/1999 |
| WO | WO200006032 | 2/2000 |
| WO | WO0015300 | 3/2000 |
| WO | WO0021612 | 4/2000 |
| WO | WO0048518 | 8/2000 |
| WO | WO0053113 | 9/2000 |
| WO | WO200071021 | 11/2000 |
| WO | WO0128623 | 4/2001 |
| WO | WO01045550 | 6/2001 |
| WO | WO0182777 | 11/2001 |
| WO | WO0182778 | 11/2001 |
| WO | WO0187161 | 11/2001 |
| WO | WO01080709 | 11/2001 |
| WO | WO2001087161 | 11/2001 |
| WO | WO0209812 | 2/2002 |
| WO | WO0209813 | 2/2002 |
| WO | WO02015768 | 2/2002 |
| WO | WO0224050 | 3/2002 |
| WO | WO200149194 | 7/2002 |
| WO | WO2002054018 | 7/2002 |
| WO | WO02092168 | 11/2002 |
| WO | WO03053266 | 7/2003 |
| WO | WO03065347 | 8/2003 |
| WO | WO03070105 | 8/2003 |
| WO | WO03077833 | 9/2003 |
| WO | WO03086215 | 10/2003 |
| WO | WO03096883 | 11/2003 |
| WO | WO03099177 | 12/2003 |
| WO | WO03099382 | 12/2003 |
| WO | WO03101530 | 12/2003 |
| WO | WO2004000116 | 12/2003 |
| WO | WO 2004035138 | 4/2004 |
| WO | WO2004080147 | 9/2004 |
| WO | WO2004110558 | 12/2004 |
| WO | WO2005/011804 | 2/2005 |
| WO | WO2005065408 | 7/2005 |
| WO | WO2005065409 | 7/2005 |
| WO | WO2005090978 | 9/2005 |
| WO | WO2005113068 | 12/2005 |
| WO | WO2006/042163 | 4/2006 |
| WO | WO2006036870 | 4/2006 |
| WO | WO2006042168 | 4/2006 |
| WO | WO2006042201 | 4/2006 |
| WO | WO2006065671 | 6/2006 |
| WO | WO2006082573 | 8/2006 |
| WO | WO2006104568 | 10/2006 |
| WO | WO2006110388 | 10/2006 |
| WO | WO2007067563 | 6/2007 |
| WO | WO2008036479 | 3/2008 |
| WO | WO2008036622 | 3/2008 |
| WO | WO2008144274 | 11/2008 |
| WO | WO2009013729 | 1/2009 |
| WO | WO2009149390 | 10/2009 |
| WO | WO2010006293 | 1/2010 |
| WO | WO2010102128 | 9/2010 |
| WO | WO2012134645 | 10/2012 |
| WO | WO2013048912 | 4/2013 |
| WO | WO2013178830 | 12/2013 |
| WO | WO2014043206 | 3/2014 |
| WO | WO2014045216 | 3/2014 |
| WO | WO2014055708 | 4/2014 |
| WO | WO2014057388 | 4/2014 |
| WO | WO2014127091 | 8/2014 |
| WO | WO2014137835 | 9/2014 |
| WO | WO2015160708 | 10/2015 |
| WO | WO2016054155 | 4/2016 |
| WO | WO2016115363 | 7/2016 |
| WO | WO2017127328 | 7/2017 |
| WO | WO2017149506 | 9/2017 |
| WO | WO2017165595 | 9/2017 |
| WO | WO 2017/212489 | 12/2017 |
| WO | WO2017223312 | 12/2017 |
| WO | WO2018035012 | 2/2018 |
| WO | WO2018158355 | 9/2018 |
| WO | WO2019008573 | 1/2019 |
| WO | WO 2019147596 | 8/2019 |
| WO | WO2019164836 | 8/2019 |
| WO | WO2020009324 | 1/2020 |
| WO | WO2020075906 | 4/2020 |
| WO | WO2020080730 | 4/2020 |
| WO | WO2020121307 | 6/2020 |
| WO | WO2022240843 | 11/2022 |
| WO | WO2024137052 | 6/2024 |

OTHER PUBLICATIONS

Adams et al., "High Intensity Focused Ultrasound Ablation of Rabbit Kidney Tumors" Sonablate High-Intensity Focused Ultrasound device; Journal of Endourology vol. 10, No. 1, (Feb. 1996).

Agren, Magnus S. et al., Collagenase in Wound Healing: Effect of Wound Age and Type. The Journal of Investigative Dermatology, vol. 99/No. 6, (Dec. 1992).

Alam, M., "The future of noninvasive procedural dermatology". Semin Cutan Med Surg. Mar. 2013; 32(1):59-61.

Alam, M., et al., "Ultrasound tightening of facial and neck skin: a rater-blinded prospective cohort study". J Am Acad Dermatol, 2010. 62(2): p. 262-9.

Alexiades-Armenakas, M., "Ultrasound Technologies for Dermatologic Techniques". J Drugs Derm. 2014. 12 (11): p. 1305.

Alster, T.S., et. al., "Noninvasive lifting of arm, thigh, and knee skin with transcutaneous intense focused ultrasound". Dermatol Surg, 2012. 38(5): p. 754-9.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Arosarena, O., "Options and Challenges for Facial Rejuvenation in Patients With Higher Fitzpatrick Skin Phototypes". JAMA Facial Plastic Surgery, 2015.

Arthur et al., "Non-invasive estimation of hyperthermia temperatures with ultrasound," Int. J. Hyperthermia, Sep. 2005, 21(6), pp. 589-600.

Barthe et al., "Ultrasound therapy system and ablation results utilizing miniature imaging/therapy arrays," Ultrasonics Symposium, 2004 IEEE, Aug. 23, 2004, pp. 1792-1795, vol. 3.

Bozec, Laurent et al., Thermal Denaturation Studies of Collagen by Microthermal Analysis and Atomic Force Microscopy, Biophysical Journal, vol. 101, pp. 228-236. (Jul. 2001).

Brobst, R.W., et. al., "Noninvasive Treatment of the Neck". Facial Plast Surg Clin North Am, 2014. 22(2): p. 191-202.

Brobst, R.W., et., al., "Ulthera: initial and six month results". Facial Plast Surg Clin North Am, 2012. 20(2): p. 163-76.

Brown J A et al: "Fabrication and performance of 40-60 MHz annular arrays", 2003 IEEE Ultrasonics Symposium Proceedings. Honolulu, Hawaii, Oct. 5-8, 2003; [IEEE Ultrasonics Symposium Proceedings], New York, NY: IEEE, US, vol. 1, Oct. 5, 2003 (Oct. 5, 2003), pp. 869-872.

Calderhead et al., "One Mechanism Behind LED Photo-Therapy for Wound Healing and Skin Rejuvenation: Key Role of the Mast Cell" Laser Therapy 17.3: 141-148 (2008).

Carruthers et al., "Consensus Recommendations for Combined Aesthetic Interventions in the Face Using Botulinum Toxin, Fillers, and Energy-Based Devices" Dermatol Surg 2016 (pp. 1-12).

(56) References Cited

OTHER PUBLICATIONS

Casabona, G., et. al., "Microfocused Ultrasound with Visualization and Calcium Hydroxylapatite for Improving Skin Laxity and Cellulite Appearance"; Plast Reconstr Surg Glob Open. Jul. 25, 2017;5(7):e1388, 8 pages.
Casabona, G., et. al., "Microfocused Ultrasound With Visualization and Fillers for Increased Neocollagenesis: Clinical and Histological Evaluation". Dermatol Surg 2014;40:S194-S198.
Chan, N.P., et al., "Safety study of transcutaneous focused ultrasound for non-invasive skin tightening in Asians". Lasers Surg Med, 2011. 43(5): p. 366-75.
Chapelon et al., "Effects of Cavitation in the High Intensity Therapeutic Ultrasound", Ultrasonics Symposium—1357 (1991).
Chapelon, et al., "Thresholds for Tissue Ablation by Focused Ultrasound" (1990).
Chen, L. et al., "Effect of Blood Perfusion on the ablation of liver parenchyma with high intensity focused ultrasound," Phys. Med. Biol; 38:1661-1673; 1993b.
Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.
Corry, Peter M., et al., "Human Cancer Treatment with Ultrasound", IEEE Transactions on Sonics and Ultrasonics, vol. SU-31, No. 5, Sep. 1984, pp. 444, 456.
Damianou et al., "Application of the Thermal Dose Concept for Predicting the Necrosed Tissue Volume During Ultrasound Surgery," 1993 IEEE Ultrasound Symposium, pp. 1199-1202.
Daum et al., Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.
Davis, Brian J., et al., "An Acoustic Phase Shift Technique for the Non-Invasive Measurement of Temperature Changes in Tissues", 1985 Ultrasonics Symposium, pp. 921-924.
Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Decolletage". Plast Reconstr Surg. Oct. 2014; 134(4 Suppl 1):123-4.
Decision of the Korean Intellectual Property Tribunal dated Jun. 28, 2013 regarding Korean Patent No. 10-1142108, which is related to the pending application and/or an application identified in the Table on pp. 1-4 of the Information Disclosure Statement herein (English translation, English translation certification, and Korean decision included).
Delon Martin, C., et al., "Venous Thrombosis Generation by Means of High-Intensity Focused Ultrasound" Ultrasound in Med. & Biol., vol. 21, No. 1, pp. 113-119 (1995).
Dierickx, Christine C., "The Role of Deep Heating for Noninvasive Skin Rejuvenation" Lasers in Surgery and Medicine 38:799-807 (2006).
Dobke, M.K., et al., "Tissue restructuring by energy-based surgical tools". Clin Plast Surg, 2012. 39(4): p. 399-408.
Dong, Yuan-Lin et al., "Effect of Ibuprofen on the Inflammatory Response to Surgical Wounds" The Journal of Trauma, vol. 35, No. 3. (1993).
Driller et al., "Therapeutic Applications of Ultrasound: A Review" IEEE Engineering in Medicine and Biology; (Dec. 1987) pp. 33-40.
Dvivedi, Sanjay, et al. "Effect of Ibuprofen and diclofenac sodium on experimental wound healing" Indian Journal of Experimental Biology, vol. 35, pp. 1243-1245. (Nov. 1997).
Fabi, S.G., "Microfocused Ultrasound With Visualization for Skin Tightening and Lifting: My Experience and a Review of the Literature". Dermatol Surg. Dec. 2014; 40 Suppl 12:S164-7.
Fabi, S.G., "Noninvasive skin tightening: focus on new ultrasound techniques". Clin Cosmet Investig Dermatol. Feb. 5, 2015; 8:47-52.
Fabi, S.G., et. al., "A prospective multicenter pilot study of the safety and efficacy of microfocused ultrasound with visualization for improving lines and wrinkles of the décolleté". Dermatol Surg. Mar. 2015; 41(3):327-35.
Fabi, S.G., et. al., "Evaluation of microfocused ultrasound with visualization for lifting, tightening, and wrinkle reduction of the decolletage". J Am Acad Dermatol, 2013. 69(6): p. 965-71.
Fabi, S.G., et. al., "Future directions in cutaneous laser surgery". Dermatol Clin, 2014. 32(1): p. 61-9.
Fabi, S.G., et. al., "Retrospective Evaluation of Micro-focused Ultrasound for Lifting and Tightening the Face and Neck". Dermatol Surg, 2014.
Friedmann D.P., "Comments on evaluation of microfocused ultrasound system for improving skin laxity and tightening in the lower face". Aesthet Surg J. Mar. 2015;35(3):NP81-2.
Friedmann, D.P., et. al., "Combination of intense pulsed light, Sculptra, and Ultherapy for treatment of the aging face". J Cosmet Dermatol, 2014. 13(2): p. 109-18.
Fry, W.J. et al., "Production of Focal Destructive Lesions in the Central Nervous System with Ultrasound," J. Neurosurg., 11:471-478; 1954.
Fujimoto, et al., "A New Cavitation Suppression Technique for Local Ablation Using High-Intensity Focused Ultrasound" Ultrasonics Symposium—1629 (1995).
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.
Gold, M.H., et. al., "Use of Micro-Focused Ultrasound with Visualization to Lift and Tighten Lax Knee Skin". J Cosmet Laser Ther, 2014: p. 1-15.
Goldberg, D.J., et. al., "Safety and Efficacy of Microfocused Ultrasound to Lift, Tighten, and Smooth the Buttocks". Dermatol Surg 2014; 40:1113-1117.
Greene, R.M., et al., "Skin tightening technologies". Facial Plast Surg. Feb. 2014; 30(1):62-7.
Greenhalgh, David G., "Wound healing and diabetes mellitus" Clinics in Plastic Surgery 30; 37-45. (2003).
Guo, S. et al., "Factors Affecting Wound Healing" Critical Reviews in Oral Biology & Medicine, J Dent Res 89(3), pp. 219-229. (2010).
Haar, G.R. et al., "Tissue Destruction with Focused Ultrasound in Vivo," Eur. Urol. 23 (suppl. 1):8-11; 1993.
Hantash, Basil M. et al., "Bipolar Fractional Radiofrequency Treatment Induces Neoelastogenesis and Neocollagenesis" Lasers in Surgery and Medicine 41:1-9 (2009).
Hantash, Basil M. et al., "In Vivo Histological Evaluation of a Novel Ablative Fractional Resurfacing Device" Lasers in Surgery and Medicine 39:96-107 (2007).
Harris, M.O., "Safety of Microfocused Ultrasound With Visualization in Patients With Fitzpatrick Skin Phototypes III to VI". JAMA Facial Plast. Surg, 2015.
Hart, et. al., "Current Concepts in the Use of PLLA: Clinical Synergy Noted with Combined Use of Microfocused Ultrasound and Poly-I-Lactic Acid on the Face, Neck, and Decolletage". Amer. Soc. Plast. Surg. 2015. 136; 180-187S.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Hexsel et al., "A Validated Photonumeric Cellulite Severity Scale"; J Eur Acad Dermatol Venereol. May 2009; 23(5):523-8, 6 pages.
Hitchcock, T.M. et. al., "Review of the safety profile for microfocused ultrasound with Visualization". Journal of Cosmetic Dermatology, 13, 329-335. (2014).
Husseini et al, "The Role of Cavitation in Acoustically Activated Drug Delivery," J. Control Release, Oct. 3, 2005, pp. 253-261, vol. 107(2).
Husseini et al. "Investigating the mechanism of acoustically activated uptake of drugs from Pluronic micelles," BMD Cancer 2002, 2:20k, Aug. 30, 2002, pp. 1-6.

(56) References Cited

OTHER PUBLICATIONS

Hynynen et al., Temperature Distributions During Local Ultrasound Induced Hyperthermia In Vivo, Ultrasonics Symposium—745 (1982).
Jeffers et al., "Evaluation of the Effect of Cavitation Activity on Drug-Ultrasound Synergisms," 1993 IEEE Ultrasonics Symposium, pp. 925-928.
Jenne, J., et al., "Temperature Mapping for High Energy US-Therapy", 1994 Ultrasonics Symposium, pp. 1879-1882.
Jeong, K.H., et al., "Neurologic complication associated with intense focused ultrasound". J Cosmet Laser Ther, 2013.
Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).
Ketterling J. A. et al.: "Design and fabrication of a 40-MHz annular array transducer", IEEE Transactions on Ultrasonics, Ferroelectrics and Frequency Control, IEEE, US, vol. 52, No. 4, Apr. 1, 2005 (Apr. 1, 2005), pp. 672-681.
Kim, H.J., et al., "Coagulation and ablation patterns of high-intensity focused ultrasound on a tissue mimicking phantom and cadaveric skin". Laser Med Sci. Sep. 4, 2015.
Kornstein, A.N., "Ulthera for silicone lip correction". Plast Reconstr Surg, 2012. 129(6): p. 1014e-1015e.
Kornstein, A.N., "Ultherapy shrinks nasal skin after rhinoplasty following failure of conservative measures". Plast Reconstr Surg, 2013. 131(4): p. 664e-6e.
Krischak, G.D., et al., "The effects of non-steroidal anti-inflammatory drug application on incisional wound healing in rats" Journal of Wound Care, vol. 6, No. 2, (Feb. 2007).
Laubach, H.J., et. al., "Confined Thermal Damage with Intense Ultrasound (IUS)" [abstr.] American Society for Laser Medicine and Surgery Abstracts, p. 15 #43 (Apr. 2006).
Laubach, H.J., et. al., "Intense focused ultrasound: evaluation of a new treatment modality for precise microcoagulation within the skin". Dermatol Surg, 2008. 34(5): p. 727-34.
Lee, H.J., et. al., "The efficacy and safety of intense focused ultrasound in the treatment of enlarged facial pores in Asian skin". J Dermatolog Treat, 2014.
Lee, H.S., et. al., "Multiple Pass Ultrasound Tightening of Skin Laxity of the Lower Face and Neck". Dermatol Surg, 2011.
Lin, Sung-Jan, et al., "Monitoring the thermally induced structural transitions of collagen by use of second-harmonic generation microscopy" Optics Letters, vol. 30, No. 6, (Mar. 15, 2005).
MacGregor J.L., et. al., "Microfocused Ultrasound for Skin Tightening". Semin Cutan Med Surg 32:18-25. (2013).
Madersbacher, S. et al., "Tissue Ablation in Benign Prostatic Hyperplasia with High Intensity Focused Ultrasound," Dur. Urol., 23 (suppl. 1):39-43; 1993.
Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.
Makin et al, "Confirmed Bulk Ablation and Therapy Monitoring Using Intracorporeal Image-Treat Ultrasound Arrays," 4th International Symposium on Therapeutic Ultrasound, Sep. 19, 2004.
Makin et al., "Miniaturized Ultrasound Arrays for Interstitial Ablation and Imaging," UltraSound Med. Biol. 2005, Nov. 1, 2005, pp. 1539-1550, vol. 31(11).
Manohar et al, "Photoacoustic mammography laboratory prototype: imaging of breast tissue phantoms," Journal of Biomedical Optics, Nov./Dec. 2004, pp. 1172-1181, vol. 9, No. 6.
Mast et al, "Bulk Ablation of Soft Tissue with Intense Ultrasound; Modeling and Experiments," J. Acoust. Soc. Am., Oct. 1, 2005, pp. 2715-2724, vol. 118(4).
Meshkinpour, Azin, et al., "Treatment of Hypertrophic Scars and Keloids With a Radiofrequency Device: A Study of Collagen Effects" Lasers in Surgery and Medicine 37:343-349 (2005).
Microchip microID 125 KHz RFID System Design Guide, Microchip Technology Inc. (2004).
Minkis, K., et. al., "Ultrasound skin tightening". Dermatol Clin, 2014. 32(1): p. 71-7.
Mitragotri, S., "Healing sound: the use of ultrasound in drug delivery and other therapeutic applications," Nature Reviews; Drug Delivery, pp. 255-260, vol. 4 (Mar. 2005).
Mosser, David M. et al., "Exploring the full spectrum of macrophage activation" Nat Rev Immunol; 8(12): 958-969. (Dec. 2008).
Murota, Sei-Itsu, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).
Murota, Sei-Itsu, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).
Nestor, M.S. et. al., "Safety and Efficacy of Micro-focused Ultrasound Plus Visualization for the Treatment of Axillary Hyperhidrosis". J Clin Aesthet Dermatol, 2014. 7(4): p. 14-21.
Oni, G., et. al. "Response to 'comments on evaluation of microfocused ultrasound system for improving skin laxity and tightening in the lower face'". Aesthet Surg J. Mar. 2015;35(3):NP83-4.
Oni, G., et. al., "Evaluation of a Microfocused Ultrasound System for Improving Skin Laxity and Tightening in the Lower Face". Aesthet Surg J, 2014. 38:861-868.
Pak, C.S., et. al., "Safety and Efficacy of Ulthera in the Rejuvenation of Aging Lower Eyelids: A Pivotal Clinical Trial". Aesthetic Plast Surg, 2014.
Paradossi et al., "Poly(vinyl alcohol) as versatile biomaterial for potential biomedical applications," Journal of Materials Science: Materials in Medicine, 2003, pp. 687-691, vol. 14.
Pritzker, R.N., et. al, "Updates in noninvasive and minimally invasive skin tightening". Semin Cutan Med Surg. Dec. 2014;33(4):182-7.
Pritzker, R.N., et. al., "Comparison of different technologies for noninvasive skin tightening". Journal of Cosmetic Dermatology, 13, 315-323. (2014).
Rappolee, Daniel A., et al., "Wound Macrophages Express TGF and Other Growth Factors in Vivo: Analysis by mRNA Phenotyping" Science, vol. 241, No. 4866 (Aug. 1988).
Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.
Righetti et al, "Elastographic Characterization of HIFU-Induced Lesions in Canine Livers," 1999, Ultrasound in Med & Bio, vol. 25, No. 7, pp. 1099-1113.
Rokhsar, C., et. al., "Safety and efficacy of microfocused ultrasound in tightening of lax elbow skin". Dermatol Surg. 2015; 41(7):821-6.
Rosenberg, Carol S. "Wound Healing in the Patient with Diabetes Mellitus" Nursing Clinics of North America, vol. 25, No. 1, (Mar. 1990).
Saad et al., "Ultrasound-Enhanced Effects of Adriamycin Against Murine Tumors," Ultrasound in Med. & Biol. vol. 18, No. 8, pp. 715-723 (1992).
Sabet-Peyman, E.J. et. al., "Complications Using Intense Ultrasound Therapy to Treat Deep Dermal Facial Skin and Subcutaneous Tissues". Dermatol Surg 2014; 40:1108-1112.
Sandulache, Vlad C. et al., "Prostaglandin E2 inhibition of keloid fibroblast migration, contraction, and transforming growth factor (TGF)-B1-induced collagen synthesis" Wound Rep Reg 15 122-133, 2007. (2007).
Sanghvi, N.T., et al., "Transrectal Ablation of Prostate Tissue Using Focused Ultrasound," 1993 Ultrasonics Symposium, IEEE, pp. 1207-1210.
Sasaki, G.H. et. al., "Clinical Efficacy and Safety of Focused-Image Ultrasonography: A 2-Year Experience". Aesthet Surg J, 2012.
Sasaki, G.H. et. al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.

(56) References Cited

OTHER PUBLICATIONS

Sassen, Sander, "ATI's R520 architecture, the new king of the hill?" http://www.hardwareanalysis.com/content/article/1813, Sep. 16, 2005, 2 pages.
Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.
Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Simon et al., "Applications of Lipid-Coated Microbubble Ultrasonic Contrast to Tumor Therapy," Ultrasound in Med. & Biol. vol. 19, No. 2, pp. 123-125 (1993).
Sklar, L.R., et. al., "Use of transcutaneous ultrasound for lipolysis and skin tightening: a review". Aesthetic Plast Surg, 2014. 38(2): p. 429-41.
Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.
Sonocare, Inc. Therapeutic Ultrasound System Model CST-100 Instruction Manual (1985).
Suh, D.H., et. al., "A intense-focused ultrasound tightening for the treatment of infraorbital laxity". J Cosmet Laser Ther, 2012. 14(6): p. 290-5.
Suh, D.H., et. al., "Comparative histometric analysis of the effects of high-intensity focused ultrasound and radiofrequency on skin". J Cosmet Laser Ther. Mar. 24, 2015:1-7.
Suh, D.H., et. al., "Intense Focused Ultrasound Tightening in Asian Skin: Clinical and Pathologic Results" American Society for Dermatologic Surgery, Inc.; 37:1595-1602. (2011).
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectrometry," Proceedings of the National Academy of Sciences of USA, National Academy of Science, Washington, DC, vol. 101, No. 26, Jun. 29, 2004, pp. 9528-9533.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions," American Chemical Society, Phys. Chem. 1992, 96, pp. 3548-3555.
Ueno, S., et al., "Ultrasound Thermometry in Hyperthermia", 1990 Ultrasonic Symposium, pp. 1645-1652.
Verhofstad, Michiel H.J. et al., "Collagen Synthesis in rat skin and ileum fibroblasts is affected differently by diabetes-related factors" Int. J. Exp. Path. (1998), 79, 321-328.
Wang, H., et al., "Limits on Focused Ultrasound for Deep Hyperthermia", 1994 Ultrasonic Symposium, Nov. 1-4, 1994, pp. 1869-1872, vol. 3.
Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.
Webster et al. "The role of ultrasound-induced cavitation in the 'in vitro' stimulation of collagen synthesis in human fibroblasts"; Ultrasonics pp. 33-37(Jan. 1980).
Weiss, M., "Commentary: noninvasive skin tightening: ultrasound and other technologies: where are we in 2011?" Dermatol Surg, 2012. 38(1): p. 28-30.
White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1 (pp. 22-29).
White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).
White, W. Matthew, et al., "Selective Transcutaneous Delivery of Energy to Porcine Soft Tissues Using Intense Ultrasound (IUS)" Lasers in Surgery and Medicine 40:67-75 (2008).
Woodward, J.A., et. al. "Safety and Efficacy of Combining Microfocused Ultrasound With Fractional CO2 Laser Resurfacing for Lifting and Tightening the Face and Neck". Dermatol Surg, Dec. 2014 40:S190-S193.
Zelickson, Brian D. et al., "Histological and Ultrastructural Evaluation of the Effects of a Radiofrequency-Based Nonablative Dermal Remodeling Device, A Pilot Study" Arch Dermatol, vol. 140, (Feb. 2004).
PCT/US2020/41783 International Search Report mailed Oct. 7, 2020, 19 pages.
U.S. Appl. No. 12/996,616, filed Jan. 12, 2011, Hand Wand for Ultrasonic Cosmetic Treatment and Imaging.
U.S. Appl. No. 16/703,019, filed Dec. 6, 2019, System and Method for Ultrasound Treatment.
U.S. Appl. No. 17/410,780, filed Aug. 24, 2021, Systems for Ultrasound Treatment.
U.S. Appl. No. 13/245,822, filed Sep. 26, 2011, System and Method for Cosmetic Treatment.
U.S. Appl. No. 13/245,852, filed Sep. 26, 2011, Systems for Cosmetic Treatment.
U.S. Appl. No. 13/245,864, filed Sep. 27, 2011, Methods for Non-Invasive Cosmetic Treatment of the Eye Region.
U.S. Appl. No. 13/246,117, filed Sep. 27, 2011, Methods for Non-Invasive Lifting and Tightening of the Lower Face and Neck.
U.S. Appl. No. 13/246,112, filed Sep. 27, 2011, Tissue Imaging and Treatment Method.
U.S. Appl. No. 14/193,234, filed Feb. 28, 2014, Devices and Methods for Multi-Focus Ultrasound Therapy.
U.S. Appl. No. 16/541,476, filed Aug. 15, 2019, Devices and Methods for Multi-Focus Ultrasound Therapy.
U.S. Appl. No. 15/302,436, filed Oct. 6, 2016, Band Transducer Ultrasound Therapy.
U.S. Appl. No. 15/855,949, filed Dec. 27, 2017, Band Transducer Ultrasound Therapy.
U.S. Appl. No. 16/797,393, filed Feb. 21, 2020, Band Transducer Ultrasound Therapy.
U.S. Appl. No. 15/562,384, filed Oct. 27, 2017, Systems and Methods for Cosmetic Ultrasound Treatment of Skin.
U.S. Appl. No. 16/069,319, filed Jul. 11, 2018, Compact ultrasound device having annular ultrasound array peripherally electrically connected to flexible printed circuit board and method of assembly thereof.
U.S. Appl. No. 16/964,914, filed Jul. 24, 2020, Systems and Methods for Simultaneous Multi-Focus Ultrasound Therapy in Multiple Dimensions.
U.S. Appl. No. 16/970,772, filed Aug. 18, 2020, Systems and Methods for Combined Cosmetic Treatment of Cellulite With Ultrasound.
U.S. Appl. No. 17/297,145, filed May 26, 2021, Systems and Methods for Enhancing Efficacy of Ultrasound Treatment.
U.S. Appl. No. 08/950,353, filed Oct. 14, 1997, Imaging, Theragy and Temperature Monitoring Ultrasonic System.
U.S. Appl. No. 09/502,174, filed Feb. 10, 2000, Imaging, Therapy and Temperature Monitoring Ultrasonic System.
U.S. Appl. No. 10/193,419, filed Jul. 10, 2002, Imaging, Therapy and Temperature Monitoring Ultrasonic System.
U.S. Appl. No. 10/944,499, filed Sep. 16, 2004, Method and System for Ultrasound Treatment With a Multi-Directional Transducer.
U.S. Appl. No. 11/163,177, filed Oct. 7, 2005, Method and System for Treating Acne and Sebaceous Glands.
U.S. Appl. No. 10/950,112, filed Sep. 24, 2004, Method and System for Combined Ultrasound Treatment.
U.S. Appl. No. 11/163,178, filed Oct. 7, 2005, Method and System for Treating Stretch Marks.
U.S. Appl. No. 11/245,999, filed Oct. 6, 2005, System and Method for Ultra-High Frequency Ultrasound Treatment.
U.S. Appl. No. 10/944,500, filed Sep. 16, 2004, System and Method for Variable Depth Ultrasound Treatment.
U.S. Appl. No. 11/744,655, filed May 4, 2007, Imaging, Therapy and Temperature Monitoring Ultrasonic System.

(56) References Cited

OTHER PUBLICATIONS

U.S. Appl. No. 13/937,190, filed Jul. 8, 2013, Imaging, Therapy and Temperature Monitoring Ultrasonic System.
U.S. Appl. No. 12/135,962, filed Jun. 9, 2008, Method and System for Ultrasound Treatment With a Multi-Directional Transducer.
U.S. Appl. No. 12/792,934, filed Jun. 3, 2010, System and Method for Ultra-High Freguency Ultrasound Treatment.
U.S. Appl. No. 13/914,945, filed Jun. 11, 2013, System and Method for Ultra-High Frequency Ultrasound Treatment.
U.S. Appl. No. 12/834,754, filed Jul. 12, 2010, System and Method for Variable Depth Ultrasound Treatment.
U.S. Appl. No. 14/264,732, filed Apr. 29, 2014, System and Method for Variable Depth Ultrasound Treatment.
U.S. Appl. No. 11/126,760, filed May 11, 2005, Method and System for Three-Dimensional Scanning and Imaging.
U.S. Appl. No. 13/564,552, filed Aug. 1, 2012, Method and System for Controlled Scanning, Imaging and/or Therapy.
U.S. Appl. No. 12/437,726, filed May 8, 2009, Method and System for Combined Ultrasound Treatment.
U.S. Appl. No. 11/163,148, filed Oct. 6, 2005, Method and System for Controlled Thermal Injury of Human Superficial Tissue.
U.S. Appl. No. 13/444,688, filed Apr. 11, 2012, Customized Cosmetic Treatment.
U.S. Appl. No. 16/427,969, filed May 31, 2019, Customized Cosmetic Treatment.
U.S. Appl. No. 11/163,152, filed Oct. 6, 2005, Method and System for Treatment of Sweat Glands.
U.S. Appl. No. 13/444,485, filed Apr. 11, 2012, Methods for Treatment of Sweat Glands.
U.S. Appl. No. 13/603,159, filed Sep. 4, 2012, Methods for Treatment of Hyperhidrosis.
U.S. Appl. No. 13/603,279, filed Sep. 4, 2012, Energy Based Hyperhidrosis Treatment.
U.S. Appl. No. 13/950,728, filed Jul. 25, 2013, Energy Based Hyperhidrosis Treatment.
U.S. Appl. No. 14/571,835, filed Dec. 16, 2014, Energy Based Hyperhidrosis Treatment.
U.S. Appl. No. 15/243,081, filed Aug. 22, 2016, Energy Based Hyperhidrosis Treatment.
U.S. Appl. No. 16/049,364, filed Jul. 30, 2018, Energy Based Hyperhidrosis Treatment.
U.S. Appl. No. 17/209,808, filed Mar. 23, 2021, Energy Based Skin Gland Treatment.
U.S. Appl. No. 11/163,151, filed Oct. 6, 2005, Method and System for Noninvasive Face Lifts and Deep Tissue Tightening.
U.S. Appl. No. 13/444,336, filed Apr. 11, 2012, Treatment of Sub-Dermal Regions for Cosmetic Effects.
U.S. Appl. No. 13/679,430, filed Nov. 16, 2012, Ultrasound Treatment of Sub-Dermal Tissue for Cosmetic Effects.
U.S. Appl. No. 13/924,376, filed Jun. 21, 2013, Noninvasive Tissue Tightening for Cosmetic Effects.
U.S. Appl. No. 13/924,355, filed Jun. 21, 2013, Noninvasive Aesthetic Treatment for Tightening Tissue.
U.S. Appl. No. 13/924,323, filed Jun. 21, 2013, Energy-Based Tissue Tightening.
U.S. Appl. No. 14/200,852, filed Mar. 7, 2014, Noninvasive Tissue Tightening System.
U.S. Appl. No. 14/200,961, filed Mar. 7, 2014, Energy-Based Tissue Tightening System.
U.S. Appl. No. 16/543,137, filed Aug. 16, 2019, Noninvasive Tissue Tightening System.
U.S. Appl. No. 12/028,636, filed Feb. 8, 2008, Method and System for Noninvasive Face Lifts and Deep Tissue Tightening.
U.S. Appl. No. 13/964,820, filed Aug. 12, 2013, Methods for Noninvasive Skin Tightening.
U.S. Appl. No. 14/201,256, filed Mar. 7, 2014, System for Noninvasive Skin Tightening.
U.S. Appl. No. 15/098,139, Apr. 13, 2016, System and Method for Noninvasive Skin Tightening.
U.S. Appl. No. 15/958,939, filed Apr. 20, 2018, System and Method for Noninvasive Skin Tightening.
U.S. Appl. No. 16/698,122, filed Nov. 27, 2019, System and Method for Noninvasive Skin Tightening.
U.S. Appl. No. 17/209,912, filed Mar. 23, 2021, System and Method for Noninvasive Skin Tightening.
U.S. Appl. No. 14/685,390, filed Apr. 13, 2015, Energy-Based Tissue Tightening System.
U.S. Appl. No. 11/163,150, filed Oct. 6, 2005, Method and System for Photoaged Tissue.
U.S. Appl. No. 13/230,498, filed Sep. 12, 2011, Method and System for Photoaged Tissue.
U.S. Appl. No. 14/169,709, filed Jan. 31, 2014, Methods for Treating Skin Laxity.
U.S. Appl. No. 14/692,114, filed Apr. 21, 2015, Systems for Treating Skin Laxity.
U.S. Appl. No. 15/248,407, filed Aug. 26, 2016, Systems for Treating Skin Laxity.
U.S. Appl. No. 15/625,700, filed Jun. 16, 2017, Systems for Treating Skin Laxity.
U.S. Appl. No. 15/821,070, filed Nov. 22, 2017, Ultrasound Probe for Treating Skin Laxity.
U.S. Appl. No. 15/996,255, filed Jun. 1, 2018, Ultrasound Probe for Treating Skin Laxity.
U.S. Appl. No. 16/284,907, filed Feb. 25, 2019, Ultrasound Probe for Treating Skin Laxity.
U.S. Appl. No. 16/797,362, filed Feb. 21, 2020, Ultrasound Probe for Treating Skin Laxity.
U.S. Appl. No. 17/127,721, filed Dec. 18, 2020, Ultrasound Probe for Treating Skin Laxity.
U.S. Appl. No. 11/163,176, filed Oct. 7, 2005, Method and System for Treating Blood Vessel Disorders.
U.S. Appl. No. 13/601,742, filed Aug. 31, 2012, Method and System for Treating Blood Vessel Disorders.
U.S. Appl. No. 12/574,512, filed Oct. 6, 2009, Method and System for Treating Stretch Marks.
U.S. Appl. No. 14/554,668, filed Nov. 26, 2014, Method and System for Treating Stretch Marks.
U.S. Appl. No. 15/260,825, filed Sep. 12, 2016, Method and System for Ultrasound Treatment of Skin.
U.S. Appl. No. 15/625,818, filed Jun. 16, 2017, Method and System for Ultrasound Treatment of Skin.
U.S. Appl. No. 15/829,182, filed Dec. 1, 2017, Ultrasound Probe for Treatment of Skin.
U.S. Appl. No. 15/996,263, filed Jun. 1, 2018, Ultrasound Probe for Treatment of Skin.
U.S. Appl. No. 16/284,920, filed Feb. 25, 2019, Ultrasound Probe for Treatment of Skin.
U.S. Appl. No. 16/797,387, filed Feb. 21, 2020, Ultrasound Probe for Treatment of Skin.
U.S. Appl. No. 17/495,741, filed Oct. 6, 2021, Ultrasound Probe for Treatment of Skin.
U.S. Appl. No. 11/857,989, filed Sep. 19, 2007, Method and System for Treating Muscle, Tendon, Ligament and Cartilage Tissue.
U.S. Appl. No. 13/494,856, filed Jun. 12, 2012, Method and System for Treating Muscle, Tendon, Ligament and Cartilage Tissue.
U.S. Appl. No. 13/835,635, filed Mar. 15, 2013, Methods for Face and Neck Lifts.
U.S. Appl. No. 13/965,741, filed Aug. 13, 2013, Methods for Preheating Tissue for Cosmetic Treatment of the Face and Body.
U.S. Appl. No. 14/740,092, filed Jun. 15, 2015, Methods for Rejuvenating Skin by Heating Tissue for Cosmetic Treatment of the Face and Body.
U.S. Appl. No. 15/862,400, filed Jan. 4, 2018, Rejuvenating Skin by Heating Tissue for Cosmetic Treatment of the Face and Body.
U.S. Appl. No. 16/409,678, filed May 10, 2019, Rejuvenating Skin by Heating Tissue for Cosmetic Treatment of the Face and Body.
U.S. Appl. No. 17/081,754, filed Oct. 27, 2020, Rejuvenating Skin by Heating Tissue for Cosmetic Treatment of the Face and Body.
U.S. Appl. No. 14/628,198, filed Feb. 20, 2015, System and Method for Treating Cartilage and Injuries to Joints and Connective Tissue.
U.S. Appl. No. 14/554,571, filed Nov. 26, 2014, Methods for Face and Neck Lifts.

(56) References Cited

OTHER PUBLICATIONS

U.S. Appl. No. 15/248,454, filed Aug. 26, 2016, Methods for Face and Neck Lifts.
U.S. Appl. No. 16/049,293, filed Jul. 30, 2018, Methods for Face and Neck Lifts.
U.S. Appl. No. 16/697,970, filed Nov. 27, 2019, Methods for Lifting Skin Tissue.
U.S. Appl. No. 12/954,484, filed Nov. 24, 2010, Methods and Systems for Generating Thermal Bubbles for Improved Ultrasound Imaging and Therapy.
U.S. Appl. No. 12/350,383, filed Jan. 8, 2009, Method and System for Treating Acne and Sebaceous Glands.
U.S. Appl. No. 12/116,845, filed May 7, 2008, Method and System for Combined Energy Profile.
U.S. Appl. No. 14/643,749, filed Mar. 10, 2015, Method and System for Combined Energy Profile.
U.S. Appl. No. 08/766,083, filed Dec. 16, 1996, Method and Apparatus for Surface Ultrasound Imaging.
U.S. Appl. No. 09/113,227, filed Jul. 10, 1998, Method and Apparatus for Three Dimensional Ultrasound Imaging.
U.S. Appl. No. 08/944,261, filed Oct. 6, 1997, Wideband Acoustic Transducer.
U.S. Appl. No. 09/434,078, filed Nov. 5, 1999, Method and Apparatus for Three Dimensional Ultrasound Imaging.
U.S. Appl. No. 09/523,890, filed Mar. 13, 2000, Method and Apparatus for Three Dimensional Ultrasound Imaging.
U.S. Appl. No. 09/419,543, filed Oct. 18, 1999, Peripheral Ultrasound Imaging System.
U.S. Appl. No. 09/750,816, filed Dec. 28, 2000, Visual Imaging System for Ultrasonic Probe.
U.S. Appl. No. 10/358,110, filed Feb. 4, 2003, Visual Imaging System for Ultrasonic Probe.
U.S. Appl. No. 11/380,161, filed Apr. 25, 2006, Method and System for Enhancing Computer Peripheral Safety.
U.S. Appl. No. 11/554,272, filed Oct. 30, 2006, Visual Imaging System for Ultrasonic Probe.
U.S. Appl. No. 13/071,298, filed Mar. 24, 2011, Visual Imaging System for Ultrasonic Probe.
U.S. Appl. No. 13/854,936, filed Mar. 25, 2013, Visual Imaging System for Ultrasonic Probe.
U.S. Appl. No. 12/509,254, filed Jul. 24, 2009, Method and System for Enhancing Computer Peripheral Safety.
U.S. Appl. No. 13/453,847, filed Apr. 23, 2012, Method and System for Enhancing Computer Peripheral Safety.
U.S. Appl. No. 11/538,794, filed Oct. 4, 2006, Ultrasound System and Method for Imaging and/or Measuring Displacement of Moving Tissue and Fluid.
U.S. Appl. No. 09/502,175, filed Feb. 10, 2000, Method and Apparatus for Safely Delivering Medicants to a Region of Tissue, Using Imaging, Therapy and Temperature Monitoring.
U.S. Appl. No. 08/943,728, filed Oct. 3, 1997, Method and Apparatus for Safely Delivering Medicants to a Region of Tissue Using Ultrasound.
U.S. Appl. No. 12/415,945, filed Mar. 31, 2009, Method and System for Noninvasive Mastopexy.
U.S. Appl. No. 11/163,155, filed Oct. 6, 2005, Method and System for Noninvasive Mastopexy.
U.S. Appl. No. 11/163,154, filed Oct. 6, 2005, Method and System for Treatment of Cellulite.
U.S. Appl. No. 13/356,405, filed Jan. 23, 2012, Method and System for Treatment of Cellulite.
U.S. Appl. No. 13/789,562, filed Mar. 7, 2013, Method and System for Ultrasound Treatment of Fat.
U.S. Appl. No. 14/164,598, filed Jan. 27, 2013, Method for Fat and Cellulite Reduction.
U.S. Appl. No. 14/550,720, filed Nov. 21, 2014, System and Method for Fat and Cellulite Reduction.
U.S. Appl. No. 15/041,829, filed Feb. 11, 2016, System and Method for Fat and Cellulite Reduction.
U.S. Appl. No. 15/374,918, filed Dec. 9, 2016, System and Method for Fat and Cellulite Reduction.
U.S. Appl. No. 15/650,246, filed Jul. 14, 2017, System and Method for Fat and Cellulite Reduction.
U.S. Appl. No. 15/821,281, filed Nov. 22, 2017, Ultrasound Probe for Fat and Cellulite Reduction.
U.S. Appl. No. 15/996,295, filed Jun. 1, 2018, Ultrasound Probe for Fat and Cellulite Reduction.
U.S. Appl. No. 16/272,453, filed Feb. 11, 2019, Ultrasound Probe for Tissue Treatment.
U.S. Appl. No. 16/794,717, filed Feb. 19, 2020, Ultrasound Probe for Tissue Treatment.
U.S. Appl. No. 17/127,705, filed Dec. 18, 2020, Ultrasound Probe for Tissue Treatment.
U.S. Appl. No. 11/738,682, filed Apr. 23, 2007, Method and System for Non-Ablative Acne Treatment and Prevention.
U.S. Appl. No. 12/116,810, filed May 7, 2008, Methods and Systems for Modulating Medicants Using Acoustic Energy.
U.S. Appl. No. 12/116,828, filed May 7, 2008, Methods and Systems for Coupling and Focusing Acoustic Energy Using a Coupler Member.
U.S. Appl. No. 12/646,609, filed Dec. 23, 2009, Methods and System for Fat Reduction and/or Cellulite Treatment.
U.S. Appl. No. 14/192,520, filed Feb. 27, 2014, Energy Based Fat Reduction.
U.S. Appl. No. 14/550,772, filed Nov. 21, 2014, Energy Based Fat Reduction.
U.S. Appl. No. 15/401,804, filed Feb. 11, 2016, Energy Based Fat Reduction.
U.S. Appl. No. 15/380,267, filed Dec. 15, 2016, Energy Based Fat Reduction.
U.S. Appl. No. 15/650,525, filed Jul. 18, 2017, Energy Based Fat Reduction.
U.S. Appl. No. 15/829,175, filed Dec. 1, 2017, Energy Based Fat Reduction.
U.S. Appl. No. 15/996,249, filed Jun. 1, 2018, Energy Based Fat Reduction.
U.S. Appl. No. 16/272,427, filed Feb. 11, 2019, Energy Based Fat Reduction.
U.S. Appl. No. 16/794,701, filed Feb. 19, 2020, Energy Based Fat Reduction.
U.S. Appl. No. 17/127,691, filed Dec. 18, 2020, Energy Based Fat Reduction.
U.S. Appl. No. 13/291,312, filed Nov. 11, 2011, Devices and Methods for Acoustic Shielding.
U.S. Appl. No. 14/487,504, filed Sep. 16, 2014, Devices and Methods for Acoustic Shielding.
U.S. Appl. No. 13/136,538, filed Aug. 2, 2011, Systems and Methods for Treating Acute and/or Chronic Injuries in Soft Tissue.
U.S. Appl. No. 13/136,542, filed Aug. 2, 2011, System and Method for Treating Cartilage.
U.S. Appl. No. 13/163,541, filed Aug. 2, 2011, Methods and Systems for Treating Plantar Fascia.
U.S. Appl. No. 13/136,544, filed Aug. 2, 2011, Systems and Methods for Ultrasound Treatment.
U.S. Appl. No. 13/547,023, filed Jul. 11, 2012, Systems and Methods for Coupling an Ultrasound Source to Tissue.
U.S. Appl. No. 13/545,931, filed Jul. 10, 2012, Methods and Systems for Controlling Acoustic Energy Deposition Into a Medium.
U.S. Appl. No. 13/545,953, filed Jul. 10, 2012, Systems and Methods for Accelerating Healing of Implanted Material and/or Native Tissue.
U.S. Appl. No. 13/547,011, filed Jul. 11, 2012, Systems and Methods for Monitoring and Controlling Ultrasound Power Output and Stability.
U.S. Appl. No. 13/545,954, filed Jul. 10, 2012, Systems and Methods for Improving an Outside Appearance of Skin Using Ultrasound as an Energy Source.
U.S. Appl. No. 13/545,945, filed Jul. 10, 2012, Systems and Methods for Treating Injuries to Joints and Connective Tissue.
U.S. Appl. No. 13/545,929, filed Jul. 10, 2012, Methods and Systems for Ultrasound Treatment.

(56) References Cited

OTHER PUBLICATIONS

U.S. Appl. No. 13/863,249, filed Apr. 15, 2013, Systems for Cosmetic Treatment.
U.S. Appl. No. 13/863,281, filed Apr. 15, 2013, Methods for Non-invasive Cosmetic Treatment.
U.S. Appl. No. 14/847,626, filed Sep. 8, 2015, Systems for Cosmetic Treatment.
U.S. Appl. No. 13/863,362, filed Apr. 15, 2013, Thick Film Transducer Arrays.
U.S. Appl. No. 14/217,110, filed Mar. 17, 2014, Ultrasound Treatment Device and Method of Use.
U.S. Appl. No. 14/217,382, filed Mar. 17, 2014, Ultrasound Treatment Device and Method of Use.
U.S. Appl. No. 14/225,189, filed Mar. 25, 2014, Reflective Ultrasound Technology for Dermatological Treatments.
U.S. Appl. No. 15/345,908, filed Nov. 8, 2016, Reflective Ultrasound Technology for Dermatological Treatments.
U.S. Appl. No. 15/719,377, filed Sep. 28, 2017, Reflective Ultrasound Technology for Dermatological Treatments.
U.S. Appl. No. 14/270,859, filed May 6, 2014, Methods and Systems for Generating Thermal Bubbles for Improved Ultrasound Imaging and Therapy.
U.S. Appl. No. 14/679,494, filed Apr. 6, 2015, Methods and Systems for Generating Thermal Bubbles for Improved Ultrasound Imaging and Therapy.
U.S. Appl. No. 14/405,368, filed Dec. 3, 2014, Devices and Methods for Ultrasound Focal Depth Control.
U.S. Appl. No. 14/568,954, filed Dec. 12, 2014, System and Method for Cosmetic Enhancement of Lips.
U.S. Appl. No. 14/569,001, filed Dec. 12, 2014, System and Method for Non-Invasive Treatment With Improved Efficiency.
U.S. Appl. No. 14/600,782, filed Jan. 20, 2015, Methods and Systems for Controlling and Acoustic Energy Deposition in Various Media.
U.S. Appl. No. 14/738,420, filed Jun. 12, 2015, Systems and Methods for Fast Ultrasound Treatment.
U.S. Appl. No. 14/751,349, filed Jun. 26, 2015, Methods and Systems for Tattoo Removal.
U.S. Appl. No. 15/001,712, filed Jan. 20, 2016, Methods and Systems for Removal of a Targeted Tissue from a Body.
U.S. Appl. No. 15/001,621, filed Jan. 20, 2016, Methods and Systems for Removal of a Foreign Object from Tissue.
U.S. Appl. No. 15/059,773, filed Mar. 3, 2016, Methods and Systems for Material Transport Across an Impermeable or Semi-Permeable Membrane Via Artificially Created Microchannels.
U.S. Appl. No. 15/094,774, filed Apr. 8, 2016, System and Method for Increased Control of Ultrasound Treatments.
Gottlieb et al., Development of a high-frequency (> 50 MHz) copolymer annular-array, ultrasound transducer, IEEE Trans Ultrasonics, and Frequency Control, May 2006;53(5):1037-45.
Narayanasamy et al., "Spatial registration of temporally separated whole breast 3D ultrasound images" Med Phys. Sep. 2009;36(9):4288-300. doi: 10.1118/1.3193678. PMID: 19810503; PMCID: PMC2749445 (2009).
Pavicic et al., Microfocused ultrasound with visualization: Consensus on safety and review of energy-based devices, J Cosmet Dermatol Feb. 2022, vol. 21, Issue 2: pp. 636-647, published online Dec. 24, 2021.
Wang, Xusheng Ultrasonic Generator for Surgical Applications and Non-invasive Cancer Treatment by High Intenity Focused Ultrasound. Micor and nanotechnologies/Microelectronics. Université Paris-Saclay (2016).

TABLE 4

| f [MHz] | $k_x = 0.5\ mm^{-1}$ | | $k_x = 1.0\ mm^{-1}$ | | $k_x = 1.5\ mm^{-1}$ | | $k_x = 2.0\ mm^{-1}$ | |
|---|---|---|---|---|---|---|---|---|
| | spacing [mm] | spread [mm] | spacing [mm] | spread [mm] | spacing [mm] | spread [mm] | spacing [mm] | spread [mm] |
| 2.5 | 1.43 | 0.72 | 2.86 | 1.43 | 4.30 | 2.15 | 5.73 | 2.86 |
| 2.75 | 1.30 | 0.59 | 2.60 | 1.17 | 3.91 | 1.76 | 5.21 | 2.34 |
| 3 | 1.19 | 0.48 | 2.39 | 0.95 | 3.58 | 1.43 | 4.77 | 1.91 |
| 3.25 | 1.10 | 0.39 | 2.20 | 0.77 | 3.31 | 1.16 | 4.41 | 1.54 |
| 3.5 | 1.02 | 0.31 | 2.05 | 0.61 | 3.07 | 0.92 | 4.09 | 1.23 |
| 3.75 | 0.95 | 0.24 | 1.91 | 0.48 | 2.86 | 0.72 | 3.82 | 0.95 |
| 4 | 0.90 | 0.18 | 1.79 | 0.36 | 2.69 | 0.54 | 3.58 | 0.72 |
| 4.25 | 0.84 | 0.13 | 1.69 | 0.25 | 2.53 | 0.38 | 3.37 | 0.51 |
| 4.5 | 0.80 | 0.08 | 1.59 | 0.16 | 2.39 | 0.24 | 3.18 | 0.32 |
| 4.75 | 0.75 | 0.04 | 1.51 | 0.08 | 2.26 | 0.11 | 3.02 | 0.15 |
| 5 | 0.72 | 0.00 | 1.43 | 0.00 | 2.15 | 0.00 | 2.86 | 0.00 |
| 5.25 | 0.68 | -0.03 | 1.36 | -0.07 | 2.05 | -0.10 | 2.73 | -0.14 |
| 5.5 | 0.65 | -0.07 | 1.30 | -0.13 | 1.95 | -0.20 | 2.60 | -0.26 |
| 5.75 | 0.62 | -0.09 | 1.25 | -0.19 | 1.87 | -0.28 | 2.49 | -0.37 |
| 6 | 0.60 | -0.12 | 1.19 | -0.24 | 1.79 | -0.36 | 2.39 | -0.48 |
| 6.25 | 0.57 | -0.14 | 1.15 | -0.29 | 1.72 | -0.43 | 2.29 | -0.57 |
| 6.5 | 0.55 | -0.17 | 1.10 | -0.33 | 1.65 | -0.50 | 2.20 | -0.66 |
| 6.75 | 0.53 | -0.19 | 1.06 | -0.37 | 1.59 | -0.56 | 2.12 | -0.74 |
| 7 | 0.51 | -0.20 | 1.02 | -0.41 | 1.53 | -0.61 | 2.05 | -0.82 |
| 7.25 | 0.49 | -0.22 | 0.99 | -0.44 | 1.48 | -0.67 | 1.98 | -0.89 |
| 7.5 | 0.48 | -0.24 | 0.95 | -0.48 | 1.43 | -0.72 | 1.91 | -0.95 |

FIG. 5

Annular Array for Depth Control

Poling Stripes for Split Beam (Simulines)

SYSTEMS AND METHODS FOR MEASURING ELASTICITY WITH IMAGING OF ULTRASOUND MULTI-FOCUS SHEARWAVES IN MULTIPLE DIMENSIONS

INCORPORATION BY REFERENCE

U.S. Provisional Patent Application Nos. 62/874,374 filed on Jul. 15, 2019 is incorporated herein by reference in its entirety for all purposes.

BACKGROUND

Field

Several embodiments of the invention relate to energy-based noninvasive treatments for obtaining aesthetically and/or cosmetically enhancing effects on skin and/or tissue near the skin of a human face, head, neck, and/or body with simultaneous or near simultaneous delivery of energy to multiple dimensions (e.g., two or more depths, heights, widths, spacings, orientations, placements) of tissue under a skin surface. In particular, several embodiments relate to measuring skin elasticity with constructive shearwave imaging produced by the simultaneous or near simultaneous delivery of focused energy to multiple dimensions.

Description of the Related Art

Some cosmetic procedures involve invasive procedures that may require invasive surgery. Patients not only have to endure weeks of recovery time, but also are frequently required to undergo risky anesthetic procedures. Non-invasive energy-based therapeutic devices and methods are available, but may have various shortcomings with respect to efficiency, effectiveness, and providing feedback of the efficiency and effectiveness of the therapy.

SUMMARY

In several embodiments, provided are systems and methods that provide feedback on the effectiveness of a therapeutic effect using targeted and precise ultrasound to cause a visible and effective result via a thermal pathway by splitting an ultrasound therapy beam to two, three, four, or more simultaneous focal zones for performing various treatment and/or imaging procedures. Some recipients of a therapeutic procedure may respond more quickly or favorably to a treatment due to individual morphological differences from person to person when using a pre-prescribed treatment dose and density. As a result, feedback into the progress of a therapeutic treatment increases treatment efficacy and result consistency. For therapeutic treatments that induce a laxity improvement of and around the skin, a method of measuring tissue elasticity which is a surrogate measure of tissue laxity during a treatment may provide this feedback. In several embodiments, constructive shearwave imaging measures tissue displacement from a transducer that generates two or more simultaneous focal zones producing a displacement/velocity profile within the tissue. The tissue response as this displacement propagates is a shearwave that will converge to a single point for shearwave imaging. The characteristics of the converging shearwave, such as arrival time, peak displacement, rise time, and fall time provide insight into the elasticity of the tissue between the two or more simultaneous focus zones.

Several embodiments described herein are especially useful for aesthetic and other procedures where adjusting (manually or in an automated manner) treatment parameters in real time is beneficial. In embodiments where a single subject is treated in a single session, one or more parameters such as frequency, power, intensity, duration and location of the treatment points (therapy) is modified based on the elasticity of the tissue below the skin surface. When multiple lines (e.g., two or more) of thermal coagulation points are created, the parameters can be varied between the points and/or between the lines on the face or body. As an example, if a subject has insufficient elasticity in a certain region, the duration of treatment can be extended (as compared to a skin region with more elasticity). In some embodiments, one or more of frequency, power, intensity, duration or other parameter is altered (increased or decreased) by 10-30%, 30%-50%, 50-100%, 2-3 fold, 3-5 fold, or more, and overlapping ranges therein, and in some embodiments, such alterations are correlated and/or based on elasticity.

In various embodiments, an ultrasound system is configured for focusing ultrasound to produce localized, mechanical motion within tissues and cells for the purpose of producing either localized heating for tissue coagulation or for mechanical cellular membrane disruption intended for non-invasive aesthetic use. In various embodiments, an ultrasound system is configured for lifting a brow (e.g., an eyebrow lift). In various embodiments, an ultrasound system is configured for lifting lift lax, loose or sagging tissue, such as submental (beneath the chin) and neck tissue. In various embodiments, an ultrasound system is configured for improving lines and wrinkles of the décolleté. In various embodiments, an ultrasound system is configured for reducing fat. In various embodiments, an ultrasound system is configured for reducing the appearance of cellulite. In some embodiments, a system is provided for both reducing fat and subsequently treating the loose skin that results from fat reduction.

Although various embodiments for aesthetic treatments are contemplated herein, the systems and procedures described herein are also used for non-aesthetic applications in some embodiments.

In various embodiments, an ultrasound system is configured for imaging to visualize tissue (e.g., dermal and subdermal layers of tissue) to ensure proper coupling of the transducer to the skin. In various embodiments, an ultrasound system is configured for imaging to visualize tissue (e.g., dermal and subdermal layers of tissue) to confirm appropriate depth of treatment such as to avoid certain tissues (e.g., bone).

In various embodiments, treating tissue, such as skin tissue, with multiple (e.g., two or more) beams provides one or more advantages, such as, for example, reducing treatment time, creating unique heating patterns, leveraging multiple channels for greater power, the option to treat skin at two or more depths with the same or different power levels, (e.g., a thermal coagulation point in the superficial muscular aponeurotic system ("SMAS") and another defocused energy at the surface of the skin, or other combinations), optional simultaneous treatment at different depths (e.g., such as at depths below a skin surface of 1.5 mm, 3 mm and/or 4.5 mm thermal coagulation points simultaneously or in an overlapping time period); and/or treatment with one, two, or more simultaneous linear or line focuses, such as at different depths below the skin surface or spaced apart. In some embodiments simultaneous multi-focus therapy uses dithering.

According to one embodiment, an ultrasound treatment system creates two or more simultaneous therapeutic treatment points and/or focal zones under the skin surface for a cosmetic treatment, wherein the treatment points are enlarged by dithering the ultrasound beams. In one embodiment, a focal zone is a point. In one embodiment, a focal zone is a line. In one embodiment, a focal zone is a plane. In one embodiment, a focal zone is a three-dimensional volume or shape. The dithering of the ultrasound beam focus points enlarges the treatment area by shaking, blurring, or splattering the focus point or focus zone (e.g., a focus point, line, plane, or volume) like paint through an air brush by mechanically and/or electronically scattering the location of the focus points by varying the frequency, and therefore focal point, of the ultrasound treatment beams. In some embodiments, dithering increases efficacy by making a larger treatment points and/or focal zones. In some embodiments, dithering reduces pain since the temperature of the hot spot is spread over a larger volume of tissue, allowing a potential reduction in dose. In some embodiments, mechanical dithering is one method of spreading the acoustic energy from the ultrasound beam so there is less reliance on tissue thermal conduction away from the focus. In one embodiment of mechanical dithering, the therapy transducer is moved locally around the intended center of the thermal coagulation point (TCP). The acoustic beam movement can be side-to-side, up-down, and/or angular. In one embodiment of mechanical dithering, the movement of the motion mechanism is sufficiently fast enough to create a flatter temperature profile around the intended TCP which either allows a reduction of total acoustic energy for the same effected tissue volume or the same total acoustic energy for a larger effected tissue volume or any combination thereof.

In various embodiments, a system for measuring material elasticity, the system including: an ultrasonic probe comprising an ultrasound transducer configured to deliver a plurality (e.g., two or more) of ultrasound beams to a material, the material comprising an elasticity, the plurality of ultrasound beams being focused at a plurality of individually spaced focal zones in the material, each ultrasound beam having sufficient acoustic power to generate a shear wave originating from the individually spaced focal zones and travelling through the material; an ultrasound imaging system configured to image shear waves originating from at least two of the plurality of individually spaced focal zones and converging towards a region between the at least two of the plurality of individually spaced focal zones; and an electronic processing system configured to: obtain a characteristic of the imaged shear waves; and determine the elasticity of the region of the material based on the obtained characteristic. In one embodiment, two or more shear waves originating from at least two of the focal zones will converge somewhere (anywhere in between, including but not limited to a center between the at least two focal zones, or any distance off-center, e.g., 10%, 20%, 30%, 40%, 60%, 70%, 80%, 90% of the distance between for example, a first and a second focal zone) in the medium depending on the timing of the shear waves. In some: embodiments, the imaging system may look away from the where the shear waves converge (e.g. have a linear imaging array) or the shear waves may converge at a location that is not half the distance between the focal zones based on the timing of when the shear waves were generated (e.g. simultaneous versus sequential) or tissue differences.

In one embodiment, the characteristic of the imaged shear waves includes at least one of an arrival time of the shear waves, a peak displacement of the shear waves, rise time of the shear waves, and fall time of the shear waves. In one embodiment, the ultrasound transducer is configured to deliver the ultrasound beam to the material using amplitude modulation to focus the ultrasound beam at the plurality of individually spaced focal zones in the material. In one embodiment, the ultrasound beam is focused simultaneously at the plurality of individually spaced focal zones in the material. In one embodiment, the ultrasound beam is focused sequentially at the plurality of individually spaced focal zones in the material. In one embodiment, the ultrasound transducer is configured to deliver the ultrasound beam to the material using frequency modulation to focus the ultrasound beam at the plurality of individually spaced focal zones in the material. In one embodiment, the ultrasound beam is focused simultaneously at the plurality of individually spaced focal zones in the material. In one embodiment, the ultrasound beam is focused sequentially at the plurality of individually spaced focal zones in the material. In one embodiment, the at least one ultrasound transducer is configured to deliver the ultrasound beam to a plurality of excitation zones of the material corresponding to the plurality of individually spaced focal zones. In one embodiment, the plurality of individually spaced focal zones coincide with the plurality of excitation zones. In one embodiment, the plurality of individually spaced focal zones are spaced apart from the plurality of excitation zones. In one embodiment, the system further comprising a movement assembly configured to move the ultrasonic probe. In one embodiment, the material comprises an organic material. In one embodiment, the material comprises tissue. In one embodiment, the material comprises skin. In one embodiment, the electronic processing system is configured to determine elasticity of the material in real-time while the ultrasound beam is delivered to the material. In one embodiment, the system is configured for use in a cosmetic procedure.

In various embodiments, a method of non-invasively measuring elasticity of a material, the method comprising: coupling an ultrasonic probe comprising at least one ultrasound transducer with a material; delivering a plurality of ultrasound beams from the ultrasonic transducer to the material; focusing the plurality of ultrasound beams at a plurality of individually spaced focal zones in the material; generating shear waves originating from the plurality of individually spaced focal zones and travelling through the material; imaging the shear waves originating from at least two of the plurality of individually spaced focal zones and converging towards a region between the at least two of the plurality of individually spaced focal zones; obtaining a characteristic of the imaged shear waves; and determining elasticity of the region of the material based on the obtained characteristic.

In one embodiment, the characteristic of the imaged shear waves includes at least one of an arrival time of the shear waves, a peak displacement of the shear waves, rise time of the shear waves, and fall time of the shear waves. In one embodiment, focusing the ultrasound beam at a plurality of individually spaced focal zones in the material comprises modulating amplitude or frequency of one or more signals driving the ultrasound transducer. In one embodiment, the ultrasound beam is focused simultaneously at the plurality of individually spaced focal zones in the material. In one embodiment, the ultrasound beam is focused sequentially at the plurality of individually spaced focal zones in the material. In one embodiment, the ultrasound beam is delivered to a plurality of excitation zones of the material corresponding to the plurality of individually spaced focal zones. In one embodiment, the plurality of individually spaced focal zones coincide with the plurality of excitation zones. In one embodiment, the plurality of individually spaced focal zones are spaced apart from the plurality of excitation zones. In one embodiment, the method includes moving the ultrasonic probe to focus the ultrasound beam at the plurality of individually spaced focal zones in the material. In one embodiment, the material comprises an organic material. In one embodiment, the material comprises tissue. In one embodiment, the material comprises skin. In one embodiment, the elasticity of the material is determined in real-time while the ultrasound beam is delivered to the material. In one embodiment, the method includes determining efficacy of an ultrasound therapy configured to provide cosmetic or aesthetic improvements in the material, wherein the material comprises a biological tissue. In one embodiment, determining efficacy of an ultrasound therapy is configured to provide cosmetic or aesthetic improvements comprises correlating the determined elasticity to creation of a thermal coagulation point (TCP) in the biological tissue.

In various embodiments, a method of measuring elasticity of a material by creating multiple simultaneous focal points includes: coupling an ultrasonic transducer probe to a material surface; wherein the ultrasonic transducer probe comprises a single piezoelectric transduction element configured to focus a plurality of individual spaced focal zones; focusing a plurality of individual spaced focal zones in a region below the material surface with the single piezoelectric transduction element, wherein the focusing at the plurality of individual spaced focal zones is simultaneous; obtaining a characteristic of a plurality of shearwaves originating from at least two of the plurality of individual focal zones converging towards a region between the at least two of the plurality of individual focal zones; determining elasticity of the region below the skin surface between the at least two of the plurality of individual focal zones from the obtained characteristic of the shearwave; and determining an effectiveness of the noninvasive cosmetic procedure based on the determined elasticity, wherein the transducer module comprises a single ultrasound transducer configured to apply ultrasonic therapy to tissue at a plurality of individual excitation zones corresponding to the individual focal zones.

In one embodiment, the characteristic of the shearwaves includes at least one of an arrival time of the shearwaves, a peak displacement of the shearwaves, rise time of the shearwaves, and fall time of the shearwaves. In one embodiment, an individual excitation zone of the plurality of individual excitation zones coincides with a corresponding one of the plurality of individual focal zones. In one embodiment, an individual excitation zone of the plurality of individual excitation zones is spaced apart from a corresponding one of the plurality of individual focal zones.

In several of the embodiments described herein, the procedure is entirely cosmetic and not a medical act. For example, in one embodiment, the methods described herein need not be performed by a doctor, but at a spa or other aesthetic institute. In some embodiments, a system can be used for the non-invasive cosmetic treatment of skin.

The methods summarized above and set forth in further detail below describe certain actions taken by a practitioner; however, it should be understood that they can also include the instruction of those actions by another party. Thus, actions such as "measuring a shearwave" include "instructing the measuring a shearwave."

In some embodiments, the system comprises various features that are present as single features (as opposed to multiple features). For example, in one embodiment, the system includes a single transduction element that produces two simultaneous treatment focus points that are dithered. Multiple features or components are provided in alternate embodiments. In various embodiments, the system comprises, consists essentially of, or consists of one, two, three, or more embodiments of any features or components disclosed herein. In some embodiments, a feature or component is not included and can be negatively disclaimed from a specific claim, such that the system is without such feature or component.

Further, areas of applicability will become apparent from the description provided herein. It should be understood that the description and specific examples are intended for purposes of illustration only and are not intended to limit the scope of the embodiments disclosed herein.

BRIEF DESCRIPTION OF THE DRAWINGS

The drawings described herein are for illustration purposes only and are not intended to limit the scope of the present disclosure in any way. Embodiments of the present invention will become more fully understood from the detailed description and the accompanying drawings wherein:

FIG. 5 is table illustrating foci separation for apertures with different spatial frequencies according to various embodiments of the present invention.

DETAILED DESCRIPTION

Figure 1A:
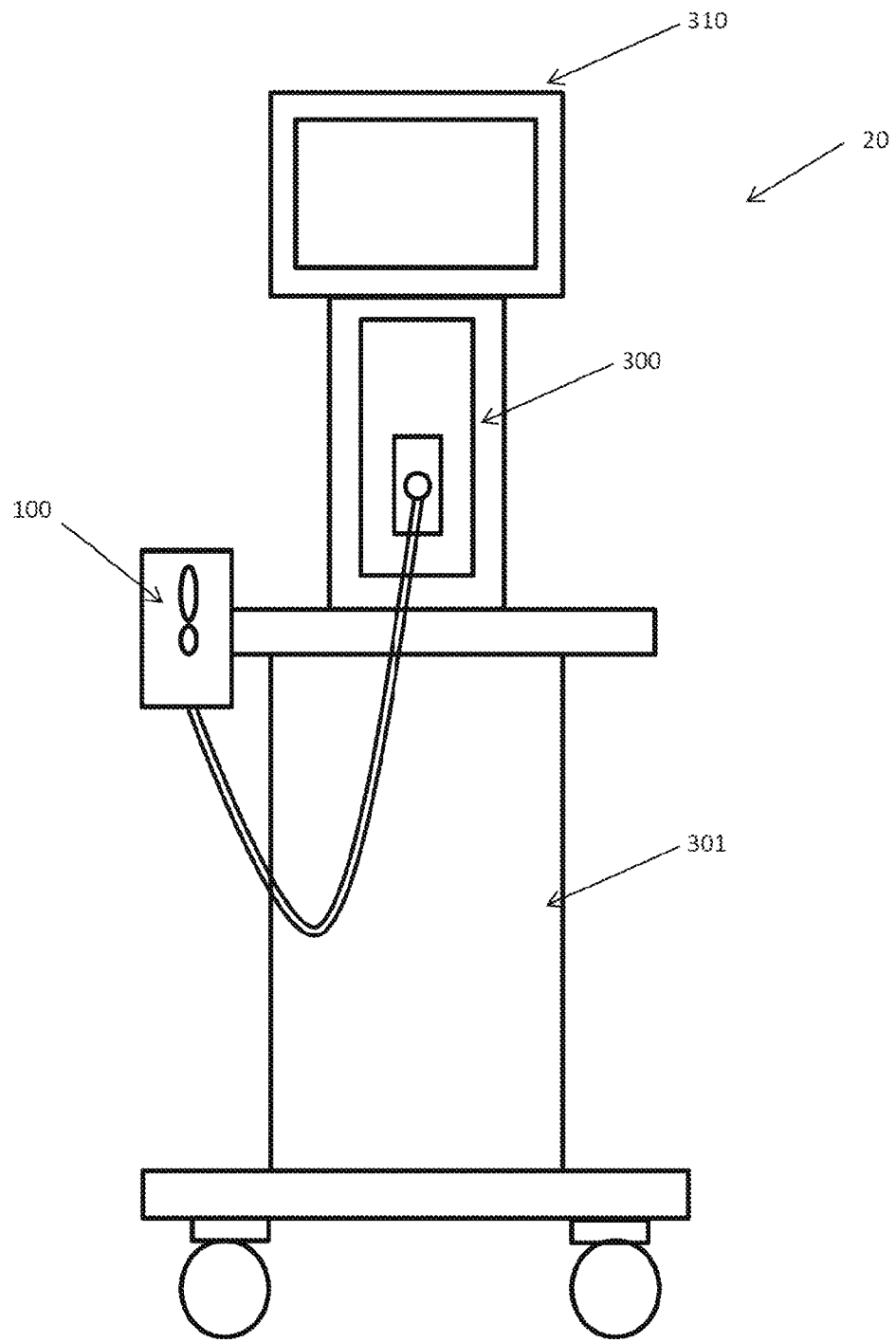
FIG. 1A is a schematic illustration of an ultrasound system according to various embodiments of the present invention.

The following description sets forth examples of embodiments, and is not intended to limit the present invention or its teachings, applications, or uses thereof. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

In various embodiments, systems and methods for ultrasound treatment of tissue are adapted for and/or configured to provide cosmetic treatment. In some embodiments, devices and methods of directing ultrasound therapy to a single focus point or multiple, simultaneous focus points, employing ultrasound imaging to confirm sufficient acoustic coupling to a treatment area for improving performance or providing improved correlation between movement in a first and second direction when forming images in cosmetic and/or medical procedures are provided in several embodiments. In various embodiments as used herein, "simultaneous" refers to occurring at the same time, or with a time difference of less than 1 ms, 0.5 ms, 0.1 ms, 0.05 ms, or 0.01 ms. In various embodiments, tissue below or even at a skin surface such as epidermis, dermis, fascia, muscle, fat, and superficial muscular aponeurotic system ("SMAS"), are treated non-invasively with ultrasound energy. The ultrasound energy can be focused at one or more treatment points and/or zones, can be unfocused and/or defocused, and can be applied to a region of interest containing at least one of epidermis, dermis, hypodermis, fascia, muscle, fat, cellulite, and SMAS to achieve a cosmetic and/or therapeutic effect. In various embodiments, systems and/or methods provide non-invasive dermatological treatment to tissue through thermal treatment, coagulation, ablation, and/or tightening. In several embodiments disclosed herein, non-invasive ultrasound is used to achieve one or more of the following effects: a face lift, a brow lift, a chin lift, an eye treatment (e.g., malar bags, treat infraorbital laxity), a wrinkle reduction, fat reduction (e.g., treatment of adipose and/or cellulite), cellulite treatment (e.g., dimple or non-dimple type female gynoid lipodystrophy), décolletage improvement (e.g., upper chest), a buttock lift (e.g., buttock tightening), a skin laxity treatment (e.g., treatment of tissue for tightening or an abdominal laxity treatment), a scar reduction, a burn treatment, a tattoo removal, a vein removal, a vein reduction, a treatment on a sweat gland, a treatment of hyperhidrosis, sun spot removal, an acne treatment, and a pimple removal. In one embodiment, fat reduction is achieved. In various embodiments, cellulite (e.g., dimple or non-dimple type gynoid lipodystrophy) reduction or amelioration of one or more characteristics (such as dimples, nodularity, "orange peel" appearance, etc., is achieved by about 10-20%, 20-40%, 40-60%, 60-80% or higher (as well as overlapping ranging therein) as compared to, for example, untreated tissue. In one embodiment, décolletage is treated. In some embodiments, two, three or more beneficial effects are achieved during the same treatment session, and may be achieved simultaneously.

Various embodiments of the present invention relate to devices or methods of controlling the delivery of energy to tissue. In various embodiments, various forms of energy can include acoustic, ultrasound, light, laser, radio-frequency (RF), microwave, electromagnetic, radiation, thermal, cryogenic, electron beam, photon-based, magnetic, magnetic resonance, and/or other energy forms. Various embodiments of the present invention relate to devices or methods of splitting an ultrasonic energy beam into multiple beams. In various embodiments, devices or methods can be used to alter the delivery of ultrasound acoustic energy in any procedures such as, but not limited to, therapeutic ultrasound, diagnostic ultrasound, ultrasonic welding, any application that involves coupling mechanical waves to an object, and other procedures. Generally, with therapeutic ultrasound, a tissue effect is achieved by concentrating the acoustic energy using focusing techniques from the aperture. In some instances, high intensity focused ultrasound (HIFU) is used for therapeutic purposes in this manner. In one embodiment, a tissue effect created by application of therapeutic ultrasound at a particular depth to can be referred to as creation of a thermal coagulation point (TCP). In some embodiments, a zone can include a point. In some embodiments, a zone is a line, plane, spherical, elliptical, cubical, or other one-, two-, or three-dimensional shape. It is through creation of TCPs at particular positions that thermal and/or mechanical ablation of tissue can occur non-invasively or remotely. In some embodiments, an ultrasound treatment does not include cavitation and/or shock waves. In some embodiments, an ultrasound treatment includes cavitation and/or shock waves.

In one embodiment, TCPs can be created in a linear or substantially linear, curved or substantially curved, zone or sequence, with each individual TCP separated from neighboring TCPs by a treatment spacing. In one embodiment, multiple sequences of TCPs can be created in a treatment region. For example, TCPs can be formed along a first sequence and a second sequence separated by a treatment distance from the first sequence. Although treatment with therapeutic ultrasound can be administered through creation of individual TCPs in a sequence and sequences of individual TCPs, it may be desirable to reduce treatment time and corresponding risk of pain and/or discomfort experienced by a patient. Therapy time can be reduced by forming multiple TCPs simultaneously, nearly simultaneously, or sequentially. In some embodiments, a treatment time can be reduced 10%, 20%, 25%, 30%, 35%, 40%, 45%, 50%, 55%, 60%, 65%, 70%, 75%, 80% or more by creating multiple TCPs.

Various embodiments of the present invention address potential challenges posed by administration of ultrasound therapy. In various embodiments, time for effecting the formation of TCPs for a desired cosmetic and/or therapeutic treatment for a desired clinical approach at a target tissue is reduced. In various embodiments, target tissue is, but is not limited to, any of skin, eyelids, eye lash, eye brow, *caruncula lacrimalis*, crow's feet, wrinkles, eye, nose, mouth (e.g., nasolabial fold, perioral wrinkles), tongue, teeth, gums, ears, brain, heart, lungs, ribs, abdomen (e.g., for abdominal laxity), stomach, liver, kidneys, uterus, breast, vagina, prostrate, testicles, glands, thyroid glands, internal organs, hair, muscle, bone, ligaments, cartilage, fat, fat lobuli, adipose tissue, subcutaneous tissue, implanted tissue, an implanted organ, lymphoid, a tumor, a cyst, an abscess, or a portion of a nerve, or any combination thereof.

Various embodiments of simultaneous ultrasound treatment at multiple locations in tissue are described in U.S. application Ser. No. 14/193,234, which published as U.S. Publication No. 2014/0257145 on Sep. 11, 2014, which is incorporated in its entirety by reference, herein.

System Overview

Figure 1B:
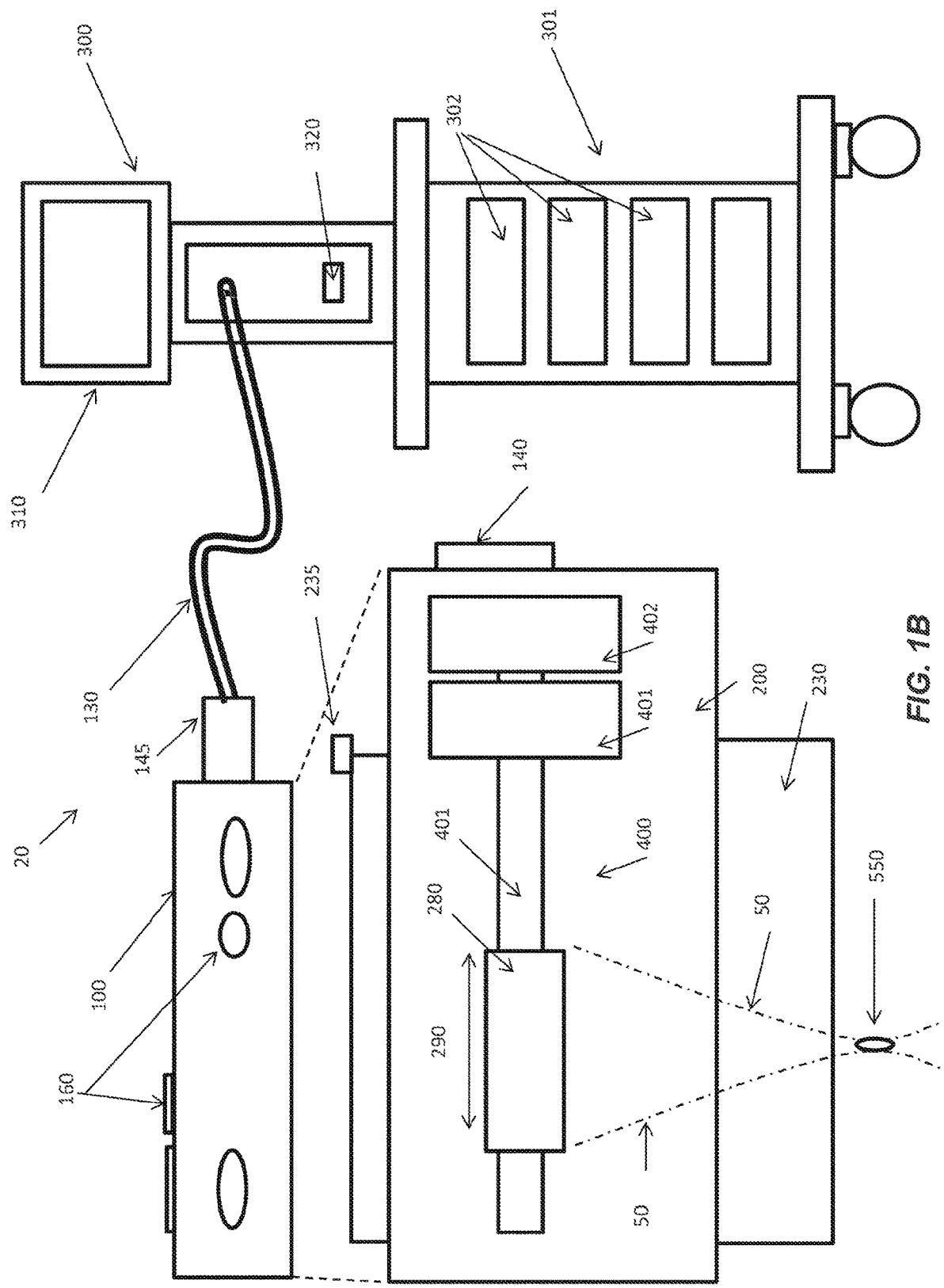
FIG. 1B is a schematic illustration of an ultrasound system according to various embodiments of the present invention.
Figure 1C:
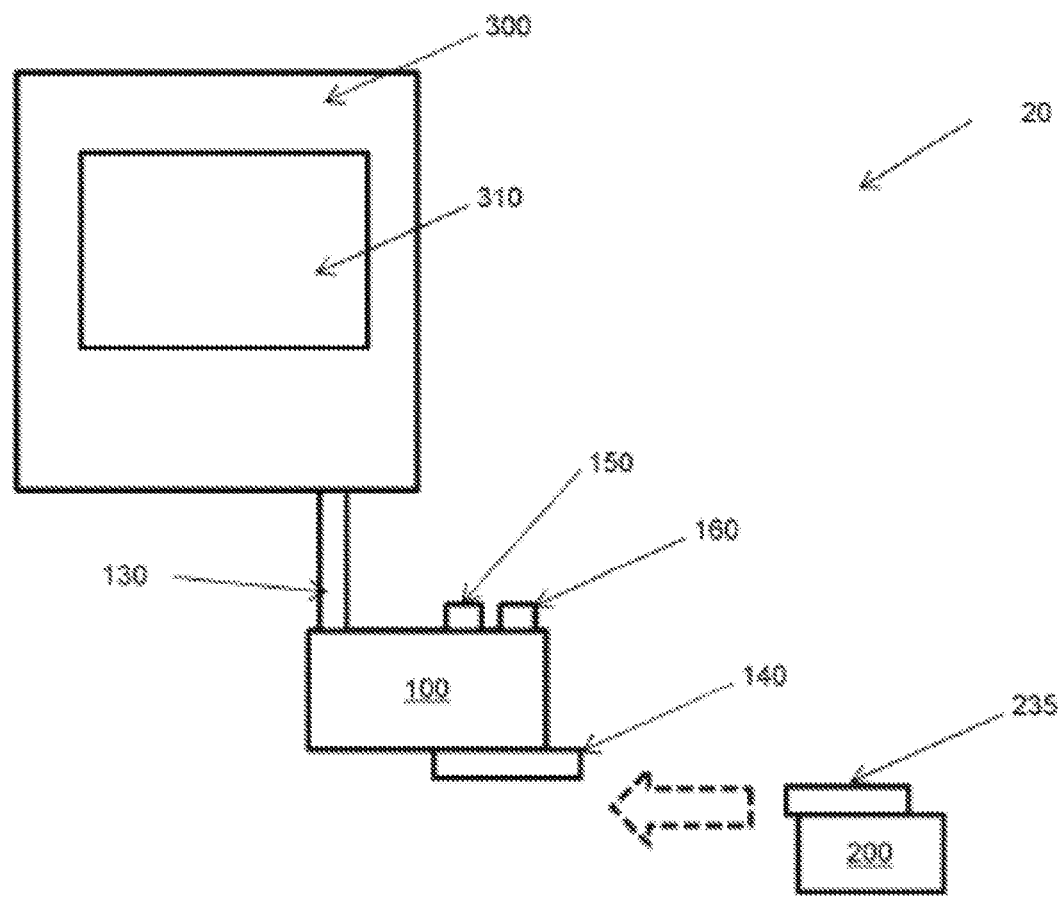
FIG. 1C is a schematic illustration of an ultrasound system according to various embodiments of the present invention.

With reference to the illustration in FIGS. 1A, 1B, and 1C, various embodiments of an ultrasound system 20 includes a hand wand (e.g., handpiece) 100, module (e.g., transducer module, cartridge, probe) 200, and a controller (e.g., console) 300. In some embodiments, a console 300 comprises a communication system (e.g., Wi-Fi, Bluetooth, modem, etc. to communicate with another party, a manufacturer, a supplier, a service provider, the Internet, and/or a cloud. In some embodiments, a cart 301 provides mobility and/or position of the system 20, and can include wheels, surfaces to write on or place components, and/or compartments 302 (e.g., drawers, containers, shelves, etc.) to, for example, store or organize components. In some embodiments, the cart has a power supply, such as a power connection to a battery and/or one or more cords to connect power, communications (e.g., Ethernet) to the system 20. In some embodiments, the system 20 comprises a cart 301. In some embodiments, the system 20 does not comprise a cart 301. The hand wand 100 can be coupled to the controller 300 by an interface 130, which may be a wired or wireless interface. The interface 130 can be coupled to the hand wand 100 by a connector 145. The distal end of the interface 130 can be connected to a controller connector on a circuit 345 (not shown). In one embodiment, the interface 130 can transmit controllable power from the controller 300 to the hand wand 100. In an embodiment, the system 20 has multiple imaging channels (e.g., 8 channels) for ultra-clear HD (high definition) visualization of subcutaneous structures to improve imaging. In an embodiment, the system 20 multiple therapy channels (e.g., 8 channels) and a precision linear-drive motor that doubles treatment accuracy while increasing speed (e.g., by 25%, 40%, 50%, 60%, 75%, 100% or more). Together, these features establish one of the most versatile system platforms in the industry and provide a foundation for unprecedented future possibilities.

In various embodiments, the controller 300 can be adapted to and/or configured for operation with the hand wand 100 and the module 200, as well as the overall ultrasound system 20 functionality. In various embodiments, multiple controllers 300, 300', 300", etc. can be adapted to and/or configured for operation with multiple hand wands 100, 100', 100", etc. and or multiple modules 200, 200', 200", etc. The controller 300 can include connectivity to one or more interactive graphical display 310, which can include a touchscreen monitor and Graphic User Interface (GUI) that allows the user to interact with the ultrasound system 20. In one embodiment, a second smaller, more mobile display that allows the user to more easily position and view the treatment screen. In one embodiment, a second display that allows the system user to view a treatment screen (e.g., on a wall, on a mobile device, large screen, remote screen). In one embodiment the graphical display 310 includes a touchscreen interface 315 (not shown). In various embodiments, the display 310 sets and displays the operating conditions, including equipment activation status, treatment parameters, system messages and prompts, and ultrasound images. In various embodiments, the controller 300 can be adapted to and/or configured to include, for example, a microprocessor with software and input/output devices, systems and devices for controlling electronic and/or mechanical scanning and/or multiplexing of transducers and/or multiplexing of transducer modules, a system for power delivery, systems for monitoring, systems for sensing the spatial position of the probe and/or transducers and/or multiplexing of transducer modules, and/or systems for handling user input and recording treatment results, among others. In various embodiments, the controller 300 can include a system processor and various analog and/or digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software running on the system process may be adapted to and/or configured to control all initialization, timing, level setting, monitoring, safety monitoring, and all other ultrasound system functions for accomplishing user-defined treatment objectives. Further, the controller 300 can include various input/output modules, such as switches, buttons, etc., that may also be suitably adapted to and/or configured to control operation of the ultrasound system 20.

In one embodiment, the hand wand 100 includes one or more finger activated controllers or switches, such as 150 and 160. In various embodiments, one or more thermal treatment controllers 160 (e.g., switch, button) activates and/or stops treatment. In various embodiments, one or more imaging controllers 150 (e.g., switch, button) activates and/or stops imaging. In one embodiment, the hand wand 100 can include a removable module 200. In other embodiments, the module 200 may be non-removable. In various embodiments, the module 200 can be mechanically coupled to the hand wand 100 using a latch or coupler 140. In various embodiments, an interface guide 235 or multiple interface guides 235 can be used for assisting the coupling of the module 200 to the hand wand 100. The module 200 can include one or more ultrasound transducers 280. In some embodiments, an ultrasound transducer 280 includes one or more ultrasound elements. The module 200 can include one or more ultrasound elements. The hand wand 100 can include imaging-only modules, treatment-only modules, imaging-and-treatment modules, and the like. In various embodiments, the ultrasound transducer 280 is movable in one or more directions 290 within the module 200. The transducer 280 is connected to a motion mechanism 400. In various embodiments, the motion mechanism comprises zero, one, or more bearings, shafts, rods, screws, lead screws 401, encoders 402 (e.g., optical encoder to measure position of the transducer 280), motors 403 (e.g., a step motor) to help ensure accurate and repeatable movement of the transducer 280 within the module 200. In various embodiments, module 200 can include a transducer 280 which can emit energy through an acoustically transparent member 230. In one embodiment, the control module 300 can be coupled to the hand wand 100 via the interface 130, and the graphic user interface 310 can be adapted to and/or configured for controlling the module 200. In one embodiment, the control module 300 can provide power to the hand wand 100. In one embodiment, the hand wand 100 can include a power source. In one embodiment, the switch 150 can be adapted to and/or configured for controlling a tissue imaging function and the switch 160 can be adapted to and/or configured for controlling a tissue treatment function. In various embodiments, delivery of emitted energy 50 at a suitable focal depth, distribution, timing, and energy level is provided by the module 200 through controlled operation by the control system 300 of the transducer 280 to achieve the desired therapeutic effect with a thermal coagulation zone 550 ("TCP" e.g., a thermal coagulation point).

In one embodiment, the module 200 can be coupled to the hand wand 100. The module 200 can emit and receive energy, such as ultrasonic energy. The module 200 can be electronically coupled to the hand wand 100 and such coupling may include an interface which is in communication with the controller 300. In one embodiment, the interface guide 235 can be adapted to and/or configured to provide electronic communication between the module 200 and the hand wand 100. The module 200 can comprise various probe and/or transducer configurations. For example, the module 200 can be adapted to and/or configured for a combined dual-mode imaging/therapy transducer, coupled or co-housed imaging/therapy transducers, separate therapy and imaging probes, and the like. In one embodiment, when the module 200 is inserted into or connected to the hand wand 100, the controller 300 automatically detects it and updates the interactive graphical display 310.

In some embodiments, an access key 320 (e.g., a secure USB drive, key) is connected (e.g., removably) to a system 20 to permit the system 20 to function. In various embodiments, the access key is programmed to be customer specific, and serves multiple functions, including system security, country/region specific access to treatment guidelines and functionality, software upgrades, support log transfers and/or credit transfer and/or storage. In various embodiments, the system 20 has internet and/or data connectivity. In an embodiment, connectivity provides a method by which data is transferred between the system 20 provider and the customer. In various embodiments, data includes credits, software updates and support logs. Connectivity is divided into different model embodiments, based on how a user's console is connected to the internet. In one embodiment, Disconnected Model connectivity comprises a console that is disconnected from the internet and customer doesn't have internet access. Credit transfers and software upgrades are conducted by shipping access key(s), (e.g., USB drives) to the customer. In one embodiment, Semi-Connected Model connectivity comprises a console that is disconnected from the internet but customer has internet access. Credit transfers, software upgrades and support log transfers are conducted using the customer's personal computer, smart phone, or other computing device in conjunction with the system access key to transfer data. In one embodiment, Fully-Connected Model connectivity comprises a console that is wirelessly connected to the internet using Wi-Fi, cellular modem, Bluetooth, or other protocol. Credit transfers, software upgrades and support log transfers are made directly between the console and the cloud. In various embodiments, the system 20 connects to an online portal, for streamlined inventory management, on-demand treatment purchases and business analytics insights to drive customer aesthetic treatment business to the next level.

Figure 2:
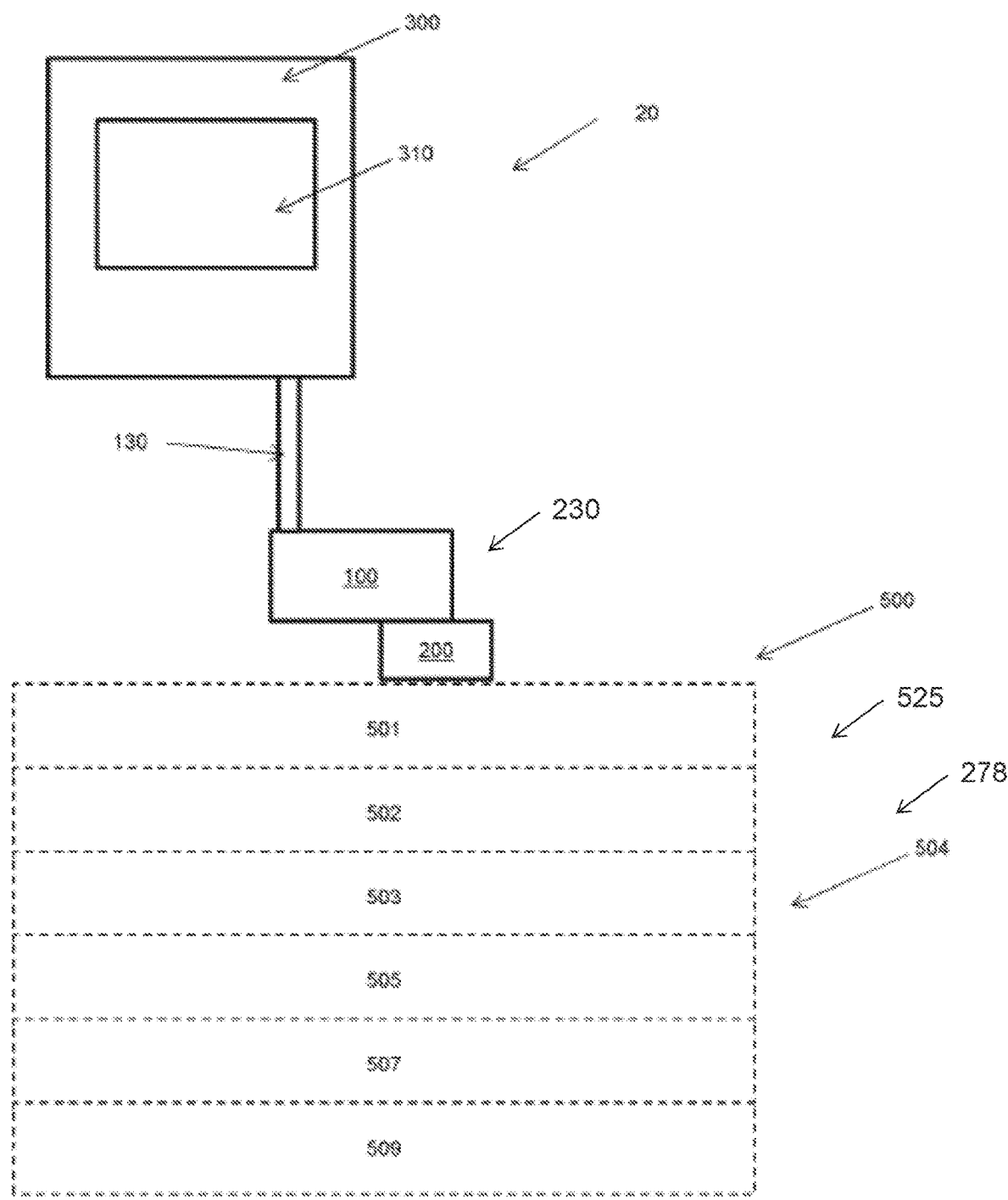
FIG. 2 is a schematic illustration of an ultrasound system coupled to a region of interest according to various embodiments of the present invention.

In various embodiments, tissue below or even at a skin surface such as epidermis, dermis, hypodermis, fascia, and superficial muscular aponeurotic system ("SMAS"), and/or muscle are treated non-invasively with ultrasound energy. Tissue may also include blood vessels and/or nerves. The ultrasound energy can be focused, unfocused or defocused and applied to a region of interest containing at least one of epidermis, dermis, hypodermis, fascia, and SMAS to achieve a therapeutic effect. FIG. 2 is a schematic illustration of the ultrasound system 20 coupled to a region of interest 10. In various embodiments, tissue layers of the region of interest 10 can be at any part of the body of a subject. In one embodiment, the tissue layers are in the head and face region of the subject. The cross-sectional portion of the tissue of the region of interest 10 includes a skin surface 501, an epidermal layer 502, a dermal layer 503, a fat layer 505, a superficial muscular aponeurotic system 507 (hereinafter "SMAS 507"), and a muscle layer 509. The tissue can also include the hypodermis 504, which can include any tissue below the dermal layer 503. The combination of these layers in total may be known as subcutaneous tissue 510. Also illustrated in FIG. 2 is a treatment zone 525 which is below the surface 501. In one embodiment, the surface 501 can be a surface of the skin of a subject 500. Although an embodiment directed to therapy at a tissue layer may be used herein as an example, the system can be applied to any tissue in the body. In various embodiments, the system and/or methods may be used on tissue (including but not limited to one or a combination of muscles, fascia, SMAS, dermis, epidermis, fat, adipose cells, cellulite, which may be called gynoid lipodystrophy, (e.g., non-dimple type female gynoid lipodystrophy), collagen, skin, blood vessels, of the face, neck, head, arms, legs, or any other location on or in the body (including bodily cavities). In various embodiments, cellulite (e.g., non-dimple type female gynoid lipodystrophy) reduction is achieved in an amount of 2%, 5%, 10%, 15%, 20%, 25%, 30%, 40%, 50%, 75%, 80%, 90%, 95%, and any ranges therein.

Figure 3:
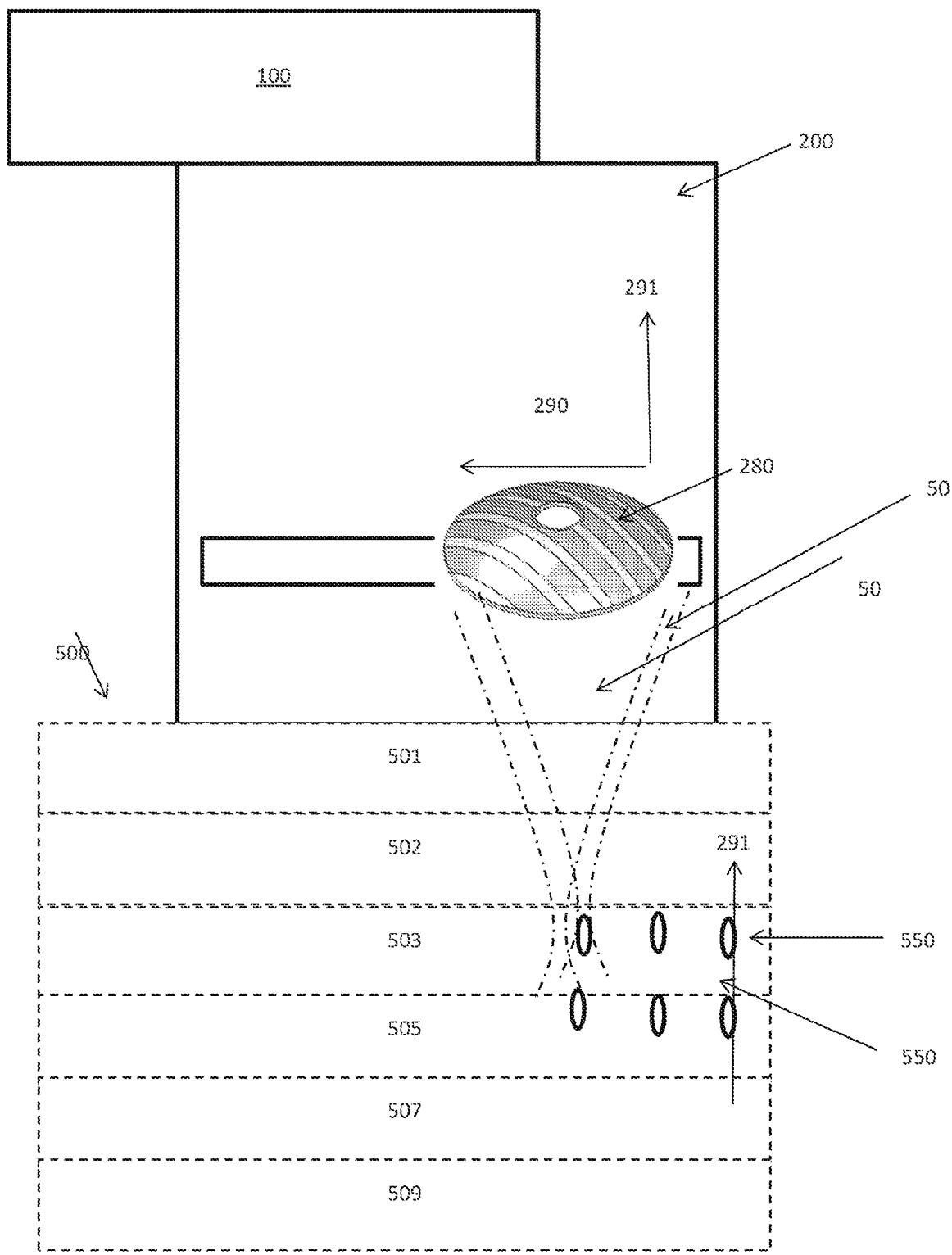
FIG. 3 is a schematic illustration of a portion of a transducer according to various embodiments of the present invention.

With reference to the illustration in FIG. 2, an embodiment of the ultrasound system 20 includes the hand wand 100, the module 200, and the controller 300. In one embodiment, the module 200 includes a transducer 280. FIG. 3 illustrates an embodiment of an ultrasound system 20 with a transducer 280 adapted to and/or configured to treat tissue at multiple focal depths 278. In one embodiment, the focal depth 278 is a distance between the transducer 280 and the target tissue for treatment. In one embodiment, a focal depth 278 is fixed for a given transducer 280. In one embodiment, a focal depth 278 is variable for a given transducer 280. In one embodiment, a transducer 280 is configured to treat simultaneously at multiple depths below a skin surface (e.g., 1.5 mm, 3.0 mm, 4.5 mm, or other depths).

Figure 4:
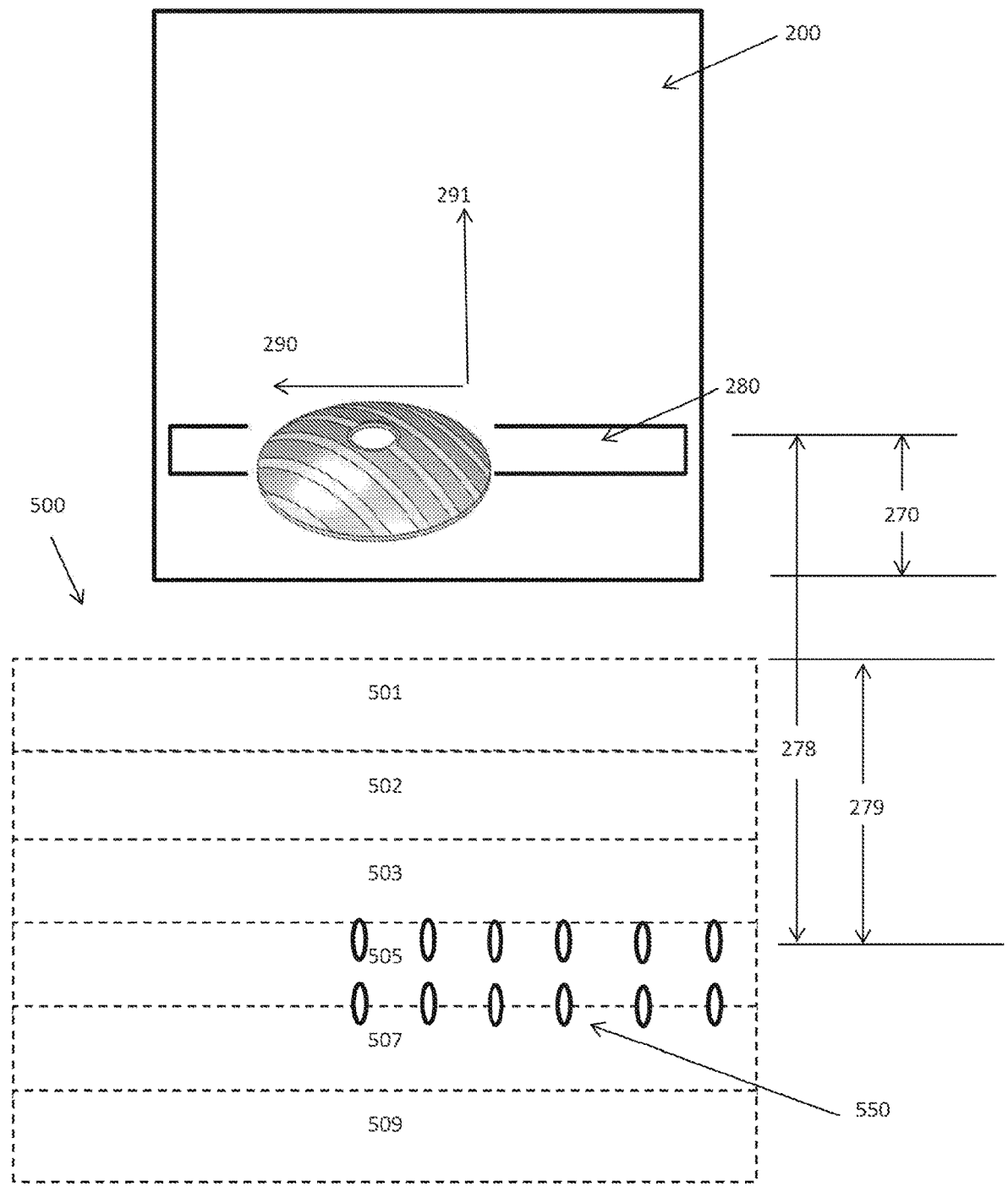
FIG. 4 is a partial cut away side view of an ultrasound system according to various embodiments of the present invention.

With reference to the illustration in FIG. 4, the module 200 can include a transducer 280 which can emit energy through an acoustically transparent member 230. In various embodiments, a depth may refer to the focal depth 278. In one embodiment, the transducer 280 can have an offset distance 270, which is the distance between the transducer 280 and a surface of the acoustically transparent member 230. In one embodiment, the focal depth 278 of a transducer 280 is a fixed distance from the transducer. In one embodiment, a transducer 280 may have a fixed offset distance 270 from the transducer to the acoustically transparent member 230. In one embodiment, an acoustically transparent member 230 is adapted to and/or configured at a position on the module 200 or the ultrasound system 20 for contacting the skin surface 501. In various embodiments, the focal depth 278 exceeds the offset distance 270 by an amount to correspond to treatment at a target area located at a tissue depth 279 below a skin surface 501. In various embodiments, when the ultrasound system 20 placed in physical contact with the skin surface 501, the tissue depth 279 is a distance between the acoustically transparent member 230 and the target area, measured as the distance from the portion of the hand wand 100 or module 200 surface that contacts skin (with or without an acoustic coupling gel, medium, etc.) and the depth in tissue from that skin surface contact point to the target area. In one embodiment, the focal depth 278 can correspond to the sum of an offset distance 270 (as measured to the surface of the acoustically transparent member 230 in contact with a coupling medium and/or skin 501) in addition to a tissue depth 279 under the skin surface 501 to the target region. In various embodiments, the acoustically transparent member 230 is not used.

Coupling components can comprise various substances, materials, and/or devices to facilitate coupling of the transducer 280 or module 200 to a region of interest. For example, coupling components can comprise an acoustic coupling system adapted to and/or configured for acoustic coupling of ultrasound energy and signals. Acoustic coupling system with possible connections such as manifolds may be utilized to couple sound into the region of interest, provide liquid- or fluid-filled lens focusing. The coupling system may facilitate such coupling through use of one or more coupling media, including air, gases, water, liquids, fluids, gels, solids, non-gels, and/or any combination thereof, or any other medium that allows for signals to be transmitted between the transducer 280 and a region of interest. In one embodiment one or more coupling media is provided inside a transducer. In one embodiment a fluid-filled module 200 contains one or more coupling media inside a housing. In one embodiment a fluid-filled module 200 contains one or more coupling media inside a sealed housing, which is separable from a dry portion of an ultrasonic device. In various embodiments, a coupling medium is used to transmit ultrasound energy between one or more devices and tissue with a transmission efficiency of 100%, 99% or more, 98% or more, 95% or more, 90% or more, 80% or more, 75% or more, 60% or more, 50% or more, 40% or more, 30% or more, 25% or more, 20% or more, 10% or more, and/or 5% or more.

In various embodiments, the transducer 280 can image and treat a region of interest at any suitable tissue depths 279. In one embodiment, the transducer module 280 can provide an acoustic power in a range of about 1 W or less, between about 1 W to about 100 W, and more than about 100 W, e.g., 200 W, 300 W, 400 W, 500 W. In one embodiment, the transducer module 280 can provide an acoustic power at a frequency of about 1 MHz or less, between about 1 MHz to about 10 MHz (e.g., 1.75 MHz, 3 MHZ, 4 MHz, 4.5 MHz, 7 MHz, 10 MHz), and more than about 10 MHz. In one embodiment, the module 200 has a focal depth 278 for a treatment at a tissue depth 279 of about 4.5 mm below the skin surface 501. In one embodiment, the module 200 has a focal depth 278 for a treatment at a tissue depth 279 of about 3 mm below the skin surface 501. In one embodiment, the module 200 has a focal depth 278 for a treatment at a tissue depth 279 of about 1.5 mm below the skin surface 501. Some non-limiting embodiments of transducers 280 or modules 200 can be adapted to and/or configured for delivering ultrasonic energy at a tissue depth of 1.5 mm, 3 mm, 4.5 mm, 6 mm, 7 mm, less than 3 mm, between 3 mm and 4.5 mm, between 4.5 mm and 6 mm, more than more than 4.5 mm, more than 6 mm, etc., and anywhere in the ranges of 0-3 mm, 0-4.5 mm, 0-6 mm, 0-25 mm, 0-100 mm, etc. and any depths therein. In one embodiment, the ultrasound system 20 is provided with two or more transducer modules 280. For example, a first transducer module can apply treatment at a first tissue depth (e.g., about 4.5 mm) and a second transducer module can apply treatment at a second tissue depth (e.g., of about 3 mm), and a third transducer module can apply treatment at a third tissue depth (e.g., of about 1.5-2 mm). In one embodiment, at least some or all transducer modules can be adapted to and/or configured to apply treatment at substantially same depths.

In various embodiments, changing the number of focus point locations (e.g., such as with a tissue depth 279) for an ultrasonic procedure can be advantageous because it permits treatment of a patient at varied tissue depths even if the focal depth 278 of a transducer 270 is fixed. This can provide synergistic results and maximizing the clinical results of a single treatment session. For example, treatment at multiple depths under a single surface region permits a larger overall volume of tissue treatment, which results in enhanced collagen formation and tightening. Additionally, treatment at different depths affects different types of tissue, thereby producing different clinical effects that together provide an enhanced overall cosmetic result. For example, superficial treatment may reduce the visibility of wrinkles and deeper treatment may induce formation of more collagen growth. Likewise, treatment at various locations at the same or different depths can improve a treatment.

Although treatment of a subject at different locations in one session may be advantageous in some embodiments, sequential treatment over time may be beneficial in other embodiments. For example, a subject may be treated under the same surface region at one depth in time one, a second depth in time two, etc. In various embodiments, the time can be on the order of nanoseconds, microseconds, milliseconds, seconds, minutes, hours, days, weeks, months, or other time periods. The new collagen produced by the first treatment may be more sensitive to subsequent treatments, which may be desired for some indications. Alternatively, multiple depth treatment under the same surface region in a single session may be advantageous because treatment at one depth may synergistically enhance or supplement treatment at another depth (due to, for example, enhanced blood flow, stimulation of growth factors, hormonal stimulation, etc.). In several embodiments, different transducer modules provide treatment at different depths. In one embodiment, a single transducer module can be adjusted or controlled for varied depths. Safety features to minimize the risk that an incorrect depth will be selected can be used in conjunction with the single module system.

In several embodiments, a method of treating the lower face and neck area (e.g., the submental area) is provided. In several embodiments, a method of treating (e.g., softening) mentolabial folds is provided. In other embodiments, a method of treating the eye region (e.g., malar bags, treat infraorbital laxity) is provided. Upper lid laxity improvement and periorbital lines and texture improvement will be achieved by several embodiments by treating at variable depths. By treating at varied locations in a single treatment session, optimal clinical effects (e.g., softening, tightening) can be achieved. In several embodiments, the treatment methods described herein are non-invasive cosmetic procedures. In some embodiments, the methods can be used in conjunction with invasive procedures, such as surgical face-lifts or liposuction, where skin tightening is desired. In various embodiments, the methods can be applied to any part of the body.

In one embodiment, a transducer module 200 permits a treatment sequence at a fixed depth at or below the skin surface. In one embodiment, a transducer module permits a treatment sequence at one, two, or more variable or fixed depths below the dermal layer. In several embodiments, the transducer module comprises a movement mechanism adapted to and/or configured to direct ultrasonic treatment in a sequence of individual thermal lesions (hereinafter "thermal coagulation points" or "TCPs") at a fixed focal depth. In one embodiment, the sequence of individual TCPs has a treatment spacing in a range from about 0.01 mm to about 25 mm (e.g., 1 mm, 1.5 mm, 2 mm, 2.5 mm, 3 mm, 5 mm, 10 mm, 20 mm and any value ranges therein), with a dithering alteration of the spacing by 1-50% (e.g., 1%, 5%, 10%, 15%, 20%, 25%, 30%, 35%, 40%, 45%, 50% and any range therein). For example, the spacing can be 1.1 mm or less, 1.5 mm or more, between about 1.1 mm and about 1.5 mm, etc. In one embodiment, the individual TCPs are discrete. In one embodiment, the individual TCPs are overlapping. In one embodiment, the movement mechanism is adapted to and/or configured to be programmed to provide variable spacing between the individual TCPs. In one embodiment, the dithering can be adapted to and/or configured to provide variable spacing between the individual TCPs. In several embodiments, a transducer module comprises a movement mechanism adapted to and/or configured to direct ultrasonic treatment in a sequence so that TCPs are formed in linear or substantially linear sequences separated by a treatment distance. For example, a transducer module can be adapted to and/or configured to form TCPs along a first linear sequence and a second linear sequence separated by a treatment distance from the first linear sequence. In one embodiment, treatment distance between adjacent linear sequences of individual TCPs is in a range from about 0.01 mm to about 25 mm. In one embodiment, treatment distance between adjacent linear sequences of individual TCPs is in a range from about 0.01 mm to about 50 mm. For example, the treatment distance can be 2 mm or less, 3 mm or more, between about 2 mm and about 3 mm, etc. In several embodiments, a transducer module can comprise one or more movement mechanisms 400 adapted to and/or configured to direct ultrasonic treatment in a sequence so that TCPs are formed in linear or substantially linear sequences of individual thermal lesions separated by a treatment distance from other linear sequences. In one embodiment a treatment is applied in a first direction 290 (e.g., push). In one embodiment, a treatment is applied opposite the first direction 290 (e.g., pull). In one embodiment, treatment is applied in both a first direction 290 and opposite the . . . first direction (e.g., push and pull). In one embodiment, the treatment distance separating linear or substantially linear TCPs sequences is the same or substantially the same. In one embodiment, the treatment distance separating linear or substantially linear TCPs sequences is different or substantially different for various adjacent pairs of linear TCPs sequences.

In one embodiment, first and second removable transducer modules are provided. In one embodiment, each of the first and second transducer modules are adapted to and/or configured for both ultrasonic imaging and ultrasonic treatment. In one embodiment, a transducer module is adapted to and/or configured for treatment only. In one embodiment, an imaging transducer may be attached to a handle of a probe or a hand wand. The first and second transducer modules are adapted to and/or configured for interchangeable coupling to a hand wand. The first transducer module is adapted to and/or configured to apply ultrasonic therapy to a first layer of tissue, while the second transducer module is adapted to and/or configured to apply ultrasonic therapy to a second layer of tissue. The second layer of tissue is at a different depth than the first layer of tissue.

As illustrated in FIG. 3, in various embodiments, delivery of emitted energy 50 at a suitable focal depth 278, distribution, timing, and energy level is provided by the module 200 through controlled operation by the control system 300 to achieve the desired therapeutic effect of controlled thermal injury to treat at least one of the epidermis layer 502, dermis layer 503, fat layer 505, the SMAS layer 507, the muscle layer 509, and/or the hypodermis 504. FIG. 3 illustrates one embodiment of a depth that corresponds to a depth for treating muscle. In various embodiments, the depth can correspond to any tissue, tissue layer, skin, epidermis, dermis, hypodermis, fat, SMAS, muscle, blood vessel, nerve, or other tissue. During operation, the module 200 and/or the transducer 280 can also be mechanically and/or electronically scanned along the surface 501 to treat an extended area. Before, during, and after the delivery of ultrasound energy 50 to at least one of the epidermis layer 502, dermis layer 503, hypodermis 504, fat layer 505, the SMAS layer 507 and/or the muscle layer 509, monitoring of the treatment area and surrounding structures can be provided to plan and assess the results and/or provide feedback to the controller 300 and the user via a graphical interface 310.

In one embodiment, an ultrasound system 20 generates ultrasound energy which is directed to and focused below the surface 501. This controlled and focused ultrasound energy 50 creates the thermal coagulation point or zone (TCP) 550. In one embodiment, the ultrasound energy 50 creates a void in subcutaneous tissue 510. In various embodiments, the emitted energy 50 targets the tissue below the surface 501 which cuts, ablates, coagulates, microablates, manipulates, and/or causes a TCP 550 in the tissue portion 10 below the surface 501 at a specified focal depth 278. In one embodiment, during the treatment sequence, the transducer 280 moves in a direction denoted by the arrow marked 290 at specified intervals 295 to create a series of treatment zones 254 each of which receives an emitted energy 50 to create one or more TCPs 550. In one embodiment, an arrow marked 291 illustrates an axis or direction that is orthogonal or parallel to arrow 290, and a spacing of TCP's 550 show TCP's can be spaced orthogonally or parallel to the motion direction of the transducer 280. In some embodiments, an orientation of the spaced TCP's can be set at any angle 0-180 degrees from arrow 290. In some embodiments, an orientation of the spaced TCP's can be set at any angle 0-180 degrees based on the orientation of poled areas on the transducer 280.

In various embodiments, transducer modules can comprise one or more transduction elements. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In various embodiments, in addition to, or instead of, a piezoelectrically active material, transducer modules can comprise any other materials adapted to and/or configured for generating radiation and/or acoustical energy. In various embodiments, transducer modules can be adapted to and/or configured to operate at different frequencies and treatment depths. Transducer properties can be defined by an outer diameter ("OD") and focal length ($F_L$). In one embodiment, a transducer can be adapted to and/or configured to have OD=19 mm and $F_L$=15 mm. In other embodiments, other suitable values of OD and $F_L$ can be used, such as OD of less than about 19 mm, greater than about 19 mm, etc. and $F_L$ of less than about 15 mm, greater than about 15 mm, etc. Transducer modules can be adapted to and/or configured to apply ultrasonic energy at different target tissue depths. As described above, in several embodiments, transducer modules comprise movement mechanisms adapted to and/or configured to direct ultrasonic treatment in a linear or substantial liner sequence of individual TCPs with a treatment spacing between individual TCPs. For example, treatment spacing can be about 1.1 mm, 1.5 mm, etc. In several embodiments, transducer modules can further comprise movement mechanisms adapted to and/or configured to direct ultrasonic treatment in a sequence so that TCPs are formed in linear or substantially linear sequences separated by a treatment spacing. For example, a transducer module can be adapted to and/or configured to form TCPs along a first linear sequence and a second linear sequence separated by treatment spacing between about 2 mm and 3 mm from the first linear sequence. In one embodiment, a user can manually move the transducer modules across the surface of a treatment area so that adjacent linear sequences of TCPs are created. In one embodiment, a movement mechanism can automatically move the transducer modules across the surface of a treatment area so that adjacent linear sequences of TCPs are created.

Aperture Spatial Frequency Analysis and Fourier Transform

In various embodiments, spatial frequency analysis techniques based on Fourier analysis and Fourier optics can be used to increase efficiency of therapeutic treatment. When a system that has an impulse response h (t) is excited by a stimulus x(t), the relationship between the input x(t) and output y (t) is related by the convolution function as follows:

$$y(t)=x(t)*h(t)=\int_{-\infty}^{\infty}x(\tau)h(t-\tau)d\tau \quad (1):$$

In various embodiments, Fourier transform can be applied to compute the convolution of equation (1). Continuous one-dimensional Fourier transform can be defined as:

$$Y(f)=F(y(t)=\int_{-\infty}^{\infty}y(t)e^{-j2\pi ft}dt) \quad (2)$$

here f is frequency, t is time. It can be shown that convolution in the time domain is equivalent to multiplication in the frequency domain:

$$F(x(t)*h(t))=X(f)H(f)=Y(f) \quad (3)$$

In various embodiments, the Fraunhofer approximation can be used for deriving a relationship between a transducer opening or aperture and a resulting ultrasonic beam response. Derivation of the Fraunhofer approximation is described in Joseph Goodman, Introduction to Fourier Optics (3d ed. 2004), which is incorporated in its entirety by reference, herein. According to the Fraunhofer approximation, a far-field complex amplitude pattern produced by a complex aperture is equal to a two-dimensional Fourier transform of the aperture amplitude and phase. In several embodiments, this relationship in optics can be extended to ultrasound since linear wave equations can be used to represent both light propagation and sound propagation. In the case of optics and/or ultrasound, the two-dimensional Fourier transform can determine a sound wave pressure amplitude distribution at the focus of a transducer.

For a focused system, the variable z which represents depth can be replaced with $z_f$ which represents a focal distance.

$$f_x = x_0/\lambda z_f \quad (4a)$$

$$f_y = y_0/\lambda z_f \quad (4b)$$

In various embodiments, Fourier optics and Fourier transform identities (some of which are listed in Table 1, below) can be used for ultrasound transducers in order to determine the intensity distribution corresponding to a transducer design. For example, Fourier transform of a rectangle rect (ax) is a sinc function. As another example, Fourier transform of a two dimensional circle of uniform amplitude is a first order Bessel function which can be represented as $J_1$.

TABLE 1

| | Aperture Function | Fourier Transform |
|---|---|---|
| 1 | rect(ax) | $\frac{1}{a}sinc\left(\frac{\xi}{a}\right)$ |
| 2 | $\delta(x)$ | 1 |
| 3 | cos(ax) | $\delta\left(\xi - \frac{a}{2\pi}\right) + \delta\left(\xi + \frac{a}{2\pi}\right)$ |
| 4 | sin(ax) | $\delta\left(\xi - \frac{a}{2\pi}\right) - \delta\left(\xi + \frac{a}{2\pi}\right)$ |
| 5 (two-dimensional transform pair) | $circ(\sqrt{x^2+y^2})$ | $\frac{J_1\left(2\pi\sqrt{\xi_x^2+\xi_y^2}\right)}{\sqrt{\xi_x^2+\xi_y^2}}$ |
| 6 | f(x) * g(x) | $f(\xi)G(\xi)$ |
| 7 | f(x)g(x) | $F(\xi) * G(\xi)$ |

In several embodiments, an ultrasound transducer can have a rectangular aperture of suitable dimensions and focal length. In several embodiments, an ultrasound transducer can have a circular aperture with suitable dimensions and focal length. In one embodiment, a transducer can have a circular aperture with an outer radius of approximately 9.5 mm, an inner diameter of approximately 2 mm, and focal length of approximately 15 mm. The aperture of a circular transducer may be described as:

$$f(x, y) = circ\left(\frac{r}{a}\right) - circ\left(\frac{r}{b}\right) \quad (5a)$$

$$r = \sqrt{x^2 + y^2} \quad (5b)$$

For example, in one embodiment, the variable 'a' can be approximately 9.5 mm and the variable 'b' in equation (5a) can be approximately 2 mm. Applying Fourier transform to equation (5a) can provide an estimate of the sound wave pressure distribution at the focus.

$$F_{x,y}(f(x, y)) = F(\xi_x, \xi_y) = \frac{aJ_1\left(2\pi a\sqrt{\xi_x^2+\xi_y^2}\right)}{\sqrt{\xi_x^2+\xi_y^2}} - \frac{bJ_1\left(2\pi b\sqrt{\xi_x^2+\xi_y^2}\right)}{\sqrt{\xi_x^2+\xi_y^2}} \quad (6)$$

where $\xi_x$ and $\xi_y$ are same as $f_x$ and $f_y$ of equations (4a) and (4b). Equation (6) demonstrates that the sound wave pressure distribution of a transducer with a circular aperture is a first order Bessel function. In one embodiment, a substantial majority of the energy is concentrated at the focus (e.g., 15 mm away from the aperture). The width of a main ultrasonic beam and the distribution of energy away from the main beam can be expressed as a function of the operating frequency as is expressed in equations (4a) and (4b).

In various embodiments, two identical or nearly identical beams could be created at the focus if the aperture was modulated (e.g., multiplied) by a correct function. In one embodiment, a cosine function can be applied to a circular aperture as follows:

$$g(x, y) = \cos(cx)\left(circ\left(\frac{r}{a}\right) - circ\left(\frac{r}{b}\right)\right) \quad (7)$$

An energy distribution or beam response at the focus of the modulated aperture of equation (7) is the convolution of the Fourier transform of the two functions of the aperture:

$$G(\xi_x, \xi_y) = \left(\frac{\delta\left(\xi_x - \frac{c}{2\pi}\right) + \delta\left(\xi_x + \frac{c}{2\pi}\right)}{2}\right) * F(\xi_x, \xi_y) \quad (8)$$

Equation (8) can be simplified into the summation of two separate functions applying the Fourier Transform identity for a Dirac delta function (e.g., identity 2 in Table 2):

$$G(\xi_x, \xi_y) = \frac{1}{2}\left(F\left(\xi_x - \frac{c}{2\pi}, \xi_y\right) + F\left(\xi_x + \frac{c}{2\pi}, \xi_y\right)\right) \quad (9)$$

Equation (9) shows that two beams appearing at the focus are spatially shifted by $$\pm\frac{c}{2\pi}$$

compared to the original, non-modulated beam. In several embodiments, one or more other modulation functions, such as sine function, can be used to achieve a desired beam response. In several embodiments, aperture can be modulated such that more than two foci are created. For example, three, four, five, etc. foci can be created. In several embodiments, aperture can be modulated such that foci are created sequentially or substantially sequentially rather than simultaneously.

In several embodiments, therapy transducer modules comprise movement mechanisms configured to direct ultrasonic treatment in a linear or substantial liner sequence of individual TCPs with a treatment spacing between individual TCPs. For example, treatment spacing can be about 1.1 mm, 1.5 mm, etc. In several embodiments, transducer modules can further comprise movement mechanisms configured to direct ultrasonic treatment in a sequence so that TCPs are formed in linear or substantially linear sequences separated by a treatment spacing. For example, a transducer module can be configured to form TCPs along a first linear sequence and a second linear sequence separated by treatment spacing between about 2 mm and 3 mm from the first linear sequence. According to equation (9), a simultaneous or substantially simultaneous split in the ultrasonic beam may be achieved at the focus (or before the focus) if the aperture is modulated by a cosine and/or sine function of a desired spatial frequency. In one embodiment, two simultaneous or nearly simultaneous focused beams separated by about 1.1 mm treatment spacing can be created in a linear or substantially linear sequence. At 7 MHz frequency of ultrasound, the wavelength $L$ of ultrasound wave in water is approximately 0.220 mm. Accordingly, spatial frequencies $\xi_x$ and $\xi_y$ at the focus are represented as:

$$\xi_x = \frac{x_0}{15 * 0.220} = \frac{x_0}{3.3} \quad (10a)$$

$$\xi_y = \frac{y_0}{15 * 0.220} = \frac{y_0}{3.3} \quad (10b)$$

In order to place two foci separated by about 1.1 mm, then the spatial frequency for modulating the aperture is calculated as follows. Using identities 3 and 4 in Table 2, the Fourier transformation of a sine or cosine function is a Dirac delta function with the argument:

$$\arg = \frac{x_0}{3.3} - \frac{k_x}{2\pi} \quad (11a)$$

In one embodiment, equation (11a) can solved for $k_x$ when argument is 0:

$$k_x = \frac{2\pi x_0}{3.3} \quad (11b)$$

Further, $x_0$ can be replaced by half of the separation distance (e.g., 1.1 mm):

$$k_x = \frac{2\pi \frac{s}{2}}{z_f \lambda} = \frac{2\pi \frac{1.1}{2}}{3.3} = 1.04 nun^{-1} \quad (11c)$$

In several embodiments, a transducer with circular aperture emitting ultrasonic energy at various operating frequencies can be modulated by a sine and/or cosine functions at spatial frequencies listed in Table 2. Modulated aperture of the transducer can produce a simultaneously or substantially simultaneously split beam with two foci having different separation distances, as is indicated in Table 2. In one embodiment, the transducer can have OD of about 19 mm and a focal length of about 15 mm.

TABLE 2

| Ultrasound Frequency | Separation Distance Between Foci | | | |
|---|---|---|---|---|
| | 1.1 mm | 1.5 mm | 2 mm | 3 mm |
| 4 MHz | 0.60 | 0.82 | 1.09 | 1.63 |
| 7 MHz | 1.04 | 1.43 | 1.90 | 2.86 |
| 10 MHz | 1.50 | 2.04 | 2.72 | 3.08 |

As is shown in Table 2, in several embodiments, a spatial frequency of an aperture modulation function increases as the ultrasonic operating frequency increases for a given foci separation distance. In addition, the spatial frequency increases as the desired foci separation distance increases.

In one embodiment, higher spatial frequency can result in amplitude transitions in the aperture occurring more rapidly. Due to transducer processing limitations, rapid amplitude variations in the aperture can make the aperture less efficient as there may be a variance in an amount of sound pressure produced by different parts of the aperture. In one embodiment, using spatial frequencies to simultaneously or nearly simultaneously split the beam can reduce the overall focal gain of each beam. As is shown in equation (9), a field pressure at the focus of each beam is reduced by a factor of two in comparison with an unmodulated beam. In one embodiment, the sound pressure or ultrasound intensity from the aperture can be increased to obtain similar or substantially similar intensities at the focal plane. However, in one embodiment, increasing the pressure at the aperture may not be limited by system and/or transducer processing limitations. In one embodiment, an increase in the pressure at the aperture can increase the overall intensity in the near field, which may increase the possibility of excessively heating treatment area tissue(s) that is located before focus. In one embodiment, the possibility of additional heating of the pre-focal tissue(s) may be limited or eliminated by using a lower ultrasound treatment frequency.

In one embodiment, applying aperture modulation function as is shown in equation (7) results in two simultaneous or substantially simultaneous ultrasound beams at the focus. In various embodiments, ultrasound beam can be split multiple times, such as three, four, five, etc. times, such that multiple simultaneous or nearly simultaneous beams are created. In one embodiment, four equally spaced beams along one dimension can be generated by modulating or multiplying the aperture by two separate spatial frequencies:

$$g(x, y) = (\cos(cx) + \cos(dx))\left(circ\left(\frac{r}{a}\right) - circ\left(\frac{r}{b}\right)\right) \quad (12a)$$

$$G(\xi_x, \xi_y) = \frac{1}{2} \quad (12b)$$

$$\left(F\left(\xi_x - \frac{c}{2\pi}, \xi_y\right) + F\left(\xi_x + \frac{c}{2\pi}, \xi_y\right) + F\left(\xi_x - \frac{d}{2\pi}, \xi_y\right) + F\left(\xi_x + \frac{d}{2\pi}, \xi_y\right)\right)$$

As is shown in equation (12b), unmodulated beam at the focus can be created at four different locations along the x-axis. In one embodiment, a constant or DC term, C1, may be added to the amplitude modulation function to maintain placement of energy at the original focal location:

$$g(x, y) = (\cos(cx) + \cos(dx) + C_1)\left(circ\left(\frac{r}{a}\right) - circ\left(\frac{r}{b}\right)\right) \quad (13a)$$

$$G(\xi_x, \xi_y) = \frac{1}{2}\left(F\left(\xi_x - \frac{c}{2\pi}, \xi_y\right) + F\left(\xi_x + \frac{c}{2\pi}, \xi_y\right) + F\left(\xi_x - \frac{d}{2\pi}, \xi_y\right) + F\left(\xi_x + \frac{d}{2\pi}, \xi_y\right)\right) + C_1 F(\xi_x, \xi_y) \quad (13b)$$

In one embodiment, aperture modulation of equations (12) and (13), whereby the beam can be placed at multiple locations simultaneously or nearly simultaneously, may be have limited applicability due to system, material, and/or tissue limitations. In one embodiment, due to the possibility of heating treatment area tissue(s) located before focus, the frequency of ultrasound therapy may be adjusted, such as lowered, in order to limit and/or eliminate such possibility. In one embodiment, nonlinear techniques can be applied at the focus in order to limit and/or eliminate the possibility of heating of the pre-focal tissue(s). In one embodiment, the sound pressure or ultrasound intensity from the aperture can be increased to obtain similar or substantially similar intensities at the focal plane.

In various embodiments, if the amplitude and phase functions at the aperture are separable, the two-dimensional Fourier transform of a sound pressure function $U(x_1, y_1)$ can be expressed as a product of a one-dimensional Fourier transform of two functions in x and y. In various embodiments, it may be advantageous to create multiple TCPs in a linear or substantially linear sequence as well as to create multiple linear sequences simultaneously or nearly simultaneously.

Electronic Dithering of Multiple Beam Splitting Apertures Using Frequency Modulation In various embodiments, Table 2 illustrates aperture spatial frequency for achieving a specific distance between two simultaneous foci for a given operational frequency (e.g. in various embodiments, 4 MHZ, 7 MHz, 10 MHz). Equation (11c) shows that the separation distance between the foci is also a function operational frequency. For example, in one embodiment the spatial frequency of the aperture ($k_x$) is fixed to 1.0 mm$^{-1}$ and the operational frequency is allowed to vary. Equation 11c can be rewritten to show how the foci separation distance can be modulated through operation frequency.

$$S = (k_x z_f v_c)/(\pi f_{op}) \quad (14)$$

where $k_x$ is the spatial frequency in mm$^{-1}$, $z_f$ is the focal depth of the aperture in mm, $v_c$ is the velocity of ultrasound in the propagating medium (e.g. water) in mm/☐sec and $f_{op}$ is the operational frequency of the aperture in MHz. In one embodiment, the following substitution is made in equation 11c:

$$\pi = v_c/f_{op} \quad (15)$$

As Equation (14) shows, the separation distance of the foci is a function of the operational frequency. Further, the rate in change of the separation distance to the operational frequency is:

$$ds/df_{op} = -(k_x z_f v_c)/(\pi f_{op}^2) \quad (16)$$

Equation (16) shows that the separation distance decreases as the operational frequency increases. Table 3 (below) shows the rate in change of separation distance as a function of operational frequency for the different spatial frequencies (e.g., in various embodiments, 4 MHz, 7 MHz, 10 MHz).

TABLE 3

| Ultrasound Frequency | Derivative of Equation (16) [mm/MHz] | | | |
|---|---|---|---|---|
| | 1.1 mm | 1.5 mm | 2 mm | 3 mm |
| 4 MHz | −0.269 | −0.367 | −0.488 | −0.730 |
| 7 MHz | −0.152 | −0.209 | −0.278 | −0.418 |
| 10 MHz | −0.107 | −0.146 | −0.195 | −0.221 |

As shown in Table 3, as the operational frequency increases, the foci get closer together and as the operational frequency decreases the foci get farther apart without the need to change the phase or mechanically move the transducer. This is a unique method of electronically moving the beam to spread the energy without relying on thermal conduction in tissue. The benefits include a reduction or a minimization of the maximum temperature and an increase in the thermal coagulation volume of the lesion without the need for additional system channels.

The amount of movement from a main operational frequency can be determined by using equation (14). In one embodiment, the main operational frequency of an aperture is 5 MHz and the focal length is 15 mm. In some embodiments, the operational frequency is called the aperture center frequency. In one embodiment, the operational frequency is 5 MHz. In one embodiment, Table 4 at FIG. 5 shows the amount of foci separation for apertures with different spatial frequencies ($k_x$=0.5, 1.0, 1.5, 2.0 in mm$^{-1}$) as designed for a center frequency of 5 MHz. It also calculates the amount of spread from the foci of the center frequency at 5 MHz. According to one embodiment, the spacing decreases for higher frequencies relative to 5 MHz and increases for lower frequencies relative to 5 MHz.

Figure 6:
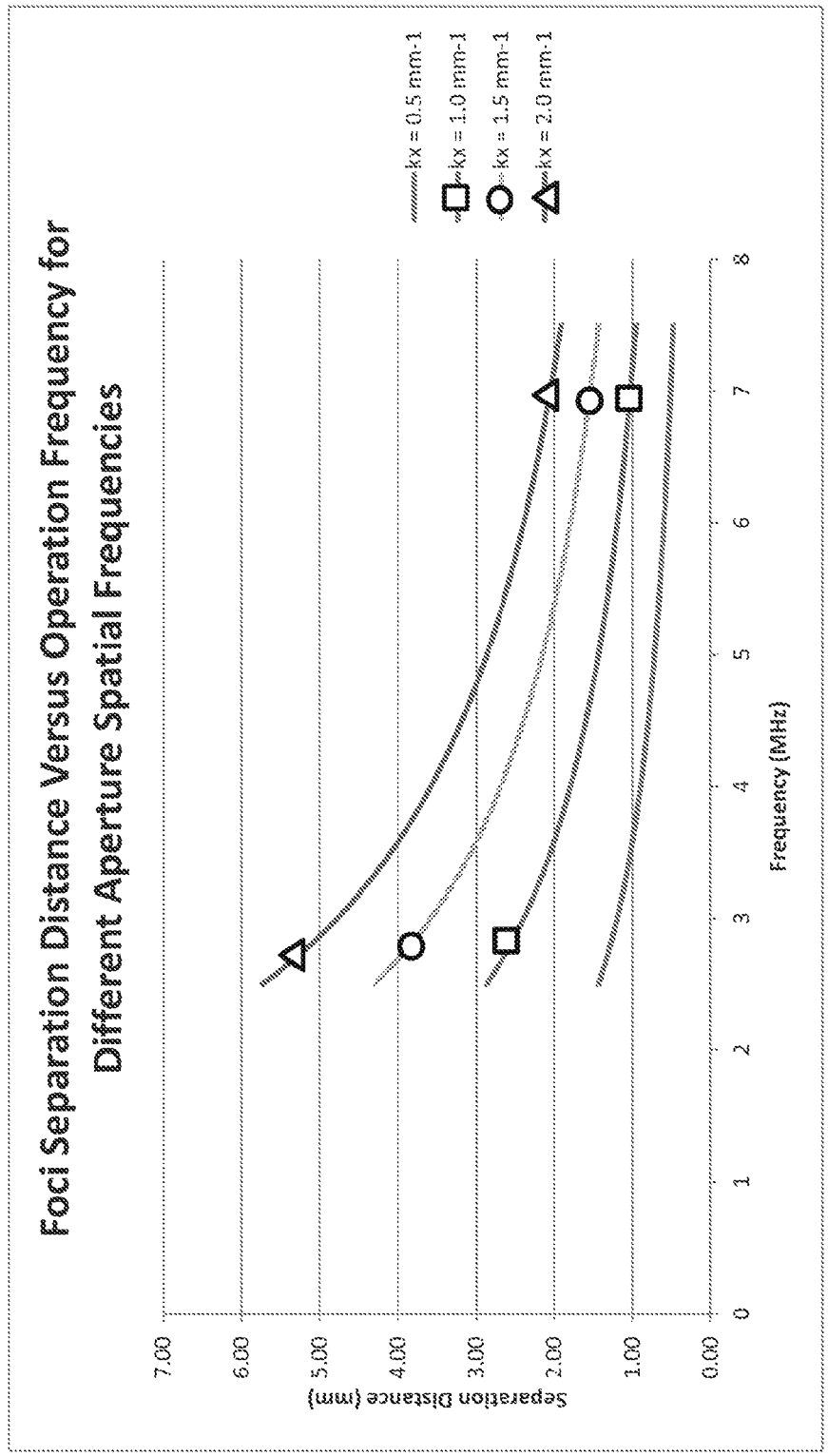
FIG. 6 is plot illustrating foci separation for apertures with different aperture spatial frequencies according to various embodiments of the present invention.

FIG. 6 shows the spacing difference for all operational frequencies of the aperture for different aperture spatial frequencies. As FIG. 6 shows, the separation distance increases as the frequency decreases.

Figure 7:
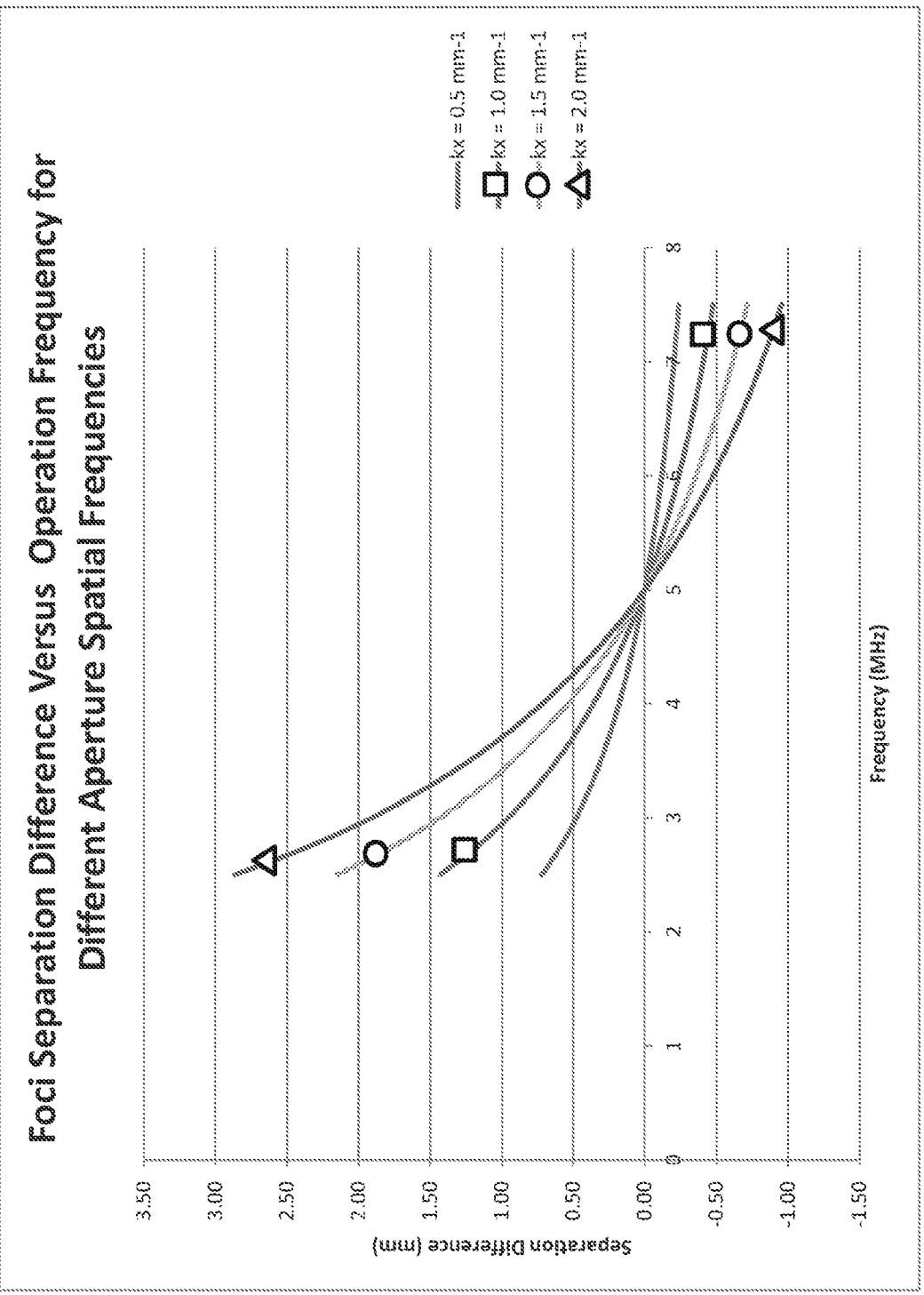
FIG. 7 is plot illustrating foci separation for apertures with different aperture spatial frequencies according to various embodiments of the present invention.

In one embodiment, the separation distance is relative to a frequency 5 MHz. In one embodiment, one way to estimate the electronic dithering from frequency modulation can be determined by referencing all movement to the initial separation at 5 MHz. As FIG. 7 shows, the spread of the separation distance between the foci can easily vary by over 1 mm.

In various embodiments, the range of possible operational frequencies from one aperture can be described in terms of the transducer bandwidth. In one embodiment, a larger transducer bandwidth results in an aperture that has a wider range of operational frequencies. Transducer bandwidth can be described as a percent fraction of the aperture center frequency by locating the frequency where the transmit intensity decreases to −3 dB of the peak transmit intensity. In one embodiment the −3 dB high frequency is designated as $f_{-3db,H}$ and the −3 dB low frequency is designated as $f_{-3dB,L}$ for the transmit response of a transducer aperture. The −3 dB center frequency in [MHz] is described as:

$$f_{-3dB,center} = (f_{-3dB,H} + f_{-3dB,L})/2 \quad (17)$$

The −3 dB percent bandwidth is described as:

$$BW_{-3dB} = 100\% * (f_{-3dB,H} - f_{-3dB,L})/((f_{-3dB,H} + f_{-3dB,L})/2) \quad (18)$$

In some embodiments, increasing the range of operational frequencies possible within one aperture may be achieved (but not limited to) by the use of backing layers, matching layers, multiple piezoelectric layers, electrical matching, piezoelectric composites, and/or a single crystal piezoceramic. In one embodiment, as the transducer bandwidth increases, the range of possible separation distance increases. Table 5 (below) shows how based on percent bandwidth the foci spread can vary if the aperture center frequency is 5 MHz. The foci separation distance for 5 MHz is 0.72 mm, 1.43 mm, 2.15 mm and 2.86 mm respectively for spatial frequencies of 0.5 mm$^{-1}$, 1.00 mm$^{-1}$, 1.50 mm$^{-1}$, 2.00 mm$^{-1}$. If the spatial frequency at the aperture is 1.50 mm$^{-1}$ and the transducer bandwidth is 60%, then the separation distance between the foci varies by 1.42 mm which is a distance greater than the lateral resolution of the beam at 5 MHz.

TABLE 5

Additional Spread from 5 MHz Center Frequency in [mm]

| Bandwidth | $k_x = 0.5$ mm$^{-1}$ | $k_x = 1.0$ mm$^{-1}$ | $k_x = 1.5$ mm$^{-1}$ | $k_x = 2.0$ mm$^{-1}$ |
|---|---|---|---|---|
| 20% | 0.14 | 0.29 | 0.43 | 0.58 |
| 40% | 0.30 | 0.60 | 0.90 | 1.19 |
| 60% | 0.47 | 0.94 | 1.42 | 1.89 |
| 80% | 0.68 | 1.36 | 2.05 | 2.73 |
| 100% | 0.95 | 1.91 | 2.86 | 3.82 |

In one embodiment, as the frequency is changed, the depth-of-field will also change as well as lateral resolution and focal gain. In one embodiment, as the frequency is changed, the depth-of-field, lateral resolution and focal gain will not change. Therefore, in one embodiment, the intensity at the aperture may change depending in the heating rate goals. Also, in some embodiments, it may be advantageous to send multiple operational frequencies at the same time to spread the energy immediately or near-immediately. For example, transmit excitation of the aperture may include excitation at 1.75 MHz, 4 MHZ, 5 MHz and 6 MHz all at the same time.

Multiple Foci By Changing the Aperture Spatial Frequency

Figure 8:
FIG. 8 is a schematic representation of aperture poling with a spatial frequency that can be modified by excitation of channels according to various embodiments of the present invention.

As Equation 14 shows, the higher the aperture spatial frequency, the greater the separation distance between the foci. In one embodiment, an aperture is poled with a spatial frequency of $k_x$. The spatial frequency can be easily doubled or decreased to zero by connecting individual electrical excitation channels that have the ability to modify the phase to 0 degrees or 180 degrees, as shown in the embodiments in FIG. 8. For example, if the phase on channels 1 through 16 is 0 degrees, then the aperture spatial frequency is $k_x$. In an embodiment, as the phase on each channel is varied from 0 degrees to 180 degrees such that odd channels are at 0 degrees and even channels are at 180 degrees, then the spatial frequency at the aperture is ½ $k_x$. In an embodiment, if the phase repeats every two channels such that channel 1 and channel 2 is 0 degrees and channel 3 and channel 4 is 180 degrees and so on, then the spatial frequency at the aperture is 0. If channel 1 is 0 degrees, channel 2 is 180 degrees, channel 3 is 180 degrees, channel 4 is 0 degrees and so on, then the spatial frequency at the aperture is $2k_x$. In this case, seven unique foci can be created. As noted in Table 4 (at FIG. 5), if the aperture center frequency is 5 MHZ, and the aperture frequency is any of 0 mm$^{-1}$, 0.5 mm$^{-1}$, 1.0 mm$^{-1}$, or 2.0 mm$^{-1}$, the corresponding separation distances are 0 mm, 0.72 mm, 1.43 mm and 2.86 mm, which yield seven unique focal positions separated by 0.36 mm. In various embodiments, intermediate phases between 0 degrees and 180 degrees would further allow the two foci to be tilted such that a line of foci could be created at the focal plane. Ultimately, the tilting, modulation of focal position, and frequency modulation enables the heating and possible coagulation of an entire line with a length of approximately 2.86 mm.

Figure 9:
FIG. 9 is a schematic representation of a poled ceramic with a spatial frequency that can be modified by excitation of channels covering two poled areas of the ceramic according to various embodiments of the present invention.

In one embodiment, a poled ceramic has a spatial frequency of $2k_x$, as shown in FIG. 9. In this case, each electrical channel covers two poled areas in the ceramic (e.g., a piezoceramic). If channel 1 through channel 8 have the same electrical phase, then the spatial frequency of the aperture is $2k_x$. If the phase alternates such that odd channels have a phase of 0 degrees and even channels have a phase of 180 degrees, then the spatial frequency of the aperture is $k_x$. In one embodiment, this configuration of only two phases are possible on the channels enables four unique foci. In various embodiments, if additional phases are allowable then it is possible to tilt the two foci to many different focal positions. This configuration limits the number of required electronic channels to get multiple foci positions.

In several embodiments, a treatment system utilizes multiple therapy channels to enable electronic focusing and/or steering. For example, a treatment system that utilizes multiple therapy channels to enable electronic focusing and/or steering allows for faster electronic dithering to either create more thermal coagulation using the same amount of energy as other treatment devices or equal thermal coagulation using electronic dithering with less energy than other treatment devices. This technique broadens the efficacy and comfort continuum that the device offers. In addition to electronic dithering, the multiple therapy channels also offer the possibility to move the beam to different depth locations such that two conventional transducers such as the DS7-4.5 (7 MHz at 4.5 mm depth) and DS7-3.0 (7 MHz at 3.0 mm depth) could be replaced by one single device that moves between the two different depths.

In one embodiment, a transducer 280 with multiple therapy channels 281 connected to move the beam axially (e.g. annular array) would typically create a TCP 550 at a deep depth first and then move to the shallower depth. In another embodiment, a TCP 550 is created at a shallow depth and then at a deeper depth below the skin surface. This creates the TCP 550 sequentially and would cause the treatment time to be extended. For example, in one embodiment, if the time for the deep TCP 550 is $t_{deep}$ and the time for the shallow TCP 550 is $t_{shallow}$, then the total treatment time for the two TCPs 550 is the sum of the two treatment times, $t_{deep}$ plus $t_{shallow}$. In one embodiment, total treatment time is reduced by forming multiple (two, or more) TCP's 550 simultaneously using signal mixing techniques which uses both signal apodization (shading) and phase control at each channel. In one embodiment, the total treatment time is the maximum of $t_{deep}$ and $t_{shallow}$:

Treatment time, conventional approach: $t_{treatment} = t_{deep} + t_{shallow}$

Treatment time, signal mixing: $t_{treatment} = \max(t_{deep}, t_{shallow})$

Figure 10:
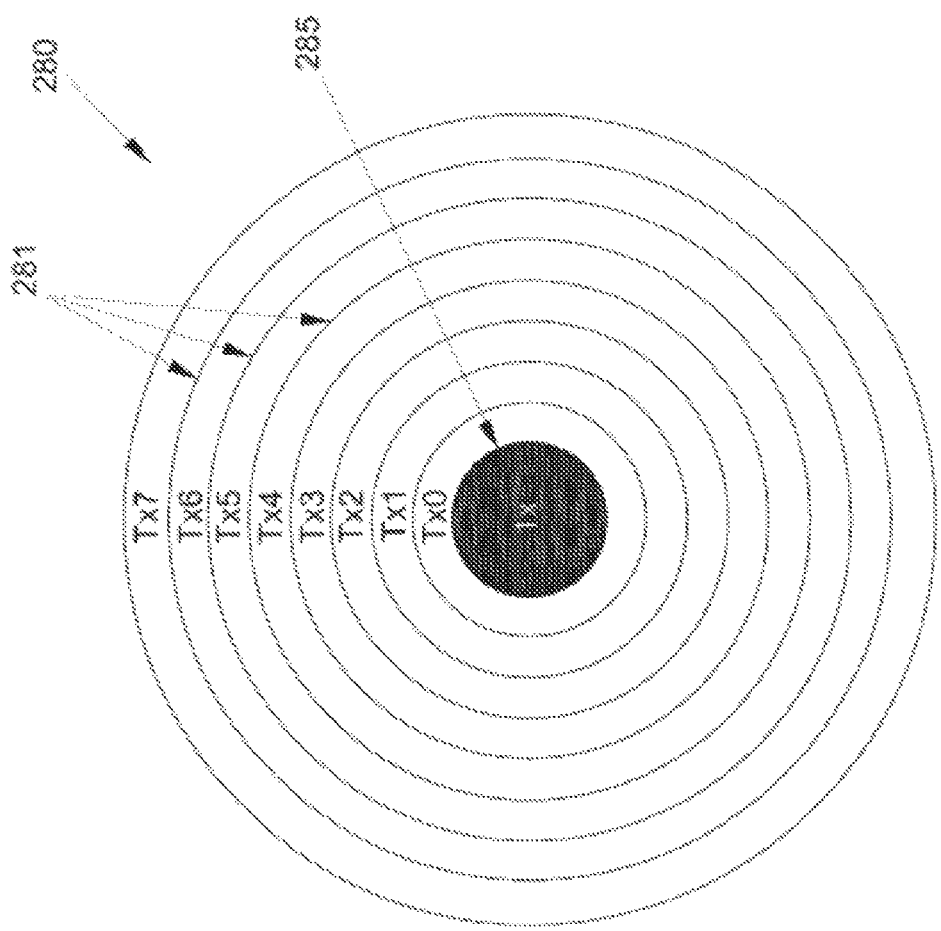
FIG. 10 is a schematic representation of an embodiment of array transducer with an imaging transducer.

In an embodiment, an annular array design 280 enables the electronic movement of the therapy beam in depth (e.g., by changing depth of the TCP 550 below the skin surface). In one embodiment, a transducer 280 includes an eight therapy channel annular transducers elements 281 with a fixed mechanical focus. FIG. 10 shows a top view of one embodiment of this ceramic annular array design 280 with an imaging transducer 285 at the center of the bowl. In this embodiment, the therapy annular transducer 280 has eight rings identified as Tx0 though Tx7, corresponding to the elements 281.

Transducers

In one embodiment, transducer 280 is spherically focused to one or more points. In one embodiment, transducer 280 is cylindrically focused to one or more lines. I Various embodiment of transducer 280 include a flat piezoelectric with a lens. In various embodiments, transducer 280 comprises a convex side 282 and a concave side 283. In various embodiments, a transducer 280 comprises a convex side 282 and a concave side 283 with features that provide for any one or more of variable depth, variable spacing, variable focus positioning, with one, two, three, four, or more simultaneous focus zones. In various embodiments, a transducer 280 is electrically connected to one or more tuning circuits. The tuning circuit improves the electrical signal between the console and the transducer. In various embodiments, one or more tuning circuits is located in the housing of the transducer, in the connection between the transducer and a console, and/or in the console.

Figure 11:
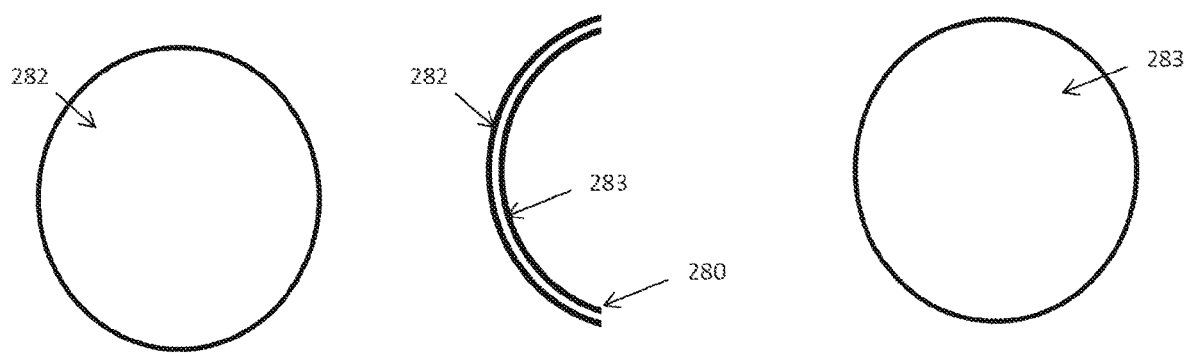
FIG. 11 is schematic views of a transducer as viewed from a convex side, side view cross section, and concave side according to various embodiments of the present invention.
Figure 12:
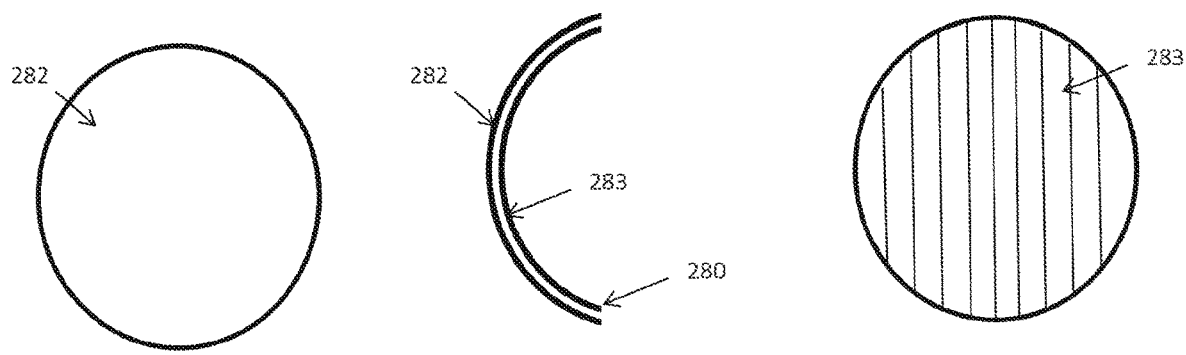
FIG. 12 is schematic views of a transducer as viewed from a convex side, side view cross section, and concave side according to various embodiments of the present invention.

FIG. 11 illustrates an embodiment of a transducer 280 comprising a single element with a convex side 282 and a concave side 283. FIG. 12 illustrates an embodiment of a transducer 280 comprising a solid, coated a convex side 282 and a striped a concave side 283, where the stripes comprise first poled and second poled regions, wherein a poled region is a positive, negative, or unpoled. FIG. 12 illustrates an embodiment of a transducer 280 comprising a solid, coated a convex side 282 and a striped a concave side 283, where the stripes comprise first regions and second regions, wherein a region can comprise a coating or no coating. In one embodiment, a single electrode is provided on the convex surface with poled stripes on concave surface connected to two channels (e.g., FIG. 12). The stripes can alternate to split the beam or include just one phase to mimic the conventional transducer. This would permit one transducer to mimic the treatment of the DS4-4.5S and the DS4-4.5 so three lines can be created with one transducer placement.

Figure 13:
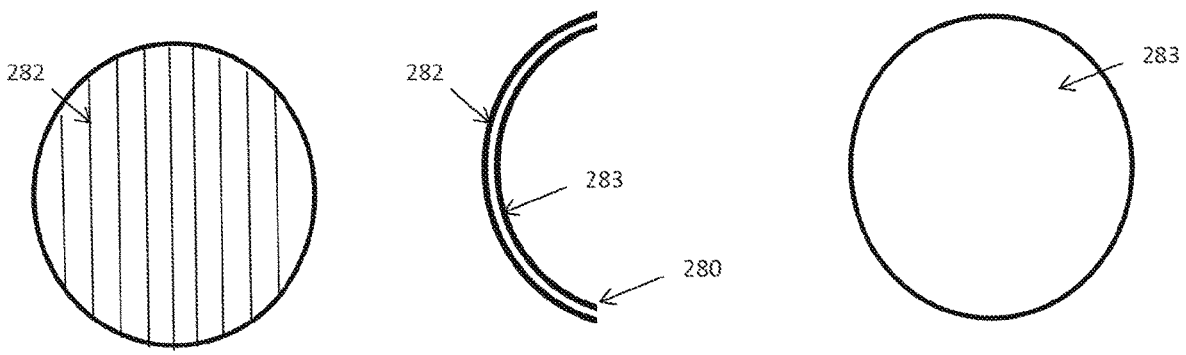
FIG. 13 is schematic views of a transducer as viewed from a convex side, side view cross section, and concave side according to various embodiments of the present invention.

FIG. 13 illustrates an embodiment of a transducer 280 comprising a striped convex side 282 and a solid, coated concave side 283, where the stripes comprise first poled and second poled regions, wherein a poled region is a positive, negative, or unpoled. FIG. 13 illustrates an embodiment of a transducer 280 comprising a striped convex side 282 and a solid, coated concave side 283, where the stripes comprise first regions and second regions, wherein a region can comprising a coating or no coating. In various embodiments, the stripes are electrically connected to a one or more channels. In one embodiment, odd stripes are connected to a first channel and even stripes are connected to a second channel. In one embodiment, the first channel remains at 0° while the second channel alternates between 0° and 180° (or vice versa). Focused ultrasound energy from the first channel remains at a single, central location, which focused ultrasound energy from the second (alternating) channel produces two spaced apart focal zones. Together, the focused ultrasound energy from the first (constant) and second (alternating) channels produces three simultaneous TCP's. In one embodiment, a single electrode is provided on the concave surface with poled stripes on convex surface connected to two channels (e.g., FIG. 13). The stripes can alternate to split the beam or include just one phase to mimic the conventional transducer. This would permit one transducer to mimic the treatment of the DS4-4.5S and the DS4-4.5 so three lines can be created with one transducer placement.

Figure 14:
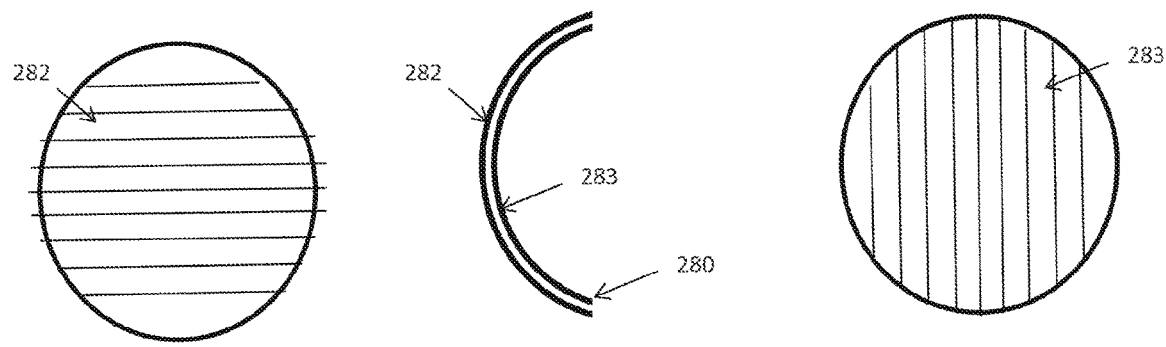
FIG. 14 is schematic views of a transducer as viewed from a convex side, side view cross section, and concave side according to various embodiments of the present invention.

FIG. 14 illustrates an embodiment of a transducer 280 comprising a striped convex side 282 and a striped concave side 283, where the stripes comprise first poled and second poled regions, wherein a poled region is a positive, negative, or unpoled, wherein the striped regions are rotated in an orientation of about 90 degrees with respect to each other. FIG. 14 illustrates an embodiment of a transducer 280 comprising a striped convex side 282 and a solid, coated concave side 283, where the stripes comprise first regions and second regions, wherein a region can comprising a coating or no coating, and wherein the stripes are rotated about 90 degrees with respect to each other.

Figure 15:
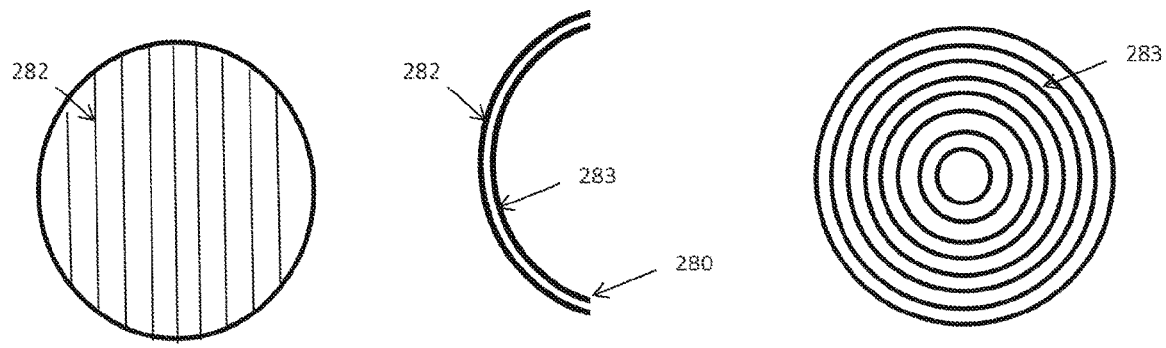
FIG. 15 is schematic views of a transducer as viewed from a convex side, side view cross section, and concave side according to various embodiments of the present invention.

FIG. 15 illustrates an embodiment of a transducer 280 comprising a striped convex side 282 and an annular concave side 283, where the stripes comprise first poled and second poled regions, wherein a poled region is a positive, negative, or unpoled. FIG. 15 illustrates an embodiment of a transducer 280 comprising a striped convex side 282 and an annular concave side 283, where the stripes comprise first regions and second regions, wherein a region can comprising a coating or no coating.

Figure 16:
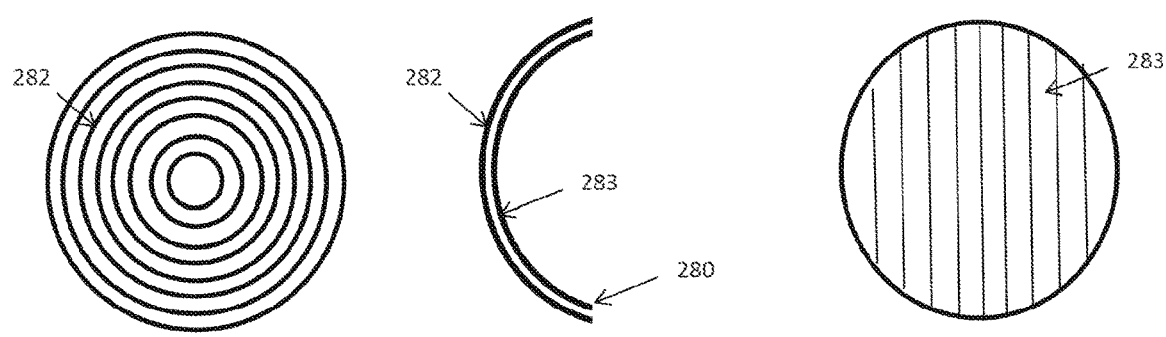
FIG. 16 is schematic views of a transducer as viewed from a convex side, side view cross section, and concave side according to various embodiments of the present invention.

FIG. 16 illustrates an embodiment of a transducer 280 comprising an annular convex side 282 and a striped concave side 283, where the stripes comprise first poled and second poled regions, wherein a poled region is a positive, negative, or unpoled. FIG. 16 illustrates an embodiment of a transducer 280 comprising an annular convex side 282 and a striped concave side 283, where the stripes comprise first regions and second regions, wherein a region can comprising a coating or no coating.

In some embodiments, the system comprises various features that are present as single features (as opposed to multiple features). For example, in one embodiment, the system comprises, consists essentially of, or consists of a single ultrasound transduction element that is adapted to provide two simultaneous treatment zones via dithering. Multiple features or components are provided in alternate embodiments Simultaneous Therapy at Multiple Depths In various embodiments, a treatment system is configured to produces a plurality of regions of micro-coagulation in tissue separated by equal distances along a line of mechanical motion. In various embodiments, a treatment system provides different modules, cartridges, or different transducers (e.g., DS4-4.5, DS7-4.5, DS7-3.0, DS10-1.5, DS7-3.0N, DS10-1.5N, or OT4-4.5, OT7-4.5, OT7-3.0, OT10-1.5, wherein a first number represents the therapy frequency and the second number represents a depth of therapy delivery. The 'N' for the last two transducers designates this device as a narrow transducer which is used in hard to reach areas such as around the nose and mouth. The first four transducers can deliver therapy along a 25 mm line whereas the narrow transducers offer a maximum line length of 14 mm). In various embodiments, a transducer with annular electrodes and poled ceramic enables frequency dithering in lateral dimension, electronic dithering in depth dimension, electronic focusing in depth dimension and a single transducer that can mimic the DS10-1.5 (10 MHz at 1.5 mm depth), DS7-3.0 (7 MHz at 3.0 mm depth), DS7-4.5 (7 MHz at 4.5 mm depth), and DS4-4.5 (4 MHz at 4.5 mm depth) in one transducer. In one embodiment, selectable tuning electronics may be used in combination with composite ceramic to enable the function of the transducer with annular electrodes and poled ceramic enables frequency dithering in lateral dimension, electronic dithering in depth dimension, electronic focusing in depth dimension. In various embodiments, one, two, three, or more selectable tuning circuits help stabilize the signal between the console and the transducer, and can be presented in the transducer housing, between a transducer and a console, or in the console.

In one embodiment a full-face treatment delivers 800 lines of treatment with a transducer involving an operator moving a handpiece along a patient's skin in about 70 to 90 minutes. In one embodiment, a single therapy bowl is configured for the simultaneous delivery of two therapy lines (e.g., DS4-4.5S, DS4-3.0S, OT4-4.5S or OT4-3.0S, which can reduce the treatment delivery time by approximately 40% based on a recent clinical study. In various embodiments, the treatment devices offer a comparable level of efficacy if operated at the correct energy. In various embodiments, a simultaneous treatment reduces the overall pain of a treatment. In one embodiment, a simultaneous treatment time is significantly reduced, it has been hypothesized that the overall pain of the treatment is less.

In various embodiments, a simultaneous treatment will increase a treatment speed by 10%, 20%, 25%, 30%, 40%, 50%, 60% or more. In various embodiments, a simultaneous treatment will reduce a treatment time by 10%, 20%, 25%, 30%, 40%, 50%, 60% or more. In various embodiments, a system is configured to complete a treatment time in 60, 50, 40, 30, 20, or 10 minutes or less.

In one embodiment, a simultaneous treatment system creates two lines simultaneously with the ability to move the depth of the micro-coagulation at thermal coagulation zone 550. In one embodiment, the bandwidth of the therapy transducer is increased, then it is possible to have one device that behaves like two, three, four, five, or six fixed-depth devices. In one embodiment, an 8-channel therapy device is used.

Figure 17:
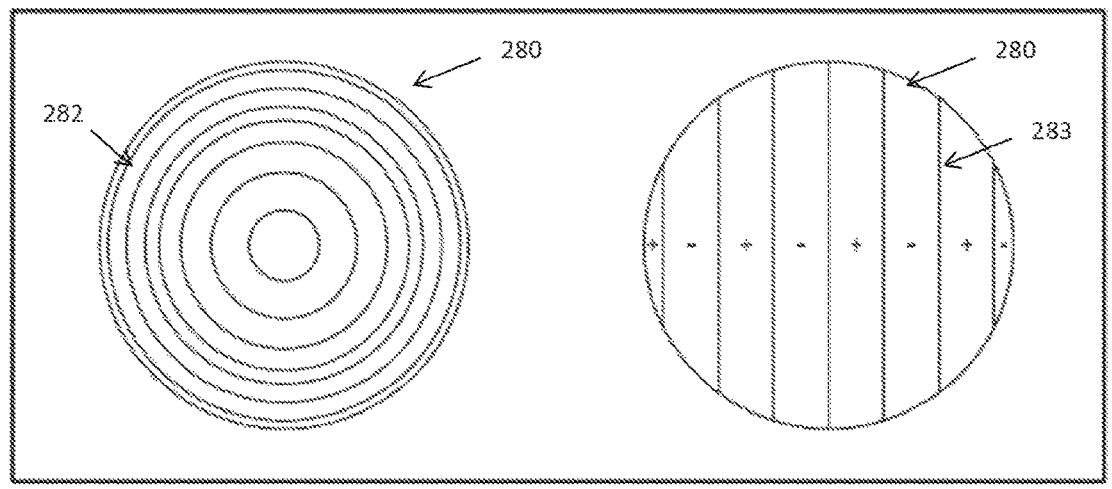
FIG. 17 is a schematic view of a transducer as viewed from a convex side and a concave side according to various embodiments of the present invention.

FIG. 17 illustrates an embodiment of a transducer 280 comprising an annular convex side 282 and a striped concave side 283, where the stripes comprise first poled and second poled regions, wherein a poled region is a positive, negative, or unpoled. FIG. 17 illustrates an embodiment of a transducer 280 comprising an annular convex side 282 and a striped concave side 283, where the stripes comprise first regions and second regions, wherein a region can comprising a coating or no coating. In one embodiment, an annular array coupled with a simultaneous transducer enables two lines of focused ultrasound treatment to be generated simultaneously at different depths 279 (e.g., $D_1, D_2, D_3, \ldots D_N$) below a skin surface. In one embodiment, the stripes on concave side 283 are alternatively poled (e.g., at 0 degrees and 180 degrees, etc.). In various embodiments, depth 279 is 1.5 mm, 3.0 mm, 4.0 mm, 4.5 mm, or 7 mm. In one embodiment, $D_1$=1.5 mm, $D_2$=3.0 mm, and D=4.5 mm. In various embodiments, depth 279 is 0.5 mm, 1.0 mm, 1.5 mm, 2 mm, 3 mm, 4 mm, 4.5 mm, 6 mm, 7 mm, less than 3 mm, between 0.5 mm and 5 mm, between 1.5 mm and 4.5 mm, more than more than 4.5 mm, more than 6 mm, 7 mm, and anywhere in the ranges of 0.1 mm-3 mm, 0.1 mm-4.5 mm, 0.1 mm-25 mm, 0.1 mm-100 mm, and any depths therein (e.g., 6 mm, 7 mm, 10 mm, 13 mm, 15 mm, 17 mm). In an embodiment, a simultaneous treatment at multiple depths creates multiple thermal coagulation zones 550 at various depths 279. FIG. 17 shows the two sides of an embodiment of a simultaneous therapy bowl. On one side of the therapy bowl are stripes that are used to perform alternating poling. In one embodiment, the stripes are on the concave side 283. In one embodiment, the stripes are on the convex side 282. In one embodiment, after the poling is done, the electrode is stripped and a complete electrode is placed over the entire side. In one embodiment, a cold silver electrode may also be used to connect the stripes. In one embodiment, an opposite side of the therapy bowl comprises concentric rings which may or may not be of equal area. The annular array enables beam movement in depth when the correct phasing is applied to the therapy bowl.

Figure 18:
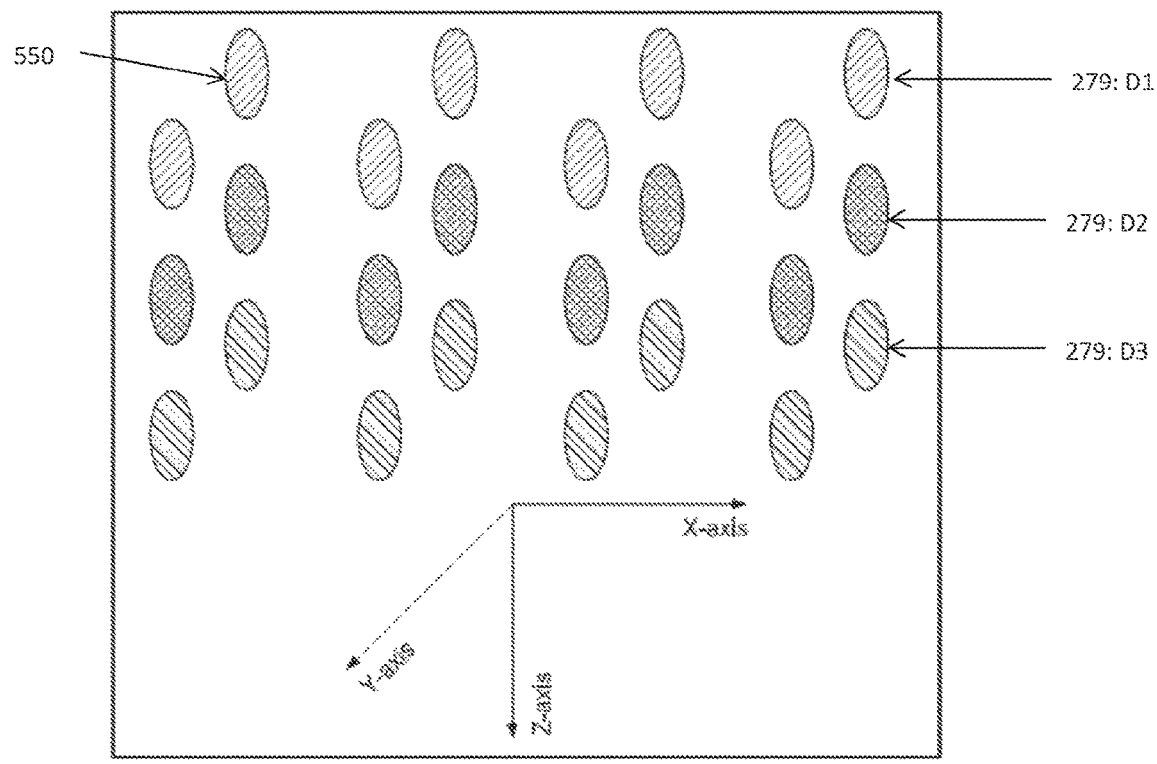
FIG. 18 is a schematic view of multiple thermal coagulation zones at various depths produced by a transducer according to various embodiments of the present invention.
Figure 19:
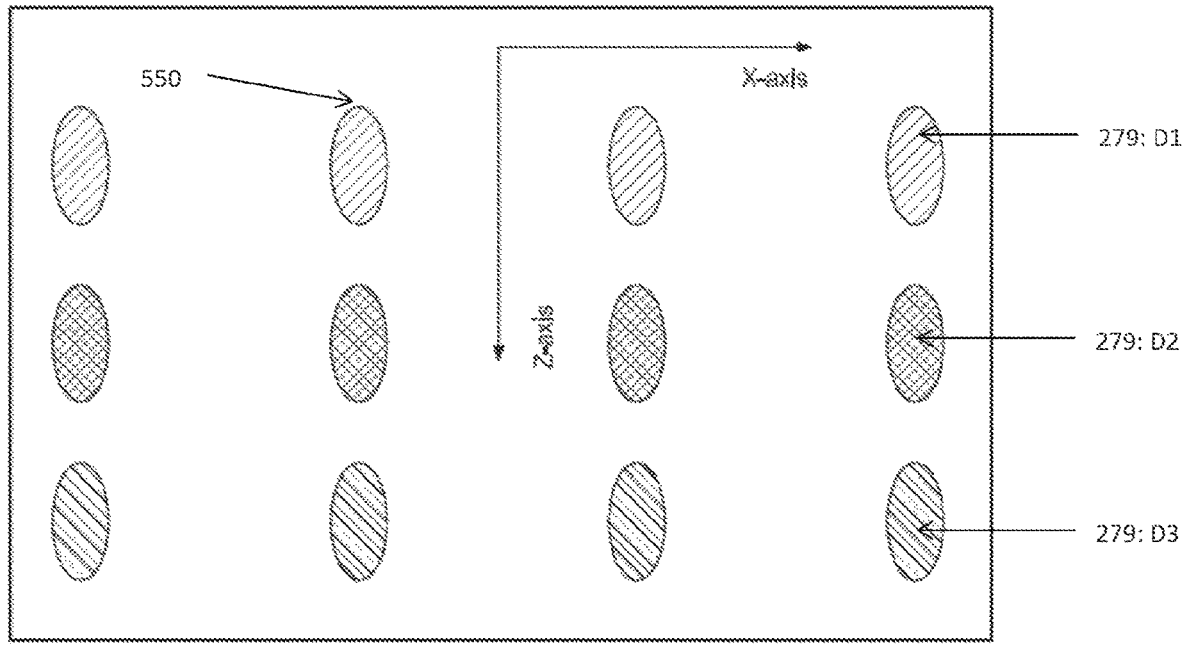
FIG. 19 is a schematic view from a x-z plane of the multiple thermal coagulation zones at various depths produced by a transducer according to FIG. 18.
Figure 20:
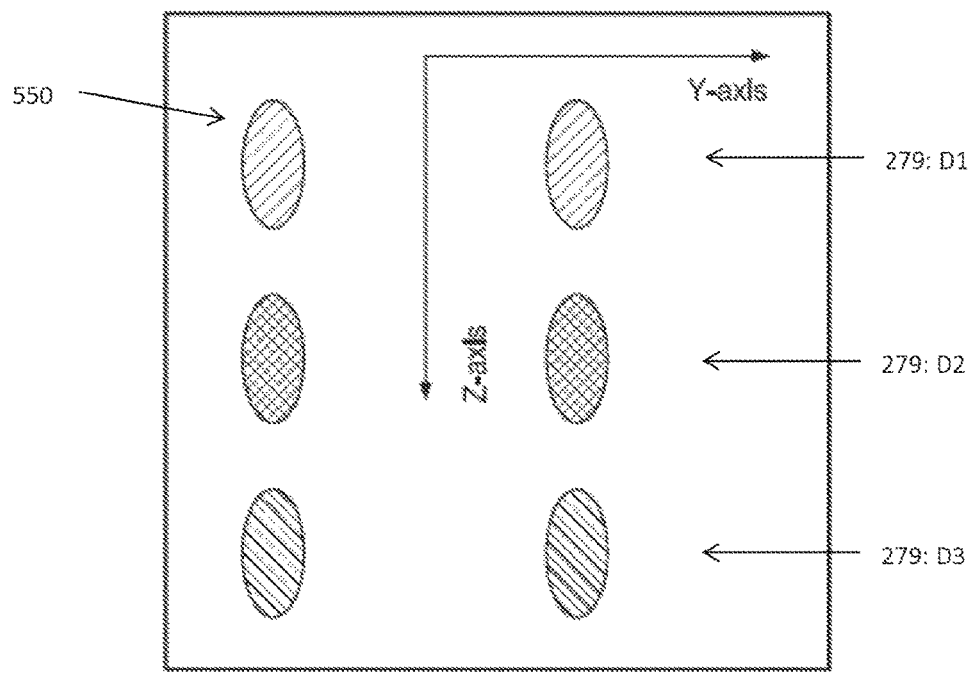
FIG. 20 is a schematic view from a y-z plane of the multiple thermal coagulation zones at various depths produced by a transducer according to FIG. 18.

In one embodiment, a transducer 280 comprising an annular convex side 282 and a striped concave side 283 is configured to produce multiple depth thermal coagulation zones 550 at various depths 279, as shown in FIGS. 18 (projection in x-y-z space), 19 (x-z plane) and 20 (y-z plane). FIG. 18 shows a three dimensional sketch of the micro-coagulation points. In one embodiment, two, three, four, or more points may be generated simultaneously. In one embodiment, two points are generated simultaneously. In one embodiment, it is expected the deeper micro-coagulation points would be created first (e.g., 4.5 mm) before moving to the next depth (e.g., 3.0 mm) and then finally to the shallowest depth (e.g., 1.5 mm). In one embodiment, the motion mechanism moves left-to-right and right-to-left. In one embodiment, a temperature of the skin may be limited by forming the micro-coagulation points at the deepest depth (e.g., 4.5 mm) when moving left-to-right and then placing the next depth (e.g., 3.0 mm) when moving right-to-left and then completing the treatment at with the micro-coagulation points at the shallowest depth (e.g., 1.5 mm) when moving left-to-right again. FIG. 19 shows a projection of the treatment along the direction of mechanical motion (x-axis) and depth (z-axis). FIG. 20 shows a projection of the treatment along the direction where the beam is split (y-axis) and depth (z-axis).

Figure 21:
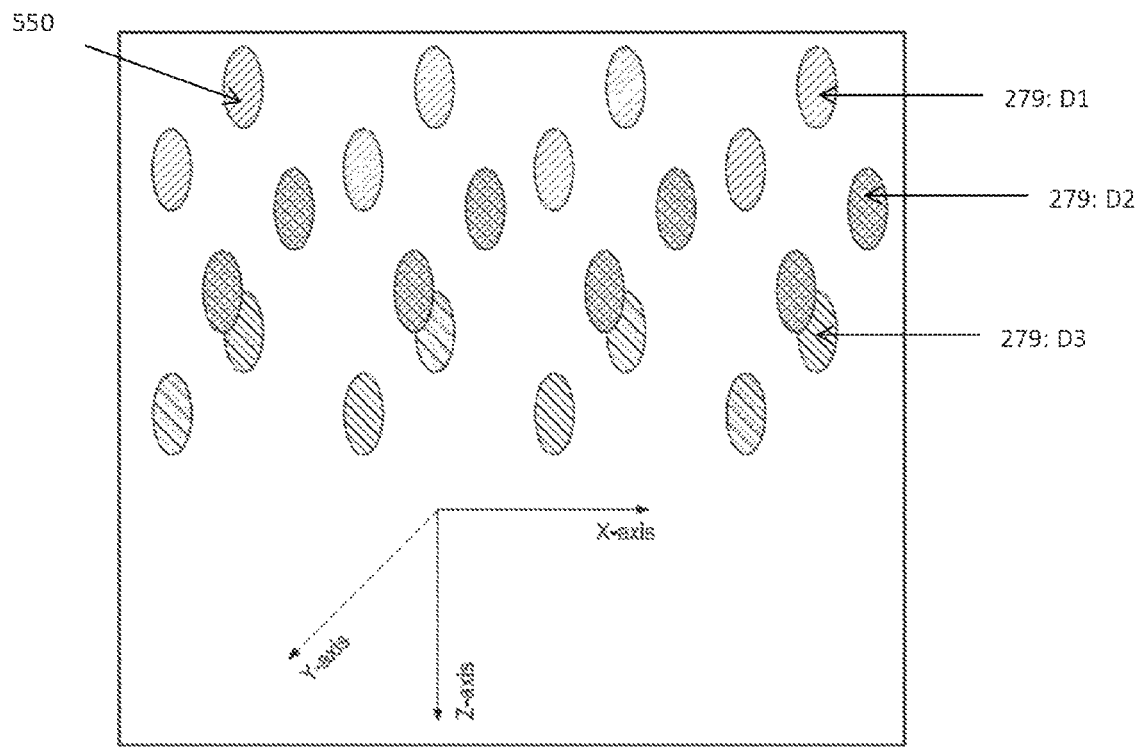
FIG. 21 is a schematic view of multiple thermal coagulation zones at various depths produced by a transducer according to various embodiments of the present invention.
Figure 22:
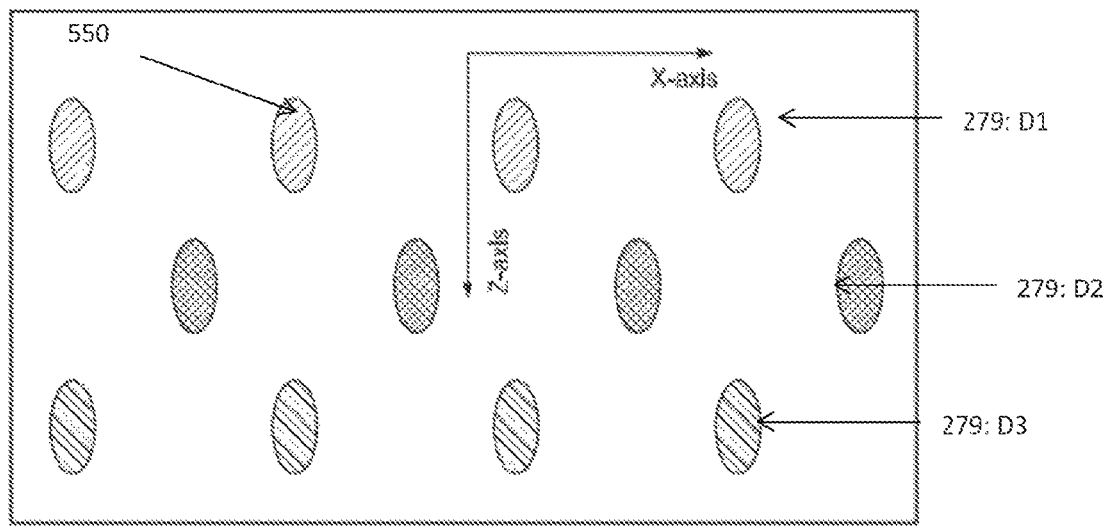
FIG. 22 is a schematic view from a x-z plane of the multiple thermal coagulation zones at various depths produced by a transducer according to FIG. 21.
Figure 23:
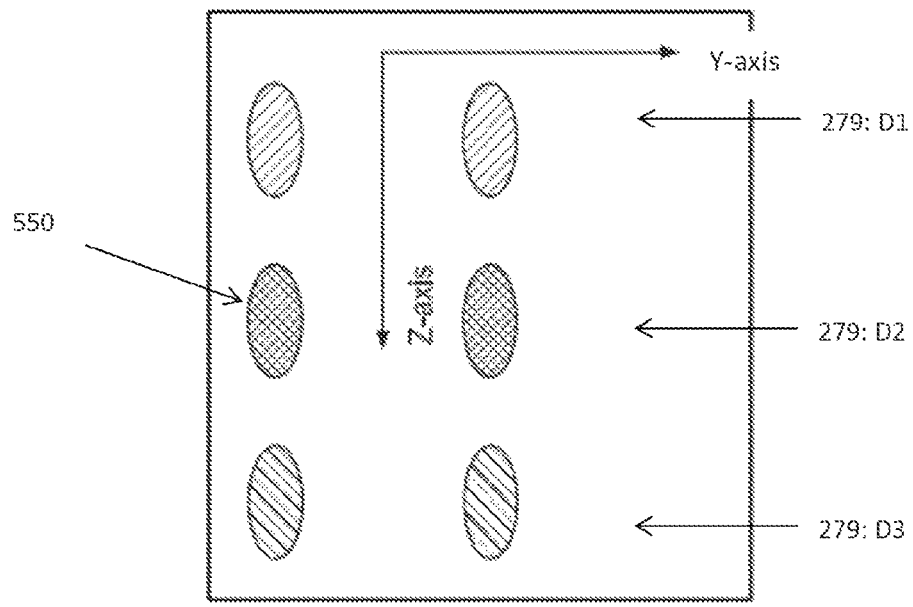
FIG. 23 is a schematic view from a y-z plane of the multiple thermal coagulation zones at various depths produced by a transducer according to FIG. 21.

FIGS. 21-23 illustrate an embodiment of a simultaneous multiple depth treatment device configured to create TCP's at depths of 1.5 mm, 3.0 mm, and 4.5 mm, wherein the middle layer is offset from the deep and shallow depths. In one embodiment, a transducer 280 comprising an annular convex side 282 and a striped concave side 283 is configured to produce multiple depth thermal coagulation zones 550 at various depths 279, as shown in FIGS. 21 (projection in x-y-z space), 22 (x-z plane) and 23 (y-z plane). In one embodiment, the length of the TCP may limit the ability to stack multiple depth TCP's directly on top of each other. In one embodiment, the motion mechanism offsets the different depth TCPs treatments from each other. FIG. 21 shows the three dimensional drawing of the offset multiple depth transducers. A similar process of delivery which was described for FIGS. 18-20 may be applied in with the embodiment in FIGS. 21-23, wherein the micro-coagulation points may be delivered when moving left-to-right or right-to-left to minimize the possibility any potential injury to the epidermis or dermis or tissue layers. FIG. 22 shows a projection of the delivery along the mechanical motion (x-axis) and depth (z-axis). This clearly shows the middle layer of TCP's offset from the deep and shallow treatments. FIG. 23 shows a projection of the delivery along the direction where the beam is split (y-axis) and depth (z-axis).

Figure 24:
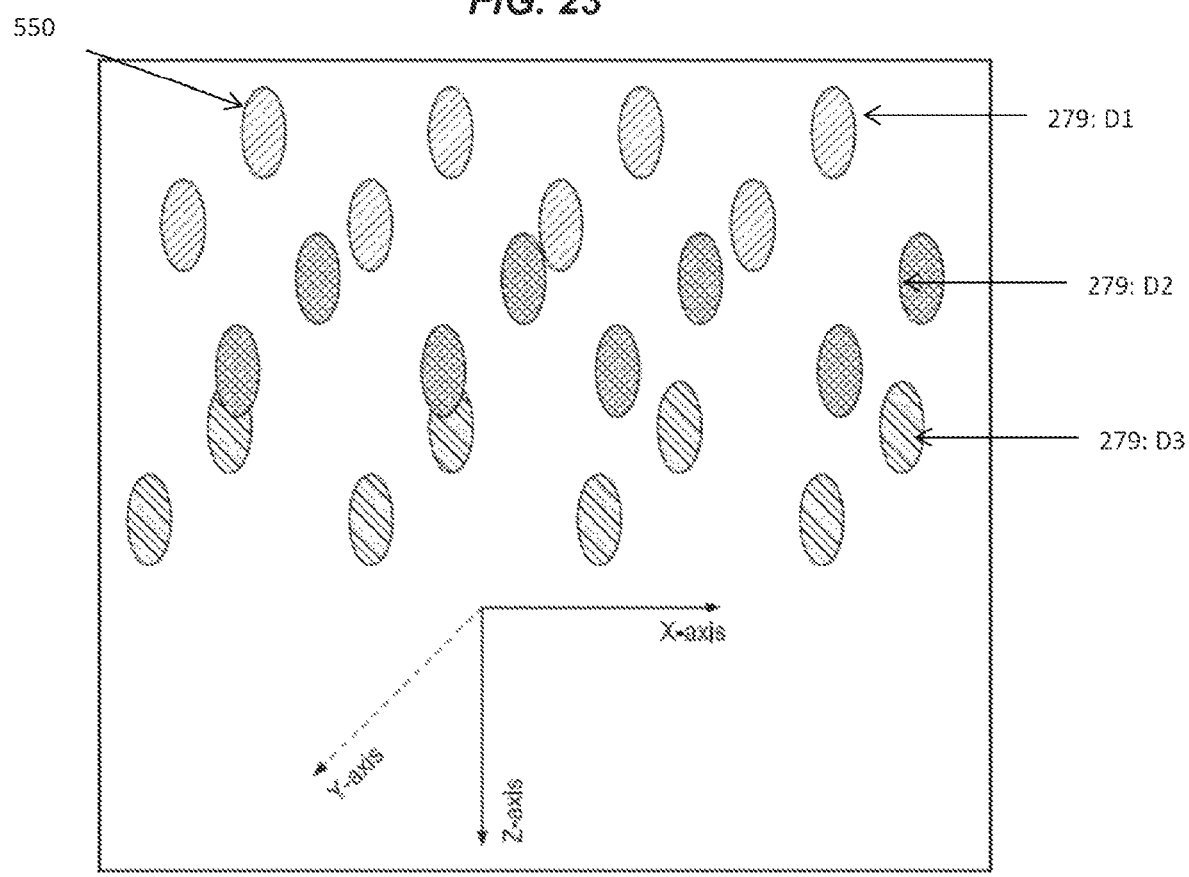
FIG. 24 is a schematic view of multiple thermal coagulation zones at various depths produced by a transducer according to various embodiments of the present invention.
Figure 25:
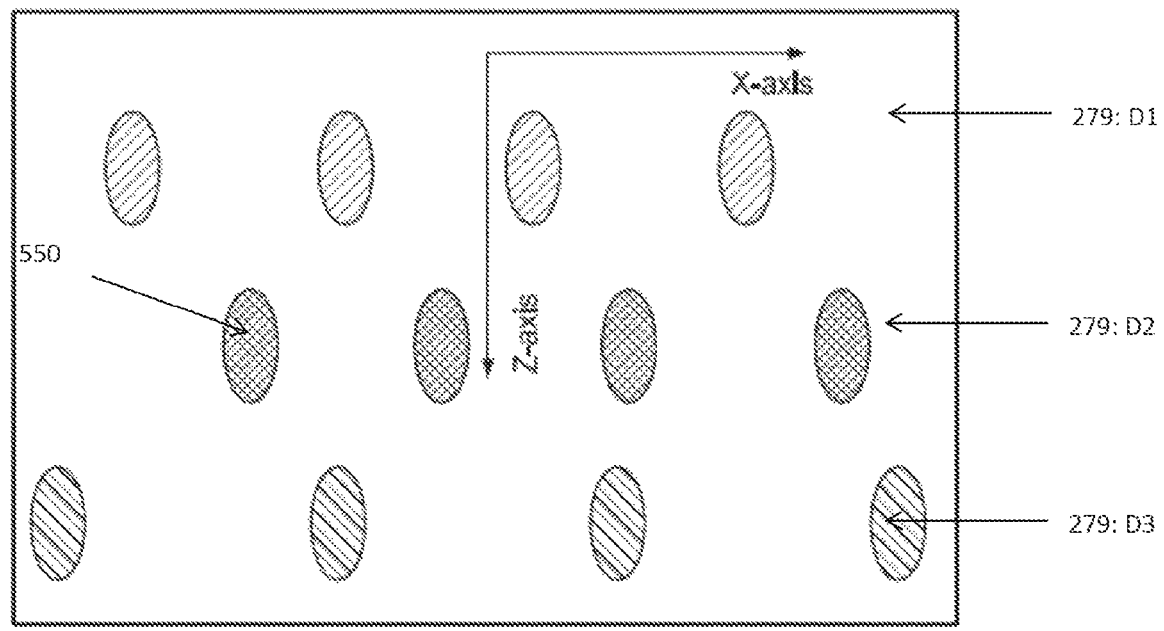
FIG. 25 is a schematic view from a x-z plane of the multiple thermal coagulation zones at various depths produced by a transducer according to FIG. 24.
Figure 26:
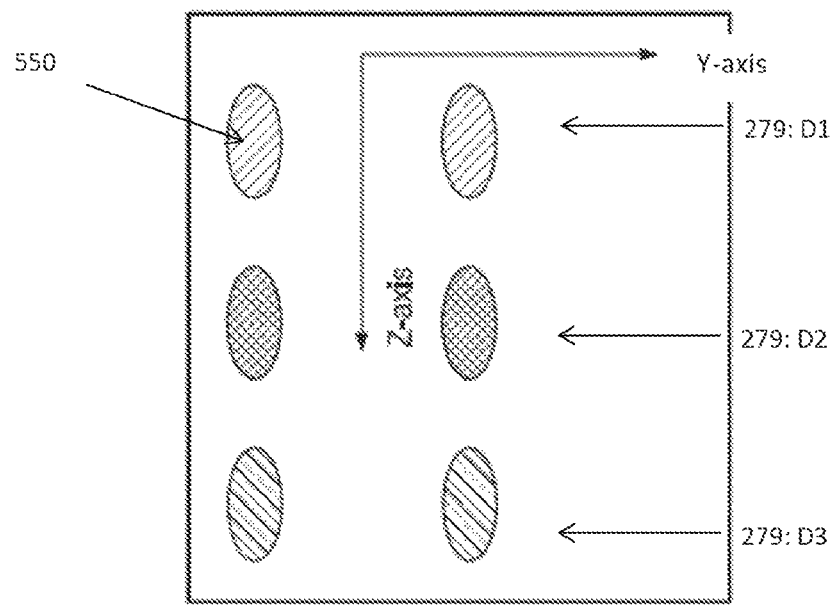
FIG. 26 is a schematic view from a y-z plane of the multiple thermal coagulation zones at various depths produced by a transducer according to FIG. 24.

FIGS. 24-26 illustrate an embodiment of a simultaneous multiple depth treatment device configured to create TCP's at depths of 1.5 mm, 3.0 mm, and 4.5 mm, wherein the middle layer is offset from the shallow depth with varying pitches. In one embodiment, a motion mechanism can be used to match the separation distance between the TCPs in the single line treatments. FIGS. 24-26 show a three dimensional sketch of the multi-depth simultaneous treatment. In this case in an embodiment, the 4.5 mm depth treatment is delivered at one pitch (1.5 mm apart) whereas the 3.0 mm depth and 1.5 mm depth treatments are delivered at another pitch (e.g. 1.1 mm apart). Although the 1.5 mm depth and 3.0 mm depth treatments are at the same pitch (e.g. 1.1 mm), the motion mechanism allows an offset to be applied to prevent stacking of the micro-coagulation points. FIG. 25 shows a projection of the delivery along the mechanical motion (x-axis) and depth (z-axis). This clearly shows the middle layer of TCP's offset from the shallow treatment even though the pitch is the same. Similarly, the deepest treatment is at a slightly larger pitch relative to the two other depths. FIG. 26 shows a projection of the delivery along the direction where the beam is split (y-axis) and depth (z-axis).

In various embodiments, a transducer 280 comprising an annular convex side 282 and a striped concave side 283 (such as shown in FIG. 16 and/or FIG. 17), produces a treatment pattern shown in embodiments of FIGS. 25, 26, and/or 29. In an embodiment, transducer 280 with an annular convex side 282 and a striped concave side 283 produces an intensity peaks near the center of the focal zone when viewed in an projection in x-y-z space (such as in FIGS. 18 and 19) where control of each ring in the annular convex side 282 has an amplitude (A) and a phase (θ). In this case, poling based on the stripes creates simultaneous foci at one depth. In order to create the simultaneous foci at each depth as shown in FIGS. 18 and 19, different phases (θ) and different amplitudes (A) are applied to each ring in order to produce the simultaneous foci at the different depths. The different phases enable the two foci to move to different focal depths and the different amplitudes allow the focal intensity to vary and thus the heating rate in tissue. The amount of separation between the two foci at the same depth along the Y axis is determined by the frequency, focal depth, and spatial frequency of the stripes (See equation 14 where it is solved for s). The transducer may be manually or mechanically moved to precisely space the simultaneous foci along the X axis. In one embodiment, a middle ring has an amplitude $A_1$ greater than the next outer ring with an amplitude $A_2$, which is greater than $A_3$, ... until the outer most ring amplitude $A_n$, creating a wider intensity range and the ability to shape to two foci that appear simultaneously. This control of the amplitude allows the width of the beam at the two foci to vary as well as the intensity which affects the heating rate.

In various embodiments, a continuous wave function may be used to produce simultaneous focal zones at different depths below a skin surface combining excitation functions for focal solution with another solution. In one embodiment, a focal zone ($f_1$) at a first depth ($d_1$) is simultaneously produced with a second focal zone ($f_2$) at a second depth ($d_2$) that is different than the first depth ($d_1$). Both foci at different depths ($d_1$ and $d_2$) may be produced simultaneously via linear systems combine excitation to a single ultrasound transduction element. The table below show two sets of amplitudes and phases required for each focal zone and depth. Since these two excitations are occurring at the same frequency, it is possible to combine the two excitations on each ring to one amplitude and one phase. Suppose the excitation on ring number 1 for focus #1 is written as:

$$x_{1,1}(t)=A_{1,1}\sin(\omega t+\theta_{1,1})$$

Suppose the excitation on ring number 1 for focus #2 is written as:

$$x_{1,2}(t)=A_{1,2}\sin(\omega t+\theta_{1,2})$$

where ω is 2πf where f is the frequency and t is time.

| RING NUMBER | FOCUS #1 ($f_1$) at a depth ($d_1$) | | FOCUS #2 ($f_2$) at a depth ($d_2$) | |
|---|---|---|---|---|
| | Amplitude | Phase | Amplitude | Phase |
| 1 | $A_{1,1}$ | $\theta_{1,1}$ | $A_{1,2}$ | $\theta_{1,2}$ |
| 2 | $A_{2,1}$ | $\theta_{2,1}$ | $A_{2,2}$ | $\theta_{2,2}$ |
| 3 | $A_{3,1}$ | $\theta_{3,1}$ | $A_{3,2}$ | $\theta_{3,2}$ |
| 4 | $A_{4,1}$ | $\theta_{4,1}$ | $A_{4,2}$ | $\theta_{4,2}$ |
| 5 | $A_{5,1}$ | $\theta_{5,1}$ | $A_{5,2}$ | $\theta_{5,2}$ |
| 6 | $A_{6,1}$ | $\theta_{6,1}$ | $A_{6,2}$ | $\theta_{6,2}$ |
| 7 | $A_{7,1}$ | $\theta_{7,1}$ | $A_{7,2}$ | $\theta_{7,2}$ |
| 8 | $A_{8,1}$ | $\theta_{8,1}$ | $A_{8,2}$ | $\theta_{8,2}$ |

In order to produce two foci simultaneously at two different depths, then the two excitations to the first ring must be combined:

$$X_1(t)=x_{1,1}(t)+x_{1,2}(t)=A_{1,1}\sin(\omega t+\theta_{1,1})+A_{1,2}\sin(\omega t+\theta_{1,2})$$

However, even though this is the necessary excitation on ring 1, it is unclear the actual amplitude and phase that is required on the ring to properly excite for both $f_1$ and $f_2$ at the same time. In order to determine this new Amplitude ($\Lambda_1$) and new phase ($\Omega_1$) for the combined effect, the following trigonometric identity is applied:

$$\Lambda_1 = \text{sqrt}([A_{1,1}\cos(\theta_{1,1})+A_{1,2}\cos(\theta_{1,2})]^2 + [A_{1,1}\sin(\theta_{1,1})+A_{1,2}\sin(\theta_{1,2})]^2)$$

$$\Omega_1 = \tan^{-1}[(A_{1,1}\sin(\theta_{1,1})+A_{1,2}\sin(\theta_{1,2}))/(A_{1,1}\cos(\theta_{1,1})+A_{1,2}\cos(\theta_{1,2}))]$$

such that the new excitation on ring 1 is:

$$X_1(t)=\Lambda_1\sin(\omega t+\Omega_1)$$

This same process can be applied to the other rings to obtain the array solution to create $f_1$ and $f_2$ simultaneously. Similarly, if the desire is to deliver three or more foci simultaneously, then the process can be repeated using the above identity until only one excitation and one phase is computed for each ring. For example, suppose that the goal was to create three foci simultaneously, then the initial new amplitudes and new phases for each ring are computed based on the amplitudes and phases required for focus 1 and focus 2. Next, these new amplitudes and phases are combined with the ring excitations necessary for focus 3.

Although it is possible to create simultaneous foci using this methodology, the necessary amplitudes may be limited by saturation of the piezoelectric material as well as the ability of the tissue to absorb the increased intensities in the surrounding tissue when generating multiple foci. These physical limitations must be compared against the time advantages of generating the foci simultaneously.

Figure 27:
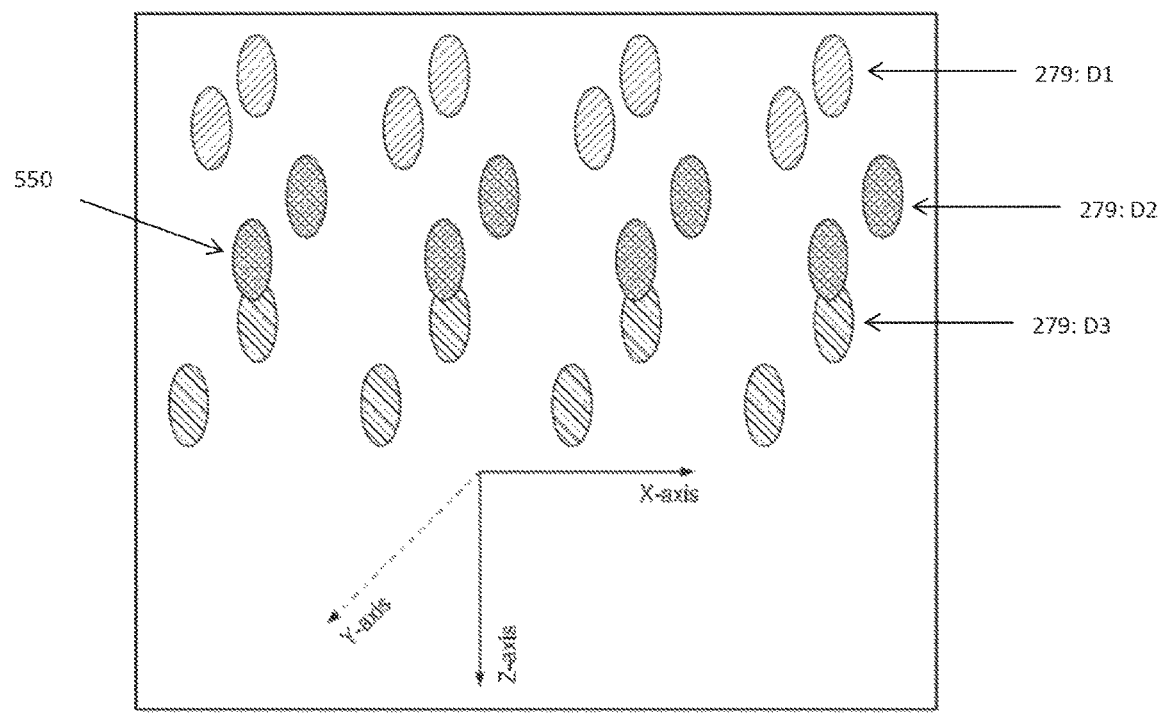
FIG. 27 is a schematic view of multiple thermal coagulation zones at various depths produced by a transducer according to various embodiments of the present invention.
Figure 28:
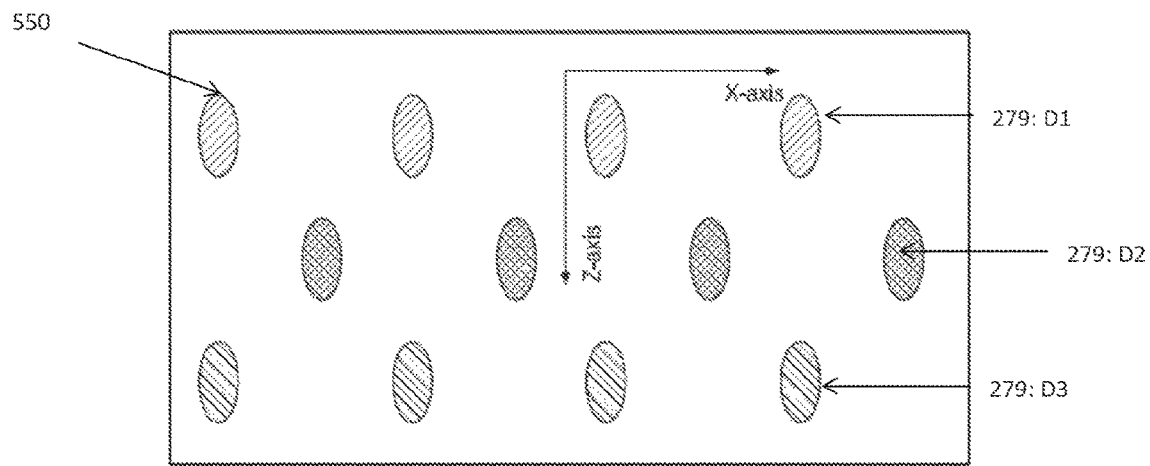
FIG. 28 is a schematic view from a x-z plane of the multiple thermal coagulation zones at various depths produced by a transducer according to FIG. 27.
Figure 29:
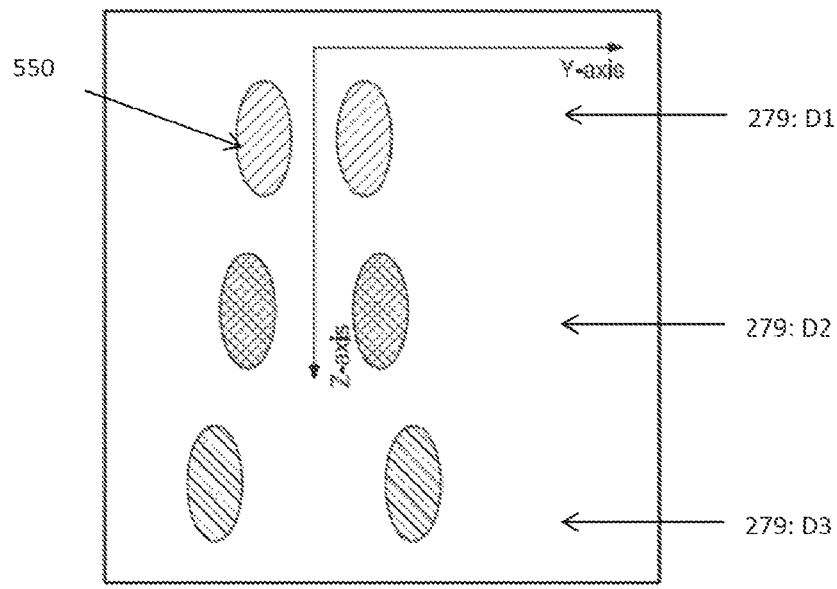
FIG. 29 is a schematic view from a y-z plane of the multiple thermal coagulation zones at various depths produced by a transducer according to FIG. 27.

FIGS. 27-29 illustrate an embodiment of a simultaneous multiple depth treatment device configured to create TCP's at depths of 1.5 mm, 3.0 mm, and 4.5 mm, wherein the middle layer is offset from the shallow depth and frequency is used to create different separation distances at each depth. In FIGS. 24-26, the middle depth of TCPs are offset from the deepest and shallowest depth using the motion mechanism. In various embodiments, the amount of separation between the simultaneously created TCPs is dependent on the treatment frequency. In one embodiment, the device is able to deliver therapy at multiple frequencies (e.g., with a broad bandwidth therapy transducer), and it is possible to modulate the distance between the TCPs using frequency. As discussed with FIG. 18, the spacing of the stripes are determined upon manufacture since this is created through ceramic poling. Lower frequencies and a deeper depth create a wider separation between the simultaneously created TCPs (y-z plane). FIG. 4a shows the three dimensional matrix of TCPs with this varying degree of separation. As the frequency is increased for the shallower depths and the depth of treatment is reduced, the distance between the simultaneously created TCPs decreases. FIG. 28 shows a projection of the delivery along the mechanical motion (x-axis) and depth (z-axis). This clearly shows the middle layer of TCP's offset from the shallow and deep treatments even though the pitch is the same. FIG. 29 shows a projection of the delivery along the direction where the beam is split (y-axis) and depth (z-axis). This projection shows the spacing between the TCPs gets progressively larger as the depth of treatment increases which is primarily due to depth and frequency changes in treatment.

In one embodiment, as shown in FIG. 29, different spacing can be produced by changing frequencies and focal depth. For example, equation 14 is:

$$s = (2k_x z_f \lambda)/(2\pi)$$

Where s is the spacing between the two simultaneous foci at the same depth. The equation shows that the foci separation is a function of focal depth ($z_f$) and frequency (since $\lambda$ is speed of sound divided by frequency). Suppose the same frequency and spatial frequency on the stripe is used. The table summarizes the separation for the different foci which are separated by 1.5 mm.

| zf (mm) | frequency (MHz) | wavelength (mm) | kx (mm^ − 1) | s (mm) |
|---|---|---|---|---|
| 15.5 | 7 | 0.22 | 1.5 | 1.628 |
| 17 | 7 | 0.22 | 1.5 | 1.786 |
| 18.5 | 7 | 0.22 | 1.5 | 1.943 |

However, if the frequency varies such that the higher frequency is used for the shallowest focus, then a much broader range of separation distances is achievable:

| zf (mm) | frequency (MHz) | wavelength (mm) | kx (mm^ − 1) | s (mm) |
|---|---|---|---|---|
| 15.5 | 10 | 0.154 | 1.5 | 1.140 |
| 17 | 7 | 0.22 | 1.5 | 1.786 |
| 18.5 | 4 | 0.385 | 1.5 | 3.401 |

In various embodiments, different w (e.g., w1, w2) may be used to vary the distance or spacing. In various embodiments, a continuous wave function may be used to produce simultaneous focal zones at different depths below a skin surface combining frequencies with Fourier transforms. In one embodiment, a focal zone ($f_1$) at a first depth ($d_1$) is simultaneously produced with a second focal zone ($f_2$) at a second depth ($d_2$) that is different than the first depth ($d_1$). Both foci at different depths ($d_1$ and $d_2$) may be produced simultaneously via linear systems combine excitation to a single ultrasound transduction element.

| $f_1$ | $f_2$ |
|---|---|
| $A_{1,1}/\theta_{1,1}$ | $A_{1,2}/\theta_{1,2}$ |
| $A_{2,1}/\theta_{2,1}$ | $A_{2,2}/\theta_{2,2}$ |
| $A_{3,1}/\theta_{3,1}$ | $A_{3,2}/\theta_{3,2}$ |
| $A_{4,1}/\theta_{4,1}$ | $A_{4,2}/\theta_{4,2}$ | where $X_1$=excitation (A, $\theta$)=$A_{1,1}$ sin ($w_1 t - \theta_{1,1}$) $A_{1,2}$ sin ($w_2 t - \theta_{1,2}$) to produce two simultaneous foci at a varying distances.

Figure 30:
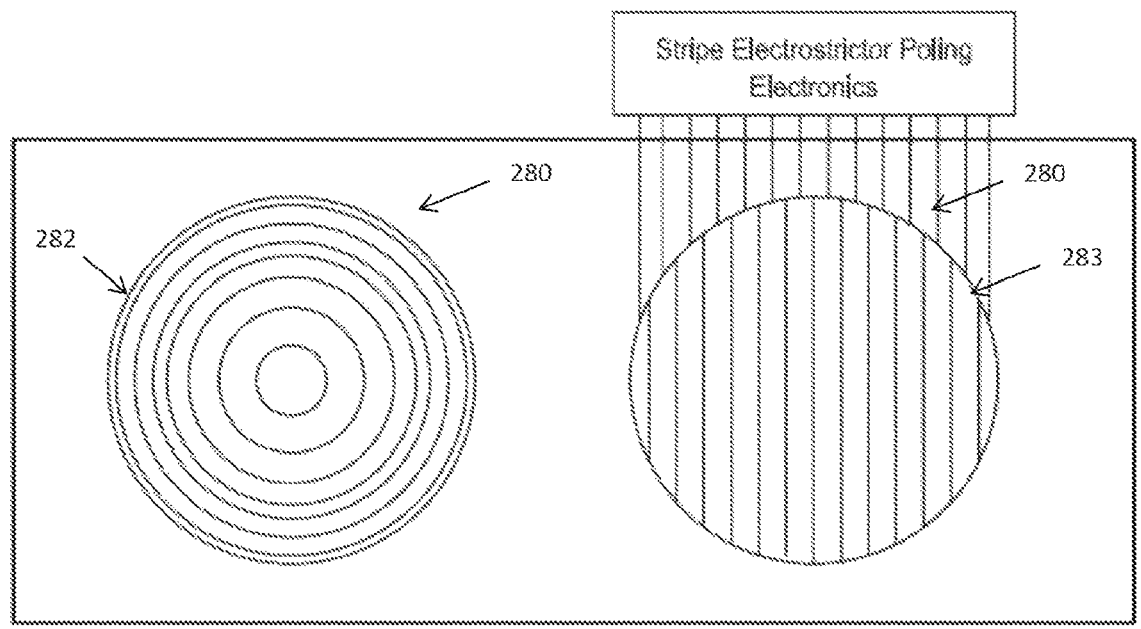
FIG. 30 is a schematic view of a transducer as viewed from a convex side and a concave side according to various embodiments of the present invention.
Figure 31:
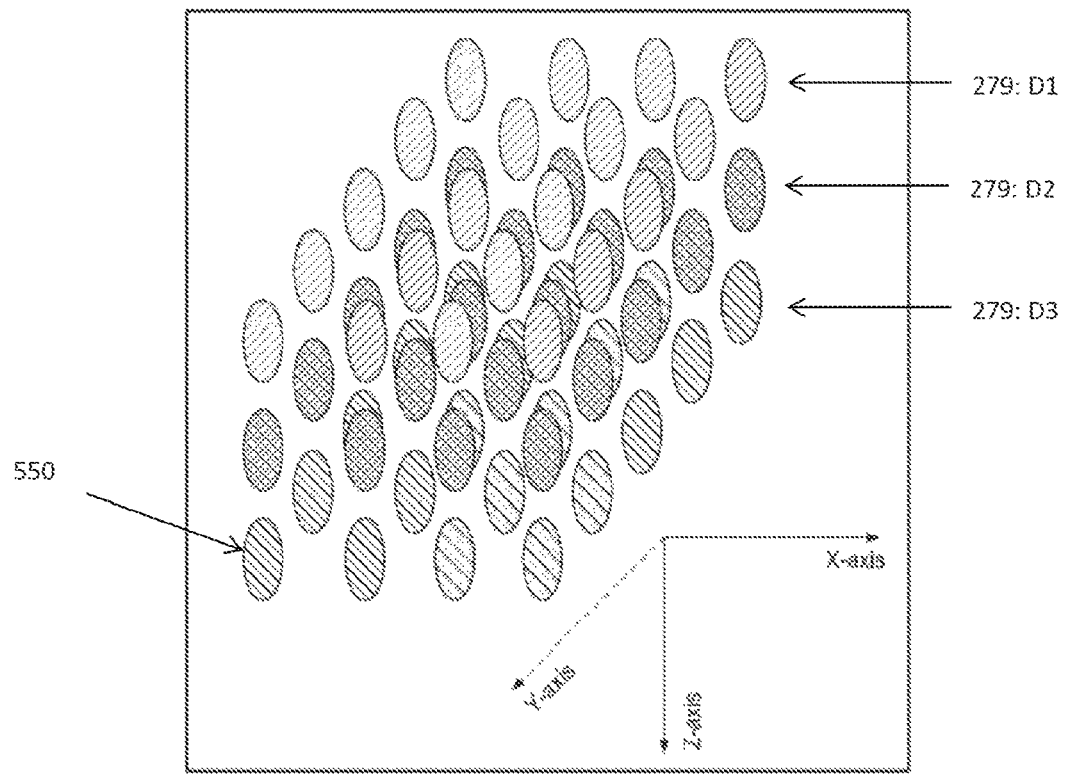
FIG. 31 is a schematic view of multiple thermal coagulation zones at various depths produced by a transducer according to various embodiments of the present invention.
Figure 32:
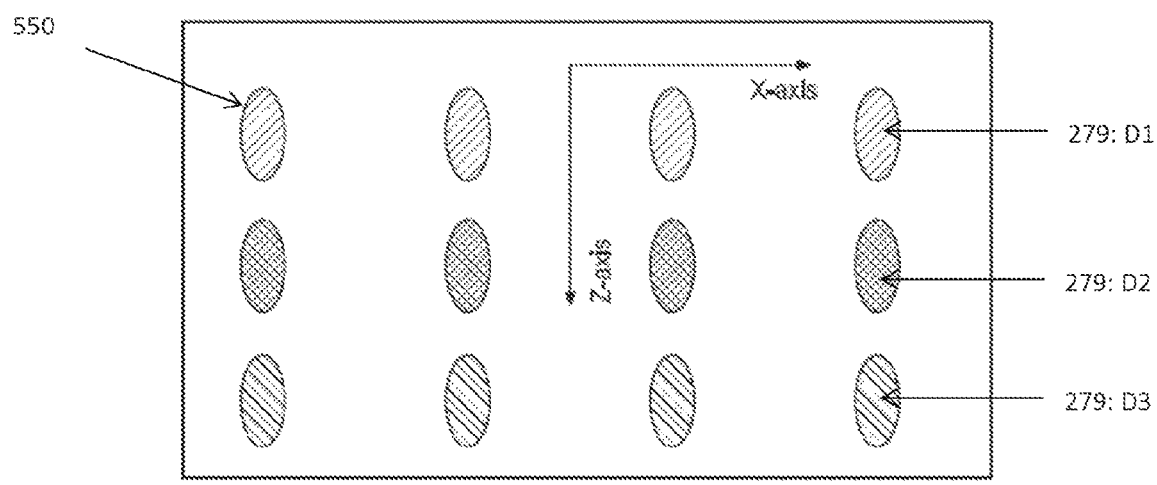
FIG. 32 is a schematic view from a x-z plane of the multiple thermal coagulation zones at various depths produced by a transducer according to FIG. 31.
Figure 33:
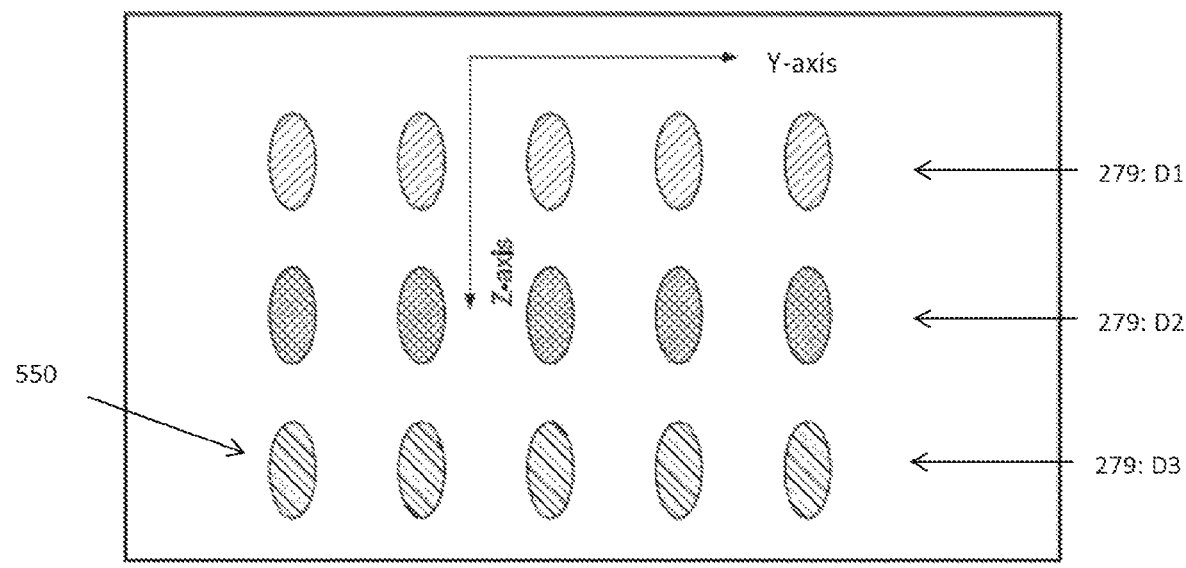
FIG. 33 is a schematic view from a y-z plane of the multiple thermal coagulation zones at various depths produced by a transducer according to FIG. 31.
Figure 37:
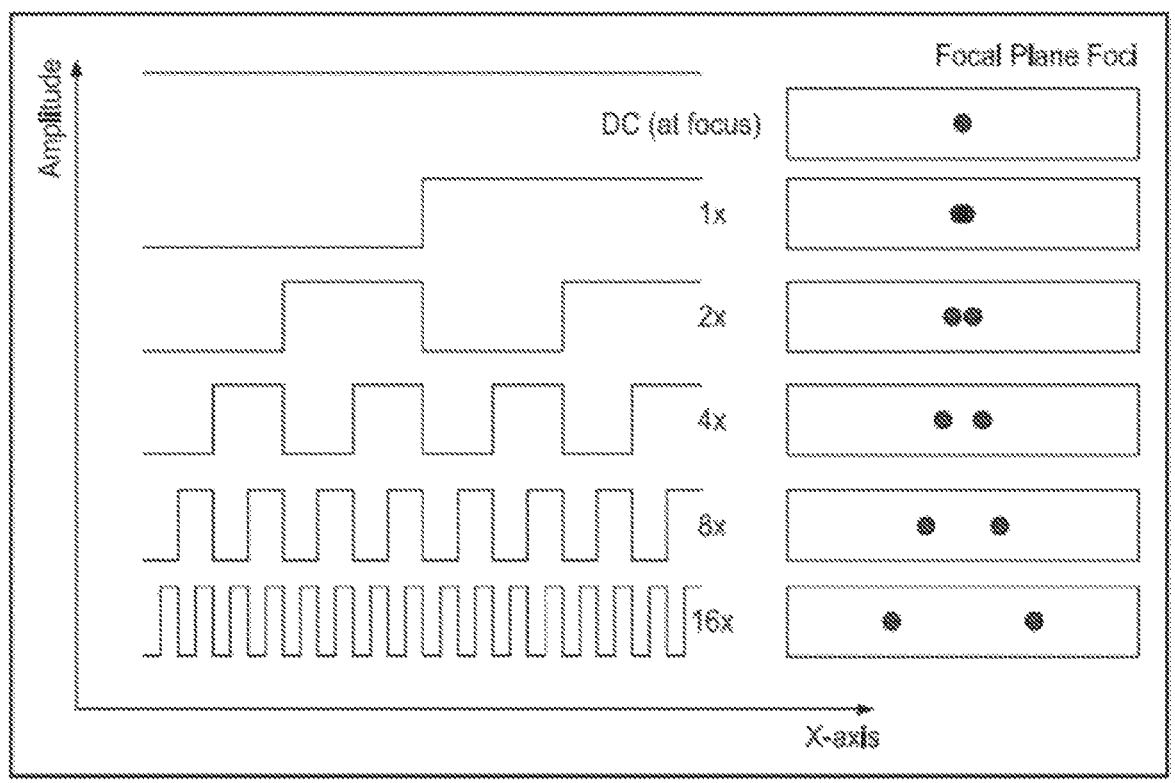
FIG. 37 is plot illustrating amplitude and direct current corresponding to focal plane foci produced by a transducer according to various embodiments of the present invention.

In various embodiments, electrostrictors exhibit piezoelectric behavior when a sufficient DC bias is placed upon the material. In one embodiment, the strength of the piezoelectric behavior is proportional to the acoustic sensitivity. In one embodiment, the electrostrictor material is used with the therapy bowl in the manufacturing process. In one embodiment, patterning and electrode attachment is achieved during manufacturing, but the poling of the electrostrictor is accomplished during the therapy delivery. For example, in one embodiment, the transmit aperture may be a square wave as shown in FIG. 37 or shaded through modification of the high voltage value. FIG. 30 illustrates an embodiment of a simultaneous multiple depth treatment device configured to create TCP's at depths of 1.5 mm, 3.0 mm, and 4.5 mm, wherein an annular array is coupled with an electrostrictor that enables multiple pairs to be generated simultaneously at different depths. In one embodiment, an electrostrictor changes the spatial frequency (such as shown in one embodiment in FIG. 37) providing for creating a line of treatment (such as shown in one embodiment in FIG. 34). In one embodiment, the electrostrictor produces a line of treatment without employing a mechanical motion mechanism. In one embodiment, a the electrostrictor produces lines perpendicular to the motion of a mechanical motion mechanism. Thus, in various embodiments, a multidimensional treatment can create one, two, or more treatment focal zones in various spacing, lines, planes, or three dimensional spaces. In some embodiments, and electrostrictor results in the displacement of ions in the crystal lattice of the piezoelectric transducer upon being exposed to an external electric field. In various embodiments, FIGS. 17-29 have a fixed poling pattern to yield a separation distance between the two simultaneously created TCPs. This is because the poling pattern is created in a piezoelectric ceramic during fabrication. The spacing between the stripes determines the spacing between the TCPs. The larger the distance between the stripes, the closer the TCPs are. In some embodiments, there is no ability after the poling is completed to change the distance between the stripes. In one embodiment, as shown in FIGS. 30-33, an electrostrictor material does not involve poling, but instead uses an electrostrictor to apply a direct current (DC) voltage during device operation to exhibit piezoelectric behavior which can be used to improve device performance. FIG. 30 shows the front and back (e.g., concave and convex sides) of the ceramic bowl which is similar to the embodiment shown in FIG. 17. In one embodiment, an annular pattern is on the back (e.g., convex side) of the transducer. The front side (patient side, e.g., concave side) is slightly different when compared to the embodiment in FIG. 17, e.g., the stripes appear to be created at a finer pitch. Second, the ceramic is not poled, but connections from each individual stripe are connected to a separate bank of electronics to place a voltage across the stripe to create the appropriate pattern that yields a separation distance between the TCPs. In one embodiment, the voltage varies at a high spatial frequency, resulting in a larger separation distance is created between the TCPs. The electronics allows this pattern to be varied such that the distance between the TCPs may also be varied. The result is a collection of simultaneous TCPs which can be created through this amplitude modulation. It is not necessary to place a negative or positive voltage on each stripe. In some embodiments, shorting the stripe to ground prevents or reduces acoustic excitation. FIG. 31 illustrates an embodiment of the type of TCP distribution that can be created three dimensionally. In an embodiment, five TCPs at each depth are created which is accomplished with three different DC amplitude modulation patterns on the stripes. Again, the order may be varied within a depth 279 or at each depth based on the movement of the motion mechanism either left to right or right to left, modulation pattern, and focusing of the rings. The order used is based on the safety tolerance of the epidermis and dermis and any other tissue layer, along with the goal to deliver the TCP as quickly as possible. FIG. 32 illustrates a projection of the delivery along the mechanical motion (x-axis) and depth (z-axis). FIG. 33 shows a projection of the delivery along the direction where the beam is split (y-axis) and depth (z-axis). This projection shows the five TCPs created in this plane. Two pairs of TCPs are created simultaneously where one is created at one time similar to the conventional transducers. In various embodiments, the techniques discussed with the embodiments of FIGS. 21-29 are applicable for the electrostrictor design.

Figure 34:
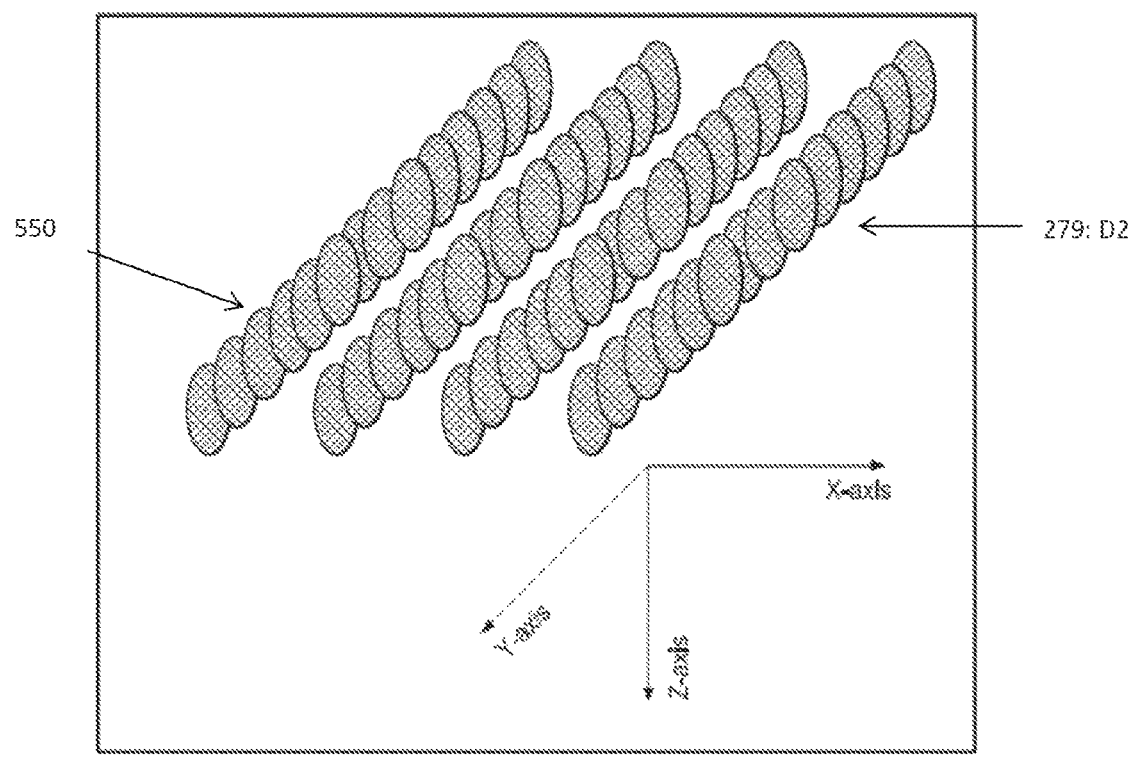
FIG. 34 is a schematic view of multiple thermal coagulation zones at various depths produced by a transducer according to various embodiments of the present invention.
Figure 35:
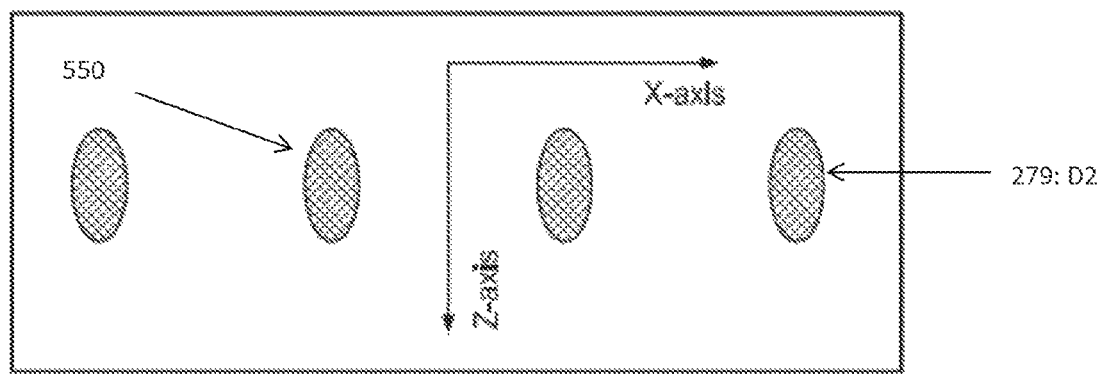
FIG. 35 is a schematic view from a x-z plane of the multiple thermal coagulation zones at various depths produced by a transducer according to FIG. 34.
Figure 36:
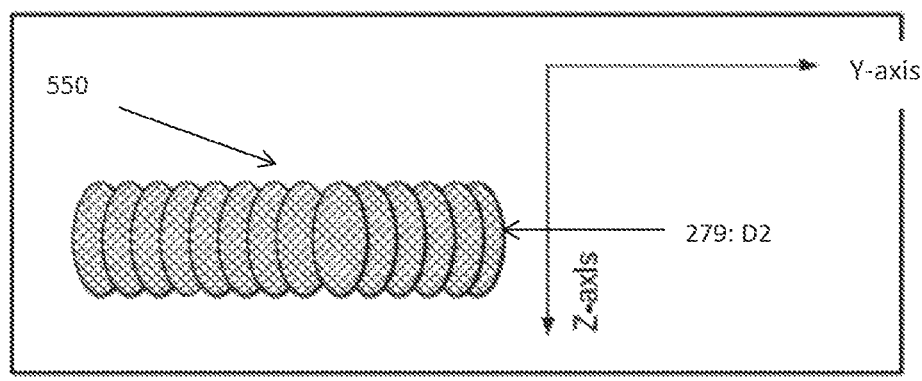
FIG. 36 is a schematic view from a y-z plane of the multiple thermal coagulation zones at various depths produced by a transducer according to FIG. 34.

FIGS. 34-36 illustrate an embodiment of a simultaneous multiple depth treatment device configured to create TCP's at depths of 1.5 mm, 3.0 mm, and 4.5 mm, with an annular array coupled with a simultaneous treatment transducer enables two lines to be generated simultaneously at different depths. In one embodiment, an advantage of using a electrostrictor with enough stripes is the ability to create a thermal line of therapy if the pattern is rapidly changed. FIG. 34 illustrates an embodiment showing a line of TCPs in three dimensions created using multiple spatial frequencies for the electrostrictor pattern at only one depth. Depending on the rate of pattern change across the stripes, this heating can be varied to create a line of micro-coagulation or a line of elevated temperature is tissue for cell apoptosis. FIG. 35 shows the projection to the x-z plane which accounts for five lines. FIG. 36 shows the projection to the y-z plane which shows that a line of heating along the y-axis at a specific depth.

In one embodiment, FIG. 37 shows different patterns that can be generated when the stripes are fine pitched. In FIG. 37, the X-axis represents the distance across a transducer. The Y-axis represents the amplitude of DC at the location across the transducer. Various DC signals applied across the transducer can result, in various embodiments, of different spacing between foci. In one embodiment, a fine pitch is related to the distance of the split that is trying to be achieved, operational frequency, focal depth. In various embodiments, a fine pitch is between 0.1 mm to 0.05 mm (e.g., 100 microns to 50 microns, including 90, 80, 70, 60 microns and any values therein). The figure shows the amplitude modulation that is possible along the y-axis to yield a different spacing for the micro-coagulation points. Although the figure covers factor of 2 multiples, it is possible to have other modulation patterns which are between the multiples shown. It is not necessary that the modulation patterns are whole numbers of the 1× pattern. In various embodiments, even, odd and null patterns are possible. Finally, the electrostrictor methodology also offers the possibility to modulate the amplitude pattern since the polarization is a strong function of the DC bias.

Determining Effectiveness of Ultrasound Therapy

In various embodiments, it is desirable to obtain feedback regarding the effectiveness of an ultrasound therapy in producing a desired clinical result. Depending on the individual morphological difference between individual patients, an amount of acoustic energy delivered to a volume of tissue in a first patient may produce a first clinical result that is different from a second clinical result produced when the same amount of acoustic energy is delivered to the same volume of tissue in a second patient. Thus, systems and methods that help in determining the effectiveness of the administered ultrasound therapy in different patients can, for example, advantageously increase the efficacy and/or consistency of the ultrasound therapy.

In various embodiments, a desired outcome of the administered ultrasound therapy includes improving the appearance of skin, such as by reducing skin laxity to achieve one or more of the following beneficial aesthetic and/or cosmetic improvement effects: a face lift, a brow lift, a chin lift, an eye treatment (e.g., malar bags, treat infraorbital laxity), a wrinkle reduction, fat reduction (e.g., treatment of adipose and/or cellulite), cellulite (which may be called gynoid lipodystrophy) treatment (e.g., dimple or non-dimple type female gynoid lipodystrophy), décolletage improvement (e.g., upper chest), a buttock lift (e.g., buttock tightening), skin tightening (for example, treating laxity to cause tightening on the face or body, such as the face, neck, chest, arms, thighs, abdomen, buttocks, etc.), a scar reduction (e.g., reduction of breast capsular fibrosis), a burn treatment, a tattoo removal, a vein removal, a vein reduction, a treatment on a sweat gland, a treatment of hyperhidrosis, a sun spot removal, an acne treatment, and/or a pimple reduction. Accordingly, in some implementations, the effectiveness of the administered ultrasound therapy can be determined by measuring the elasticity of the portion of the tissue being subjected to the ultrasound therapy. In various embodiments, the systems and methods discussed herein are configured to measure elasticity of the portion of the tissue that is being treated via ultrasound therapy. In various implementations, the elasticity of the portion of the tissue that is being treated via ultrasound therapy can be measured in real-time, while the treatment is being administered.

In various embodiments, systems and methods that measure the elasticity of the portion of the tissue that is being treated via ultrasound therapy using shearwave imaging, such as constructive shearwave imaging and/or destructive shearwave imaging. Without relying on any particular theory, acoustic energy administered to the tissue can cause displacement of one or more portions of the tissue that is being treated via ultrasound therapy. In several embodiments, a response of the tissue as the displacement propagates is a shearwave. Without subscribing to any particular theory, the shearwave propagates outward from the focal zone (e.g., focal point, focal line, focal region, etc.) where the acoustic beam emitted from the transducer is focused. The outwardly propagating shearwave can be reflected from various portions of the tissue. The reflected shearwave can interfere constructively or destructively with the outwardly propagating shearwave. In constructive shearwave imaging, the characteristics of the constructively interfering shearwave can be obtained to determine the elasticity of the tissue.

Several embodiments described herein are especially useful for aesthetic and other procedures where adjusting (manually or in an automated manner) treatment parameters in real time is beneficial. In embodiments where a single subject is treated in a single session, one or more parameters such as frequency, power, intensity, duration and location of the treatment points (therapy) is modified based on the elasticity of the tissue below the skin surface. When multiple lines of thermal coagulation points are created, the parameters can be varied between the points and/or between the lines on the face or body. As an example, if a subject has insufficient elasticity in a certain region, the duration of treatment can be extended (as compared to a skin region with more elasticity). In some embodiments, one or more of frequency, power, intensity, duration or other parameter is altered (increased or decreased) by 10-30%, 30%-50%, 50-100%, 2-3 fold, 3-5 fold, or more, and overlapping ranges therein, and in some embodiments, such alterations are correlated and/or based on elasticity.

Figure 38:
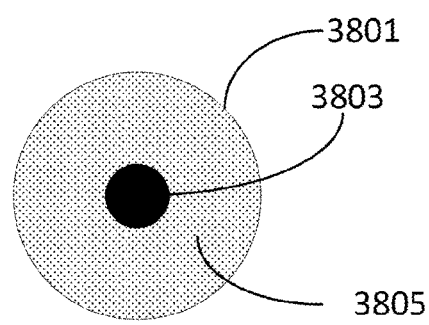
FIG. 38 schematically illustrates an example of a region that is analyzed using constructive shearwave imaging.

FIG. 38 schematically illustrates an embodiment of determining elasticity of a tissue within an excitation region using constructive shearwave imaging. In one embodiment illustrated in FIG. 38, the acoustic energy is administered over an excitation region 3801. The excitation region 3801 can correspond to the aperture of the acoustic beam emitted from an ultrasound transducer. In this illustrated embodiment, the excitation region 3801 is a circular area. The treatment source corresponds with the excitation region 3801 in some implementations. In some other implementations, the treatment source can be spaced apart from the excitation region 3801. The shearwave generated from a transducer for the acoustic excitation of the tissue converges to a central region 3803 of the excitation region 3801. Various characteristics of the converging shearwave including but not limited to arrival time, peak displacement, rise time and fall time can be obtained. From the obtained characteristics of the converging shearwave, the elasticity of the tissue within the excitation region 3801 can be determined to determine the effectiveness of the ultrasound therapy. The region 3805 within the excitation region 3801 can be referred to as the region of interrogation. Without any loss of generality, various characteristics of the converging shearwave can be obtained using a shearwave imaging system that is configured to image the central region 3803 of the excitation region 3801.

In various embodiments, the incident acoustic energy in the excitation region is focused at one or more treatment points (e.g., thermal coagulation points or "TCP"). In one embodiment, an ultrasound system 20 comprising a single focus transducer, the shearwave generated as a result of displacement of one or more portions of the tissue that is being treated via ultrasound therapy will propagate outwardly from the focal zone (or focal point) where the acoustic beam emitted from the transducer is focused. In such implementations with a single treatment point may not be practical to detect the constructive interference between the outwardly propagating shearwave and the portion of the shearwave reflected from various portions of the tissue. Accordingly, it may not be as effective to use shearwave imaging (e.g., constructive shearwave imaging) techniques to measure the elasticity of the tissue when ultrasound therapy is administered using a single focus transducer.

In various embodiments, an ultrasound system 20 includes a transducer that provides two or more (e.g., a plurality or multiple) focus zones and/or treatment points. For example, in various embodiments of the ultrasound system 20, the acoustic beam from a single ultrasound transducer and/or single ultrasound transduction element can provide two ultrasound treatment points corresponding to two focus zones. In such implementations, the shearwaves originating from the two focus zones can converge towards a region between the two focus zones. For example, the shearwaves originating from the two focus zones can converge towards a central region between the two focus zones. In various embodiments, the central region can correspond to a mid-point between the two focus zones. The shearwaves originating from the two focus zones can interfere constructively in the central region between the two focus zones. Various characteristics of the constructive interference between the shearwaves originating from the two focus zones can provide information regarding the elasticity of the tissue between the two treatment points. As discussed above, the various characteristics can include but are not limited to arrival time, peak displacement, rise time and fall time.

Figure 39:
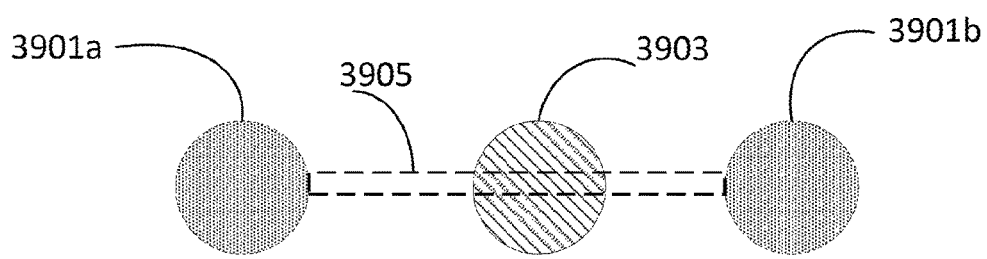
FIG. 39 schematically illustrates a method of interrogating the tissue in a region between two ultrasound excitation regions coinciding with corresponding treatment points using constructive shearwave imaging.

FIG. 39 schematically illustrates a method of interrogating the tissue in a region between two ultrasound excitation regions 3901a and 3901b using constructive shearwave imaging. The two ultrasound excitation regions 3901a and 3901b can be generated using a single ultrasound transducer as discussed herein. In the implementation illustrated in FIG. 39, the two treatment points coincide with the two excitation regions 3901a and 3901b. As discussed above, the shearwaves generated from the two excitation regions 3901a and 3901b converge to a central region 3903 between the two excitation regions 3901a and 3901b. Various characteristics including but not limited to arrival time, peak displacement, rise time and fall time of the converging shearwaves in the central region 3903 can be obtained using an imaging system to determine elasticity of the tissue in the interrogation region 3905.

It is noted from the FIG. 39 that the region of interrogation 3905 does not include the treatment points which coincide with the excitation region 3901a and 3901b. Generally, the elasticity of the tissue in the treatment points can also change. Accordingly, it is desirable for the interrogation region to include the treatment points as well. Accordingly, the ultrasound transducer may be driven at a lower frequency (e.g. using frequency modulation) to separate the regions of excitation from the treatment points so that the region of interrogation includes the treatment points as well. This concept is illustrated and discussed with reference to FIG. 40 below.

Figure 40:
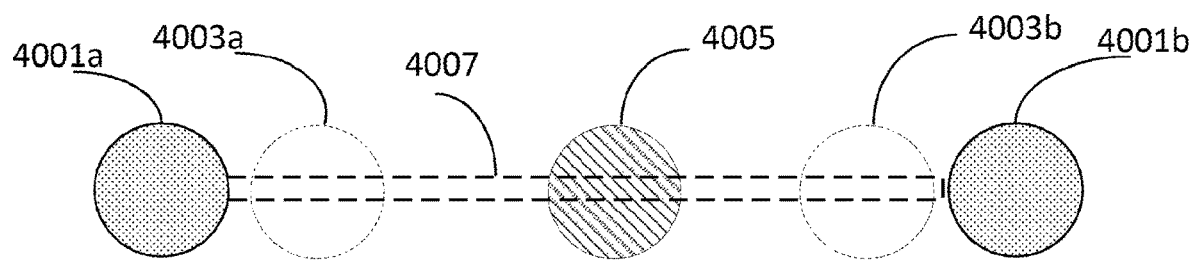
FIG. 40 schematically illustrates a method of interrogating the tissue in a region between two ultrasound excitation regions that are spaced apart from the corresponding treatment points using constructive shearwave imaging.

FIG. 40 schematically illustrates a method of interrogating the tissue in a region between two ultrasound excitation regions 4001a and 4001b using constructive shearwave imaging. The treatment points 4003a and 4003b corresponding to the excitation regions 4001a and 4001b are spaced apart from the corresponding excitation regions 4001a and 4001b using various techniques described in this application. For example, by using frequency modulation of the signals driving the ultrasound transducer, the treatment points 4003a and 4003b corresponding to the excitation regions 4001a and 4001b can be spaced apart from the corresponding excitation regions 4001a and 4001b. As another example, electronic dithering can be used to separate the treatment points 4003a and 4003b from the corresponding excitation regions 4001a and 4001b. As discussed above, the shearwaves generated from the two excitation regions 4001a and 4001b converge to a central region 4005 between the two excitation regions 4001a and 4001b. Various characteristics including but not limited to arrival time, peak displacement, rise time and fall time of the converging shearwaves in the central region 4005 can be obtained using an imaging system to determine elasticity of the tissue in the interrogation region 4007 which includes the treatment points 4003a and 4003b.

The methods of determining the elasticity of the tissue undergoing treatment can be between two excitation regions discussed above can be applied to determine the elasticity of the tissue between a plurality of excitation regions. The methods of determining the elasticity of the tissue undergoing treatment can be between two excitation regions discussed above can be used at any time during the creation of the two or more treatment points without physically moving the transducer module which can reduce or eliminate time delays between administering the ultrasound treatment and determining the effectiveness of the administered treatment.

As discussed above, various implementations of the ultrasound therapy system 20 discussed herein can include a movement mechanism that is configured to move the ultrasound transducer module, for example, along a line to create a plurality of treatment points with constant or variable spacing between consecutive treatment points of the plurality of treatment points. In such implementations, the method can be configured to determine the elasticity of the tissue between two excitation regions (or two treatment points) generated orthogonal to the direction of motion or along the direction of motion.

Figure 41:
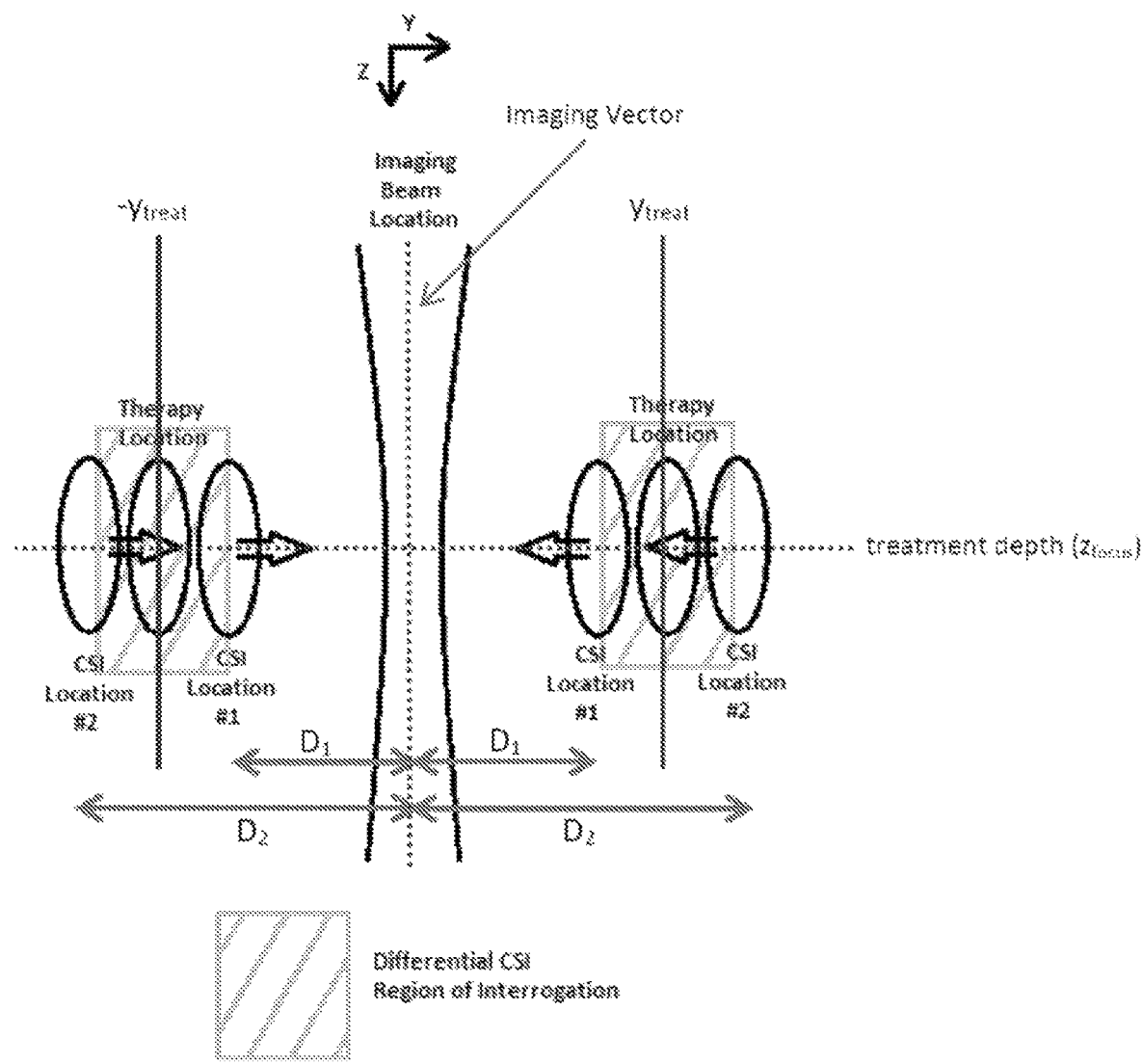
FIG. 41 schematically illustrates an embodiment of constructive shearwave imaging with a multi-focal transducer that involves modulating the transmit frequency for the excitation pulse.

FIG. 41 schematically illustrates an embodiment of constructive shearwave imaging with a multi-focal (e.g., two or more simultaneous foci) transducer that involves modulating the transmit frequency for the excitation pulse—one to shift the excitation inside the multi-focus thermal coagulation point TCP, and one to shift the excitation outside the multi-focus thermal coagulation point TCP. As a result, a differential shear wave velocity may be estimated specifically around the multi-focus TCP. In one embodiment, prior to delivering the therapy, two constructive shearwave imaging ("CSI") locations are created sequentially. As shown in an embodiment in FIG. 41, CSI location #1 is closest to the imaging beam location and may optionally be created first. The time to maximum displacement along the imaging beam is determined by tracking tissue motion changes along the imaging vector. Next, a CSI location #2 farthest from the imaging beam location is created. Another time to maximum displacement along the imaging vector is also determined. Since the distance the two shear waves travel are known along with the respective times, it is possible to calculate the shearwave velocity through the intended treatment region.

$$v_{shear}(y_{treat}) = \frac{D_2 - D_1}{t_2 - t_1}$$

This velocity estimate is the incremental shearwave velocity at the intended treatment site. In various embodiments, this concept does not only apply at the treatment site, but may be used outside the treatment site to obtain incremental shearwave velocity estimates throughout the entire plane (as shown in FIG. 41). After obtaining the initial shearwave velocity, focused therapy is delivered to the intended treatment site for a specific period of time, this time can range from microseconds to milliseconds to seconds or even minutes. After delivering the therapy, the process of measuring the incremental shearwave velocity is repeated. This process repeats itself until a shearwave velocity goal is obtained for the intended tissue that is being treated. In some embodiments, the amount of therapy delivered may be limited to the maximum allowable energy that can safely be delivered to tissue.

Figure 42:
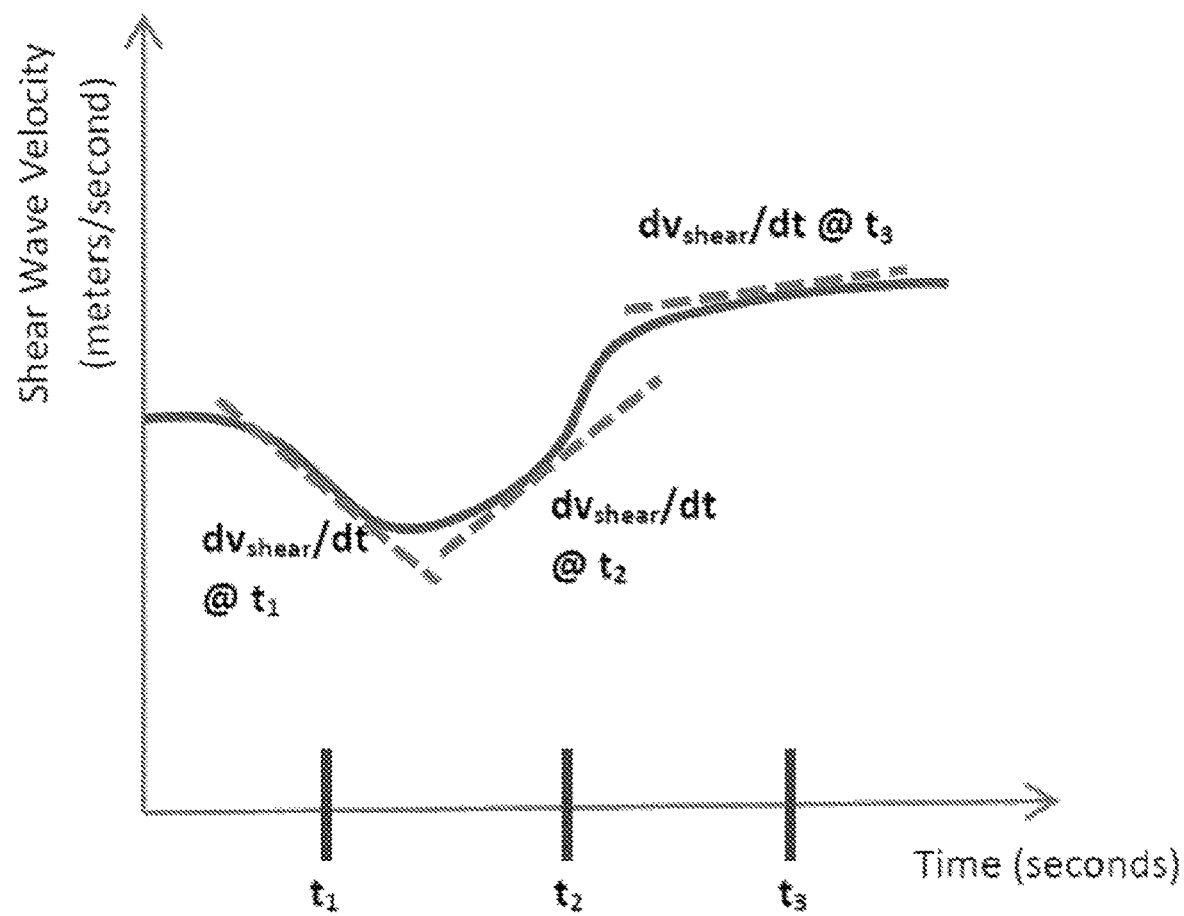
FIG. 42 schematically illustrates an embodiment of a chart showing changes to shearwave velocity as the tissue warms and coagulates.

A corresponding graph of shear wave velocity over treatment time is obtained using this technique. FIG. 42 schematically illustrates an embodiment of a chart showing changes to shearwave velocity as the tissue warms and coagulates. In one embodiment, after the baseline measurement is completed, the tissue is treated and begins to warm. Upon warming the tissue softens and shearwave velocity decreases initially at $t_1$. As therapy is continuously delivered, the tissue may begin to coagulate which causes it to stiffen and have an increased shearwave velocity as shown at $t_2$. Eventually, the tissue asymptotically approaches a maximum stiffness or maximum shearwave velocity at $t_3$. Although approaching this maximum shearwave velocity may be used to determine when to stop dosing, the corresponding shearwave velocity curve may also be used as feedback control the heating rate or when to stop delivering therapy based on the rate of change of shearwave velocity. In some embodiments, this approach may be advantageous due to the overall responsiveness and ability to predict when to stop the therapy.

In one embodiment, the system or method averages the shearwave velocity at $y_{treat}$ and $-y_{treat}$. In one embodiment, a phase walking aperture creates the shearwave at either only $y_{treat}$ or $-y_{treat}$ so the shearwave estimates from the two different locations are not averages together. In one embodiment, the CSI beam shape may be modified to create a shear wave along a wider range in depth rather than just localized to the treatment depth by either setting up multiple foci along the beam (already described in a previous disclosure) or reducing the f # of the CSI aperture. In one embodiment, a beat method is employed for the therapy beam to continuously generate shear waves as a method of measure.

Figure 43:
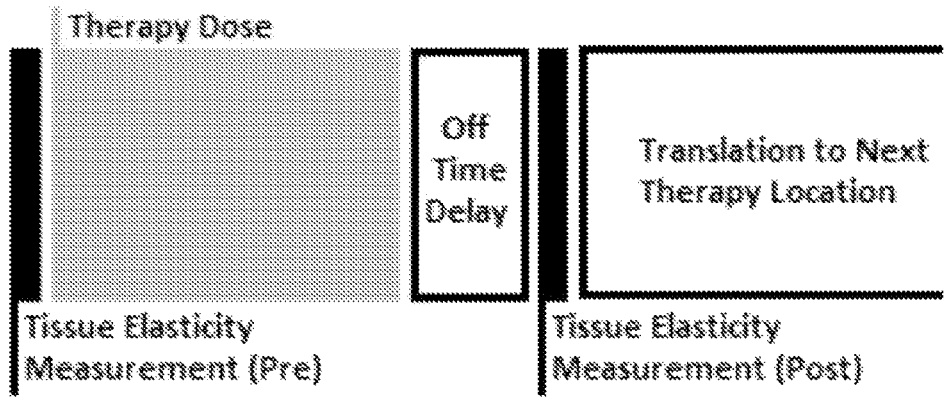
FIG. 43 schematically illustrates an embodiment of a method or system for tissue elasticity measurements and therapy dosing within a single sweep.
Figure 43:
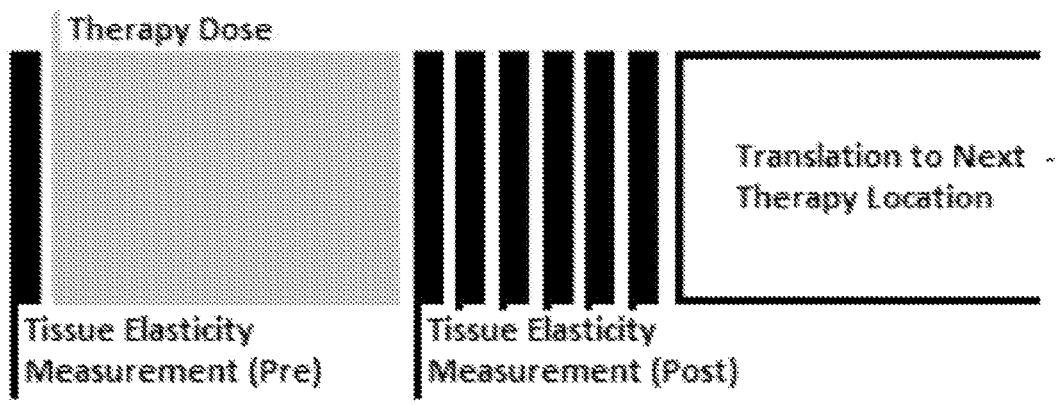
Figure 43:
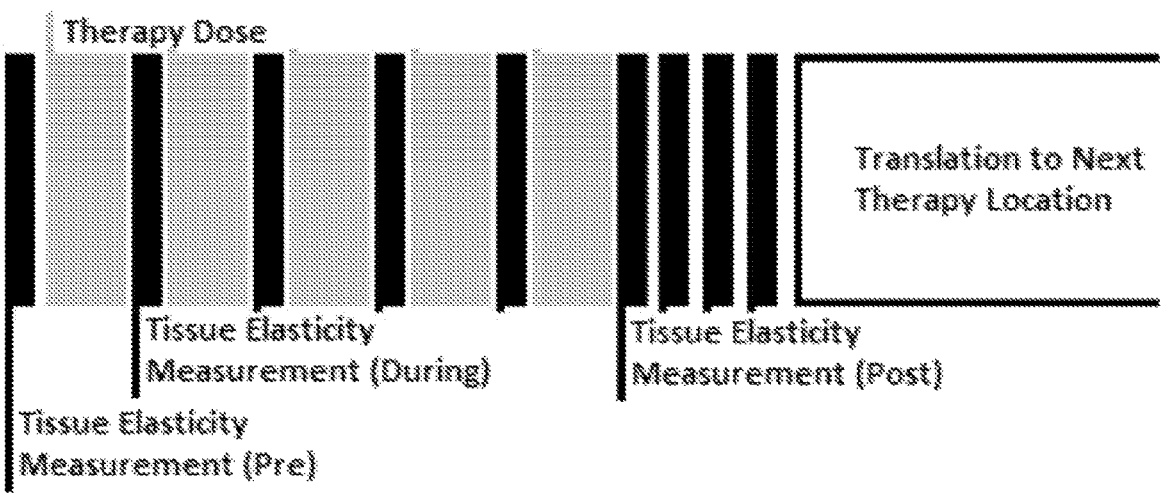

FIG. 43 schematically illustrates an embodiment of a method or system for tissue elasticity measurements and therapy dosing within a single sweep. In various embodiments, a sweep is a motion (left to right, right to left, in and out, out and in, egress and ingress) alone or in combination, in a curve, a straight line, a circle, in one dimension, two dimension, and/or three dimensions. In one embodiment, a first method involves a single measurement before the dose, the therapy dose, and a single measurement after the dose with a theoretical at an optimal time after the dose which may or may not require an off time delay. The purpose of the first measurement may be used to select an optimum treatment method. The purpose of the second measurement may be used to determine the effectiveness of the therapy. An off time may be used to allow transient tissue changes to subside prior to measurements. The effectiveness may be determined by reaching a key shear wave velocity or the percentage shear wave velocity change from the initial measurement.

In one embodiment, a second method is the same sequence as the first method but with multiple post-therapy elasticity measurements to observe transient elasticity changes within tissue in response to the therapeutic dose. In addition to observing the transient elasticity changes as the tissue reaches a new equilibrium state, the multiple post-therapy elasticity measurements may be used for averaging to create a better estimate of shear wave velocity change. Furthermore, the multiple elasticity measurements may be done both above and below the intended therapy region to estimate the extent the treated region.

In one embodiment, a third method is an interleaved sequence where multiple elasticity measurements are made in between therapy doses followed with multiple post-therapy elasticity measurements. Time-off between the ending of incremental therapy delivery and the start of the elasticity measurement is used to improve the elasticity measurement fidelity. This technique is used to determine when therapy delivery should end based on the elasticity changes. The treatment ends once the elasticity has changed by a certain percentage relative to the baseline measurement or has an achieved a specific level of elasticity change through heating. A maximum energy threshold is used to limit overdosing and guarantee a level of safety. The benefit of this technique only the necessary energy is used to achieve the tissue effects which improves safety and comfort.

In one embodiment, an optional interleaving of therapy with the tissue elasticity measurement may be included or excluded. In one embodiment, a multi-frequency DDS (e.g.

arbitrary waveform generator) is used with a device which excites the therapy transducer with multiple frequencies in CW and then modulates the amplitude of each excitation such that optional amplitude modulation pushes to create shearwaves yet the amplitude for the actual therapy region remains constant. In one embodiment, modulation of the therapy amplitude occurs if using a pre-programmed method (e.g. ramp up or ramp down) therapy delivery or feedback based on the elasticity measurements.

Figure 44:
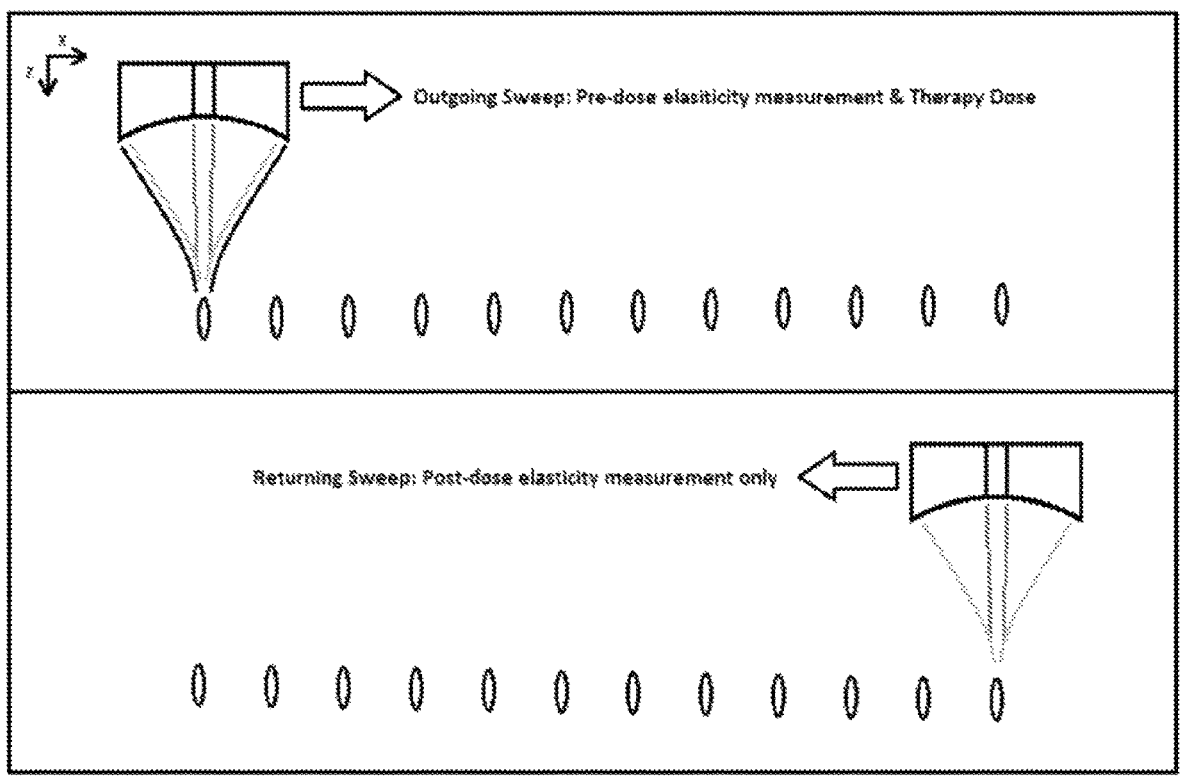
FIG. 44 schematically illustrates an embodiment of elasticity measurements as a single outgoing sweep comprises a pre-dose elasticity measurement followed by a therapy dose at each location.

FIG. 44 schematically illustrates an embodiment of elasticity measurements as a single outgoing sweep comprises a pre-dose elasticity measurement followed by a therapy dose at each location. Then, on the returning sweep, elasticity measurements only are made for post-dose assessment.

Figure 45:
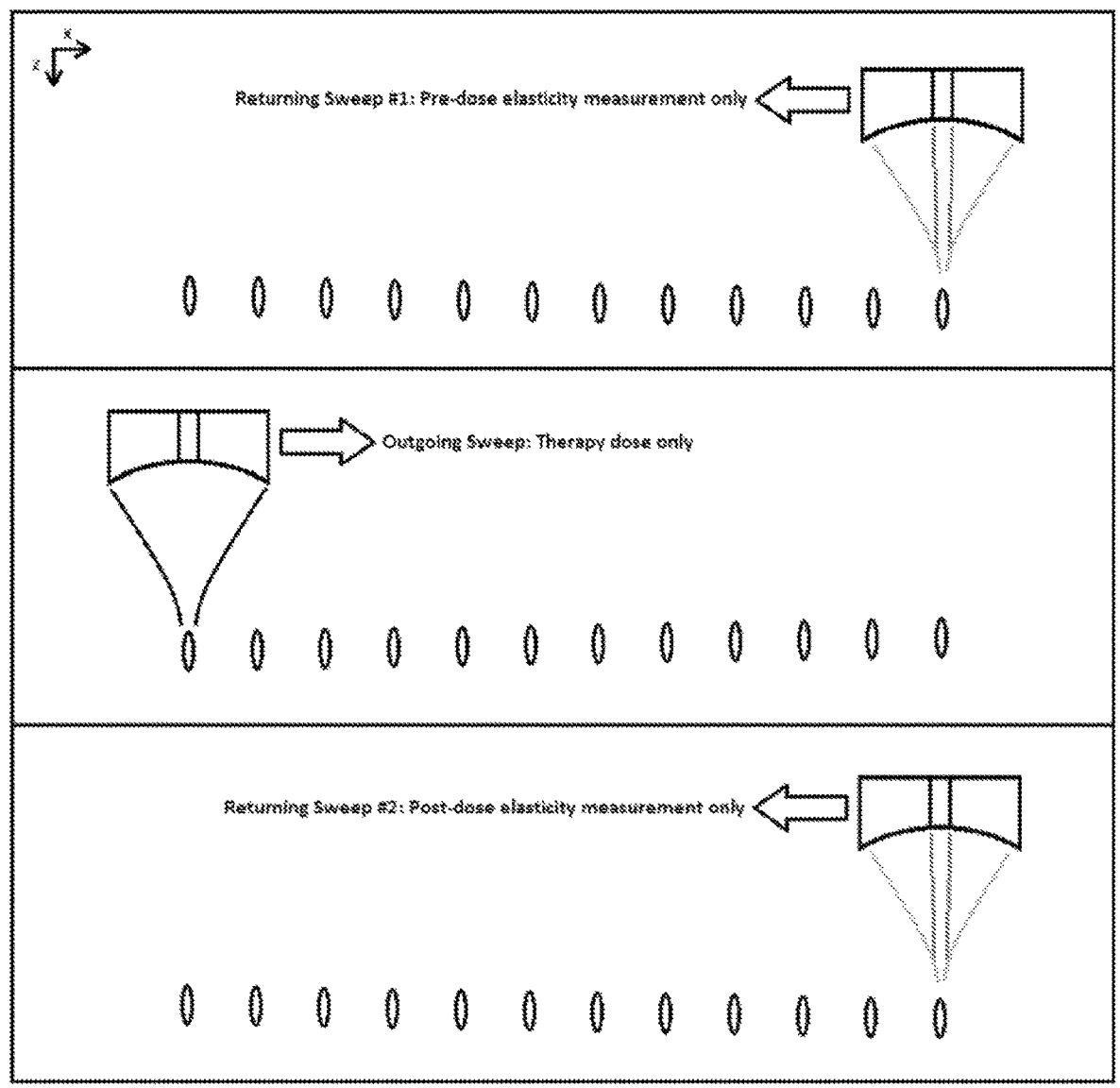
FIG. 45 schematically illustrates an embodiment of elasticity measurements before and/or after application of a therapy dose.

FIG. 45 schematically illustrates an embodiment of elasticity measurements before and/or after application of a therapy dose. The first sweep is an interrogation of the pre-therapy tissue elasticity at each TCP location. The following outgoing sweep applies therapy at each TCP location. The subsequent returning sweep interrogates post-therapy elasticity measurements at each TCP location.

Figure 46:
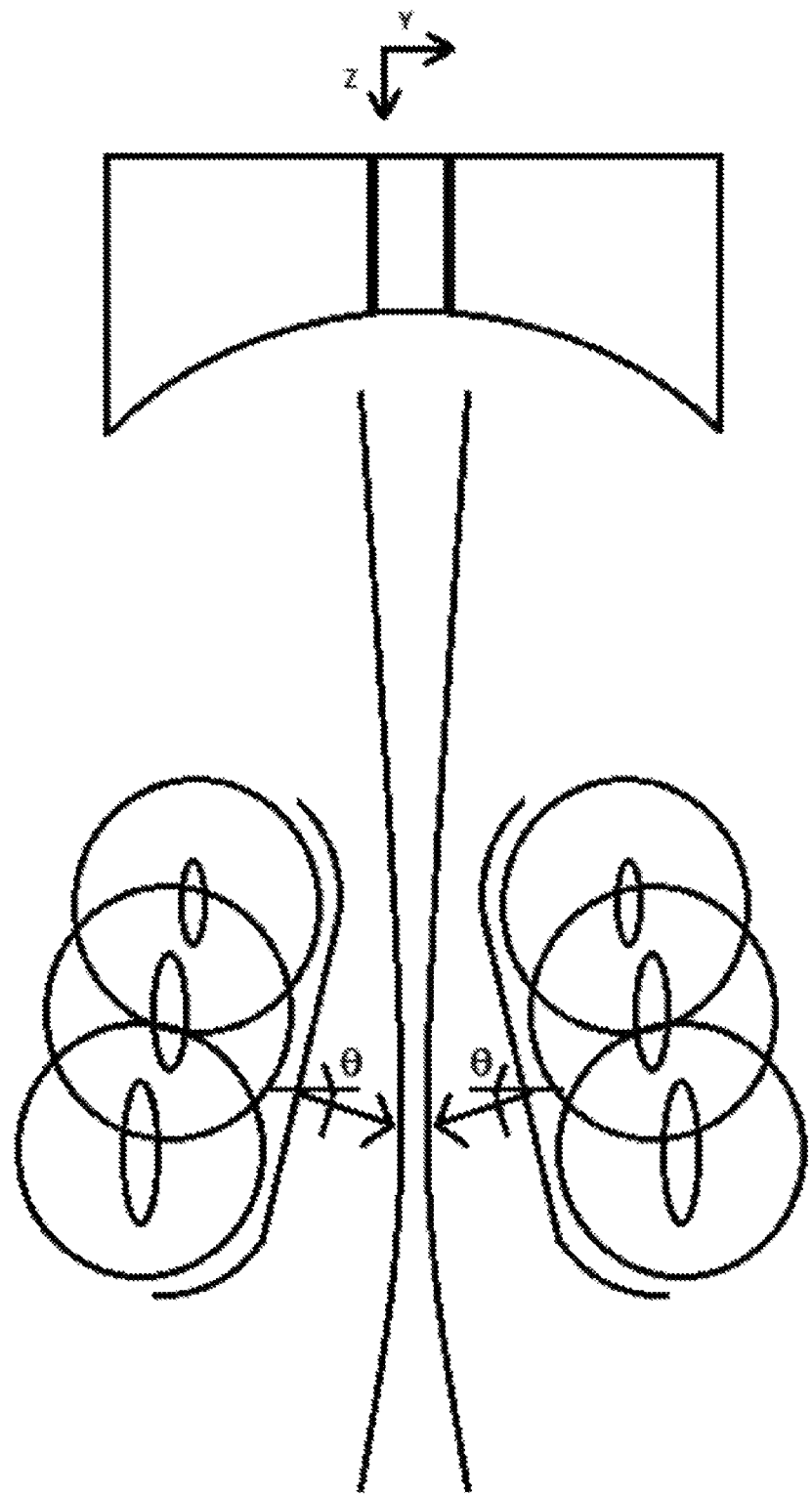
FIG. 46 schematically illustrates an embodiment of a CSI shearwave where the depth and excitation spacing of the region of excitation may be controlled.

FIG. 46 schematically illustrates an embodiment of a CSI shearwave where the depth and excitation spacing of the region of excitation may be controlled. In this embodiment, excitations may be generated at multiple spacing and multiple depths such that a broader shearwave propagates at a controlled angle (θ). Multiple estimates made from these excitations at different angles may provide insight into tissue anisotropy, including providing better layer definition. In one embodiment, longitudinal waves are faster than shearwaves. In one embodiments, measurements are made in multiple directions, (not limited to only lateral measurements). Angular encoding can measure different velocity at different angles (layers of muscle, tissue, skin boundaries, etc.).

The methods of determining the elasticity of the tissue undergoing ultrasound treatment discussed herein can be advantageously used to measure the effectiveness of the administered dose of acoustic energy. In various implementations, the effectiveness of the administered dose of acoustic energy can be determined during the ultrasound therapy. In some implementations, the administered dose can be adjusted in real time to increase the effectiveness of the ultrasound therapy based on the determined elasticity of the tissue being treated. For example, in some implementations, the dose of acoustic energy administered can be slowly increased to a dose that results in a particular elasticity of the tissue being treated which would provide a desired clinical outcome. The dose of acoustic energy that achieves a desired clinical outcome may be different for different patients. The constructive shearwave . . . imaging method to determine the elasticity of the tissue being treated advantageously allows for the dose of acoustic energy to be tailored for an individual patient. Integrating the constructive shearwave imaging method to determine the elasticity of the tissue being treated with the ultrasound system can also improve safety. For example, in some existing systems, a fixed amount of acoustic energy may be delivered to all patients to achieve a clinical result. Depending on an individual patient's morphology, the fixed amount may cause the tissue to heat quickly and cause discomfort to the patient. Monitoring the effectiveness of the ultrasound therapy using the constructive shearwave imaging method described herein can tailor the dose of the administered ultrasound energy to an individual patient's needs.

Various advantages of the embodiments of a simultaneous multiple depth treatment device configured to create multiple TCP's at various depths include the creation of simultaneous TCPs at multiple depths. In one embodiment, an advantage is the elimination of multiple transducers, thereby reducing the transducer swapping by the operator. In one embodiment, an advantage is faster treatment time. In one embodiment, an advantage is fewer button presses deliver the same number of lines. In one embodiment, an advantage is modulation of the distance between the TCPs delivered simultaneously. In one embodiment, an advantage is maintaining the pitch separation of the TCPs at each depth along the line of mechanical motion. In one embodiment, an advantage is the avoidance of pulse stacking at multiple depths. In one embodiment, an advantage is the ability to create larger zones of coagulation and apoptosis. In one embodiment, an advantage is enabling the ability to deliver lines of micro-coagulation along three dimensions. In one embodiment, an advantage of using an electrostrictor, includes creating more than two lines with one transducer placement on a patient's body. In one embodiment, an advantage of using an electrostrictor is modulating the distance between the simultaneously delivered TCPs. In one embodiment, an advantage is modulating the ability to mute spatial high frequency harmonics from the simultaneous therapy modulation pattern. In one embodiment, an advantage of using an electrostrictor offers the possibility of adding nulls to the modulation pattern.

Some embodiments and the examples described herein are examples and not intended to be limiting in describing the full scope of compositions and methods of these invention. Equivalent changes, modifications and variations of some embodiments, materials, compositions and methods can be made within the scope of the present invention, with substantially similar results.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "coupling a transducer module with an ultrasonic probe" include "instructing the coupling of a transducer module with an ultrasonic probe." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 25 mm" includes "25 mm."

What is claimed is:

1. A system for measuring material elasticity, the system comprising:
   an ultrasonic probe comprising an ultrasound transducer configured to deliver a plurality of ultrasound beams to a material,
   the material comprising an elasticity,
   the plurality of ultrasound beams being focused at a plurality of individually spaced focal zones in the material, each ultrasound beam having sufficient acoustic power to generate a shear wave originating from the individually spaced focal zones and travelling through the material;

an ultrasound imaging system configured to image shear waves originating from at least two of the plurality of individually spaced focal zones and converging via an interrogation region towards a region between the at least two of the plurality of individually spaced focal zones; and an electronic processing system configured to:
obtain a characteristic of the imaged shear waves; and
determine the elasticity of the interrogation region of the material based on the obtained characteristic.

2. The system of claim 1, wherein the characteristic of the imaged shear waves includes at least one of an arrival time of the shear waves, a peak displacement of the shear waves, rise time of the shear waves, and fall time of the shear waves.

3. The system of claim 1, wherein the ultrasound transducer is configured to deliver the ultrasound beam to the material using amplitude modulation to focus the ultrasound beam at the plurality of individually spaced focal zones in the material.

4. The system of claim 1, wherein the at least one ultrasound transducer is configured to deliver the ultrasound beam to a plurality of excitation zones of the material corresponding to the plurality of individually spaced focal zones.

5. The system of claim 1, further comprising a movement assembly configured to move the ultrasonic probe.

6. The system of claim 1, wherein the electronic processing system is configured to determine elasticity of the material in real-time while the ultrasound beam is delivered to the material.

7. The system of claim 1, configured for use in a cosmetic procedure.

8. A method of non-invasively measuring elasticity of a material, the method comprising:
coupling an ultrasonic probe comprising at least one ultrasound transducer with a material;
delivering a plurality of ultrasound beams from the ultrasonic transducer to the material;
focusing the plurality of ultrasound beams at a plurality of individually spaced focal zones in the material;
generating shear waves originating from the plurality of individually spaced focal zones and travelling through the material;
imaging the shear waves originating from at least two of the plurality of individually spaced focal zones and converging via an interrogation region towards a region between the at least two of the plurality of individually spaced focal zones;
obtaining a characteristic of the imaged shear waves; and
determining elasticity of the interrogation region of the material based on the obtained characteristic.

9. The method of claim 8, wherein the characteristic of the imaged shear waves includes at least one of an arrival time of the shear waves, a peak displacement of the shear waves, rise time of the shear waves, and fall time of the shear waves.

10. The method of claim 8, wherein focusing the ultrasound beam at a plurality of individually spaced focal zones in the material comprises modulating amplitude or frequency of one or more signals driving the ultrasound transducer.

11. The method of claim 8, wherein the ultrasound beam is delivered to a plurality of excitation zones of the material corresponding to the plurality of individually spaced focal zones.

12. The method of claim 8, further comprising moving the ultrasonic probe to focus the ultrasound beam at the plurality of individually spaced focal zones in the material.

13. The method of claim 8, wherein the material comprises an organic material.

14. The method of claim 8, wherein the elasticity of the material is determined in real-time while the ultrasound beam is delivered to the material.

15. The method of claim 8, further comprising determining efficacy of an ultrasound therapy configured to provide cosmetic or aesthetic improvements in the material, wherein the material comprises a biological tissue.

16. The method of claim 15, wherein determining efficacy of an ultrasound therapy configured to provide cosmetic or aesthetic improvements comprises correlating the determined elasticity to creation of a thermal coagulation point (TCP) in the biological tissue.

17. A method of measuring elasticity of a material by creating multiple simultaneous focal points, the method comprising:
coupling an ultrasonic transducer probe to a material surface;
wherein the ultrasonic transducer probe comprises a single piezoelectric transduction element configured to focus a plurality of individual spaced focal zones;
focusing a plurality of individual spaced focal zones in a region below the material surface with the single piezoelectric transduction element, wherein the focusing at the plurality of individual spaced focal zones is simultaneous;
obtaining a characteristic of a plurality of shear waves originating from at least two of the plurality of individual focal zones converging via an interrogation region towards a region between the at least two of the plurality of individual focal zones;
determining elasticity of the interrogation region below the skin surface between the at least two of the plurality of individual focal zones from the obtained characteristic of the shear wave; and
determining an effectiveness of the noninvasive cosmetic procedure based on the determined elasticity,
wherein the transducer module comprises a single ultrasound transducer configured to apply ultrasonic therapy to tissue at a plurality of individual excitation zones corresponding to the individual focal zones.

18. The method of claim 17, wherein the characteristic of the shear waves includes at least one of an arrival time of the shear waves, a peak displacement of the shear waves, rise time of the shear waves, and fall time of the shear waves.

19. The method of claim 17, wherein an individual excitation zone of the plurality of individual excitation zones coincides with a corresponding one of the plurality of individual focal zones.

20. The method of claim 17, wherein an individual excitation zone of the plurality of individual excitation zones is spaced apart from a corresponding one of the plurality of individual focal zones.

* * * * *